US012589157B1

(12) United States Patent
Barnes et al.

(10) Patent No.: US 12,589,157 B1
(45) Date of Patent: Mar. 31, 2026

(54) COMPOSITIONS OF DRUG DELIVERY AGENTS AND METHODS OF USE THEREOF

(71) Applicants: Jonathan C. Barnes, St. Louis, MO (US); Xuesong Li, St. Louis, MO (US); Abigail Delawder, St. Louis, MO (US); Ruihan Li, St. Louis, MO (US)

(72) Inventors: Jonathan C. Barnes, St. Louis, MO (US); Xuesong Li, St. Louis, MO (US); Abigail Delawder, St. Louis, MO (US); Ruihan Li, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 16/370,316

(22) Filed: Mar. 29, 2019

Related U.S. Application Data

(60) Provisional application No. 62/649,735, filed on Mar. 29, 2018.

(51) Int. Cl.

| | |
|---|---|
| *A61K 47/58* | (2017.01) |
| *A61K 45/06* | (2006.01) |
| *A61K 47/22* | (2006.01) |
| *A61K 47/40* | (2006.01) |
| *A61K 47/69* | (2017.01) |
| *A61P 31/04* | (2006.01) |
| *A61P 35/02* | (2006.01) |
| *C08G 61/06* | (2006.01) |

(52) U.S. Cl.
CPC ............. *A61K 47/58* (2017.08); *A61K 45/06* (2013.01); *A61K 47/22* (2013.01); *A61K 47/40* (2013.01); *A61K 47/6907* (2017.08); *A61P 31/04* (2018.01); *A61P 35/02* (2018.01); *C08G 61/06* (2013.01); *C08G 2261/3324* (2013.01); *C08G 2261/374* (2013.01); *C08G 2261/418* (2013.01)

(58) Field of Classification Search
CPC .... A61K 47/56; A61K 47/60; A61K 47/6907; A61K 47/40; A61K 47/58; A61K 45/06; A61K 47/22; A61P 31/04; A61P 35/02; C08G 61/06; C08G 2261/3324; C08G 2261/374; C08G 2261/418
See application file for complete search history.

(56) References Cited

U.S. PATENT DOCUMENTS

| | | |
|---|---|---|
| 2014/0141375 A1 | 5/2014 | Cho |
| 2014/0193342 A1 | 7/2014 | Gianneschi |
| 2016/0243141 A1 | 8/2016 | Lu |

FOREIGN PATENT DOCUMENTS

| | | | |
|---|---|---|---|
| WO | 2015/054269 A1 | * | 4/2015 |

OTHER PUBLICATIONS

Aki et al, Journal of Thermal Analysis and Calorimetry (2006), vol. 85, pp. 685-688. (Year: 2006).*
Boudebbouze et al, Chem Commun 2013, vol. 49, pp. 7150-7152. (Year: 2013).*
Li et al, Advanced Science, first published Feb. 22, 2018, vol. 5, pp. 1-17. (Year: 2018).*
Johnson et al, Macromolecules 2011, PMC, pp. 1-24 (Year: 2011).*
Peng et al, Molecular Pharmaceutics 2017, vol. 14, pp. 2575-2486. (Year: 2017).*
Li et al, Chinese Chemical Letters 24 (2013) 545-552. (Year: 2013).*
Chen (PLOS One, Published Mar. 10, 2016, pp. 1-13) (Year: 2016).*
Alexandridis, P., Holzwarth, J. F., Hatton, T. A. (1994), Micellization of Poly(ethylene oxide)-Poly(propylene oxide)-Poly(ethylene oxide) Triblock Copolymers in Aqueous Solutions: Thermodynamics of Copolymer Association, Macromol., vol. 27, pp. 2414-2425.
Barber, M., Rozwadowska-Dowzenko, M. (1948), Infection by Penicillin Resistant Staphylococci, Lancet, vol. 252, No. 6530, pp. 641-644.
Barbul, A., et al. (1990), Arginine Enhances Wound Healing and Lymphocyte Immune Responses in Humans, Surgery, vol. 108, No. 2, pp. 331-337.
Barnes, J. C., et al. (2016), Using an RNAi Assay to Guide the Design of Three-Drug-Conjugated Nanoparticles with Validated Mechanisms, In Vivo Efficacy, and Low Toxicity, J. Am. Chem. Soc., vol. 138, No. 38, pp. 12494-12501.
Biba, E. (2017), How we can stop antibiotic resistance. Retrieved from http://www.bbc.com/future/story/20170607-how-we-can-stop-antibiotic-resistance on Jun. 24, 2019, pp. 1-10.
Bielawski, C. W., Grubbs, R. H. (2007), Living Ring-Opening Metathesis Polymerization, Prog. Polym. Sci., vol. 32, pp. 1-29.
Boucher, H. W., Corey, G. R. (2008), Epidemiology of methicillin-resistant *Staphylococcus aureus*, Clin. Infect. Dis., vol. 46, pp. S344-S349.
Boucher, H. W. et al. (2009), Bad Bugs, No Drugs: No. Eskape! An Update from the Infectious Diseases Society of America, Clin. Infect. Dis., vol. 48, pp. 1-12.
Brink, S. (2017), A superbug that resisted 26 antibiotics. Retrieved from https://www.npr.org/sections/goatsandsoda/2017/01/17/510227493/a-superbug-that-resisted-26-antibiotics on Jun. 24, 2019, pp. 1-4.
Bush, K. et al. (2011), Tackling Antibiotic Resistance, Nature Rev. Microbiol., vol. 9, No. 12, pp. 894-896.
Camm, K. D. (2007), Tandem ROMP-Hydrogenation with a Third-Generation Grubbs Catalyst, J. Am. Chem. Soc., vol. 129, pp. 4168-4169.
Chen, J. et al. (2014), Antibacterial Polymeric Nanostructures for Biomedical Applications, Chem. Commun., vol. 50, No. 93, pp. 14482-14493.
Dantes, R. et al. (2013), National Burden of Invasive Methicillin-Resistant *Staphylococcus aureus* Infections, United States, 2011, JAMA Intern. Med., vol. 173, No. 21, pp. 1970-1978.
Escobedo, J. O. et al. (2010), NIR Dyes for Bioimaging Applications, Curr. Opin. Chem. Biol., vol. 14, No. 1, pp. 64-70.

(Continued)

*Primary Examiner* — Alma Pipic

(57) ABSTRACT

Provided herein are compositions and methods of making and using drug-binding polymers or nanoparticles for targeted therapies. In some embodiments the drug-binding polymers or nanoparticles can deliver two or more of an antibiotic, an alkali or transition metal cation, or anticancer agents.

10 Claims, 15 Drawing Sheets

(56)                    References Cited

OTHER PUBLICATIONS

Feng K. et al. (2016), Modular Design of Poly(norbornenes) for Organelle-Specific Imaging in Tumor Cells (Supporting Information), Biomacromolecules, vol. 17, No. 2, pp. 538-545.

Fleming, A. (1929), On the Antibacterial Action of Cultures of a Penicillium, with Special Reference to their Use in the Isolation of B. influenzae, Br. J. Exp. Pathol, vol. 10, No. 3, pp. 226-236.

Gidwani, B., Vyas, A. (2015), A Comprehensive Review on Cyclodextrin-Based Carriers for Delivery of Chemotherapeutic Cytotoxic Anticancer Drugs, Biomed Research International, vol. 2015, pp. 1-15.

Guan, Y., Qian, L., Xiao, H. (2007), Novel Anti-Microbial Host-Guest Complexes Based on Cationic β-Cyclodextrin Polymers and Triclosan/Butylparaben, Macromol. Rapid Commun., vol. 28, pp. 2244-2248.

Irie, T., Uekama, K. (1997), Pharmaceutical Applications of Cyclodextrins. III. Toxicological Issues and Safety Evaluation, J. Pharm. Sci., vol. 86, No. 2, pp. 147-162.

Iseman, M. D. (1993), Treatment of Multidrug-Resistant Tuberculosis, N. Engl. J. Med., vol. 329, No. 11, pp. 784-791.

Johnson, J.A. et al. (2010), Drug-Loaded, Bivalent-Bottle-Brush Polymers by Graft-through ROMP, Macromolecules, vol. 43, pp. 10326-10335.

Kardos, N., Demain, A. L. (2011), Penicillin: The Medicine with the Greatest Impact on Therapeutic Outcomes, Appl. Microbiol. Biotechnol., vol. 92, pp. 677-687.

Kelly, J. F. et al. (2008), Injury Severity and Causes of Death From Operation Iraqi Freedom and Operation Enduring Freedom: 2003-2004 Versus 2006. J. Trauma-Injury Infect. Crit. Care, vol. 64, No. 2, S21-S27.

Kongor A.R. et al. (2016), Calix-Based Nanoparticles: A Review, Top Curr Chem, vol. 374, No. 28, pp. 1-46.

Lara, H. H. et al. (2011), K. Silver Nanoparticles are Broad-Spectrum Bactericidal and Virucidal Compounds, J. Nanobiotechnol., vol. 9, No. 30, pp. 1-8.

Law, D. (2009). "Adipic Acid", Handbook of Pharmaceutical Excipients, 6th ed., Pharmaceutical Press, London, UK, pp. 11-12.

Levy, S. B. (1982), Microbial Resistance to Antibiotics. An Evolving and Persistent Problem, vol. 320, No. 8289, pp. 83-88.

Levy, S. B., Marshall, B. (2004), Antibacterial Resistance Worldwide: Causes, Challenges, and Responses, Nature Med., vol. 10, No. 12, pp. S122-S129.

Lewis, K. (2012), Recover the lost art of drug discovery, Nature, vol. 485, pp. 439-440.

Li, H. et al. (2011), Structure-based in Silico Model Profiles the Binding Constant of Poorly Soluble Drugs with β-Cyclodextrin, Eur. J. Pharm. Sci., vol. 42, pp. 55-64.

Liao, L. et al. (2014), A Convergent Synthetic Platform for Single-Nanoparticle Combination Cancer Therapy: Ratiometric Loading and Controlled Release of Cisplatin, Doxrubicin, and Camptothecin, J. Am. Chem. Soc., vol. 136, No. 16, pp. 5896-5899.

Lienkamp, K. et al. (2009), Antimicrobial Polymers Prepared by Ring-Opening Metathesis Polymerization: Manipulating Antimicrobial Properties by Organic Counterion and Charge Density Variation, Chem. Eur. J., vol. 15, pp. 11715-11722.

Lim, Y. H. et al. (2015), Preparation and in Vitro Antimicrobial Activity of Silver-Bearing Degradable Polymeric Nanoparticles of Polyphosphoester-block-Poly(L-lactide), ACS Nano, vol. 9, No. 2, pp. 1995-2008.

Liong, M. et al. (2009), Antimicrobial Activity of Silver Nanocrystals Encapsulated in Mesoporous Silica Nanoparticles, Adv. Mater, vol. 21, pp. 1684-1689.

Liu, Z., Nalluri, S. K. M., Stoddart, J. F. (2017), Surveying macrocyclic chemistry: from flexible crown ethers to rigid cyclophanes, Chem. Soc. Rev., vol. 46, No. 9, pp. 2459-2478.

Madkour, A. E. et al. (2010), End-Functionalized ROMP Polymers for Biomedical Applications, Macromolecules, vol. 43, pp. 4557-4561.

Mayer, L. D., Janoff, A. S. (2007), Optimizing combination chemotherapy by controlling drug ratios, Mol. Interv., vol. 7, No. 4, pp. 216-223.

Mcgivney, E. et al. (Mar. 6, 2018), Quorum sensing signals form complexes with Ag+ and Cu2+cations, ACS Chem. Biol., vol. 13, pp. 894-899.

Miki, K. et al (2010), Ring-opening metathesis polymerization-based synthesis of polymeric nanoparticles for enhanced tumor imaging in vivo: Synergistic effect of folate-receptor targeting and PEGylation, Biomaterials, vol. 31, No. 5, pp. 934-942.

Morohashi, N. et al. (2006), Thiacalixarenes, Chem. Rev., vol. 106, pp. 5291-5316.

Morones-Ramirez, J. R. et al. (2013), Silver enhances antibiotic activity against gram-negative bacteria, Sci. Trans. Med., vol. 5, No. 190 pp. 1-11.

Panacek, A. et al. (2006), Silver Colloid Nanoparticles: Synthesis, Characterization, and Their Antibacterial Activity, J. Phys. Chem. B, vol. 110, pp. 16248-16253.

Peer, D. et al. (2007), Nanocarriers as an emerging platform for cancer therapy, Nature Nanotech, vol. 2, pp. 751-760.

Poole, K. et al. (1993), Multiple Antibiotic Resistance in Pseudomonas aeruginosa: Evidence for Involvement of an Efflux Operon, J. Bacteriol., vol. 175, No. 22, pp. 7363-7372.

Rai, M., Yadav, A., Gade, A. (2009), Silver Nanoparticles as a New Generation of Antimicrobials, Biotechnol. Adv., vol. 27, No. 1, pp. 76-83.

Ramasamy, T. et al. (2017), Smart chemistry-based nanosized drug delivery systems for systemic applications: A comprehensive review, Journal of Controlled Release, vol. 258, pp. 226-253.

Richter, A. P. et al. (2015), An environmentally benign antimicrobial nanoparticle based on a silver-infused lignin core, Nature Nanotech, vol. 10, pp. 817-823.

Roberts, R. R. et al. (2009), Hospital and Societal Costs of Antimicrobial-Resistant Infections in a Chicago Teaching Hospital: Implications for Antibiotic Stewardship, Clin. Infect. Dis., vol. 49, No. 8, pp. 1175-1184.

Schatz, A., Bugie, E., Waksman, S. A. (1944), Streptomycin, a Substance Exhibiting Antibiotic Activity Against Gram-positive and Gram-negative Bacteria, Proc. Soc. Exp. Biol. Med, vol. 55, pp. 66-69.

Schmidt, N. W. et al. (2011), Criterion for Amino Acid Composition of Defensins and Antimicrobial Peptides Based on Geometry of Membrane Destabilization, J. Am. Chem. Soc., vol. 133, pp. 6720-6727.

Shahverdi, A. R. et al. (2007), Synthesis and Effect of Silver Nanoparticles on the Antibacterial Activity of Different Antibiotics Against *Staphylococcus aureus* and *Escherichia coli*, Nanomed.-Nanotechnol., vol. 3, pp. 168-171.

Sharma, V. K., Yngard, R. A., Lin, Y. (2009), Silver Nanoparticles: Green Synthesis and Their Antimicrobial Activities, Adv. Colloid Interfac., vol. 145, pp. 83-96.

Som, A. et al. (2008), Synthetic Mimics of Antimicrobial Peptides, Biopolymers (Pept. Sci.), vol. 90, No. 2, pp. 83-93.

Sondi, I., Salopek-Sondi, B. (2004), Silver Nanoparticles as Antimicrobial Agent: A Case Study on *E. coli* as a Model for Gram-negative Bacteria, J. Colloid Interface Sci., vol. 275, pp. 177-182.

Sowers, M. A. et al. (2014), Redox-Responsive Branched-Bottlebrush Polymers for In Vivo MRI and Fluorescence Imaging, Nature Commun, vol. 5, pp. 1-9.

Tian, Y. et al. (2014), Facile One-Pot Synthesis, and Antibacterial Activity of Mesoporous Silica Nanoparticles Decorated with Well-Dispersed Silver Nanoparticles, ACS Appl. Mater. Interfaces, vol. 6, No. 15, pp. 12038-12045.

Unknown. (1973), Select Committee on GRAS Substances (SCOGS) Opinion: Sodium Alginate, U.S. Food and Drug Administration. Retrieved from http://www.fda.gov/Food/IngredientsPackagingLabeling/GRAS/SCOGS/ucm261098.htm on Jul. 3, 2019, pp. 1-2.

Unknown. (2011), Folfirinox, NIH National Cancer Institute. Retrieved from https://www.cancer.gov/about-cancer/treatment/drugs/FOLFIRINOX on Jun. 14, 2019, pp. 1-2.

Unknown. (Feb. 2018), Antibiotic Resistance, World Health Organization. Retrieved from https://www.who.int/en/news-room/fact-sheets/detail/antibiotic-resistance on Jun. 24, 2019, pp. 1-6.

(56) References Cited

OTHER PUBLICATIONS

Unknown. About Antimicrobial Resistance, Centers for Disease Control and Prevention. Retrieved from http://www.cdc.gov/drugresistance/about.html on Jun. 14, 2019, pp. 1-2.

Unknown. Biggest Threats and Data, Centers for Disease Control and Prevention. Retrieved from https://www.cdc.gov/drugresistance/biggest_threats.html on Jun. 24, 2019, pp. 1-7.

Vijayakameswara, R.N. et al. (2012), Norbornene Derived Doxorubicin Copolymers as Drug Carriers with pH Responsive Hydrazone Linker, Biomacromolecules, vol. 13, pp. 221-230.

Vijayakameswara, R.N. et al. (2014), Smart nanocarrier from norbornene based triblock copolymers for the sustained release of multicancer drugs, Royal Society of Chemistry, vol. 4, pp. 45625-45634.

Vijayakameswara, R.N. et al. (2014), Efficient approach to prepare multiple chemotherapeutic agent conjugated nanocarrier, Royal Society of Chemistry, vol. 50, pp. 13540-13543.

Wakshlak, R. B.-K., Pedahzur, R., Avnir, D. (2015), Antibacterial Activity of Silver-Killed Bacteria: The "Zombies" Effect, Sci. Rep., vol. 5, pp. 1-5.

Wang, C.E. et al. (2015), Polymer Nanostructures Synthesized by Controlled Living Polymerizationfor Tumor-Targeted Drug Delivery, Journal of Controlled Release, vol. 219, pp. 345-354.

Westphalen, C. B., Olive, K. P. (2012), Genetically engineered mouse models of pancreatic cancer, Cancer J., vol. 18, No. 6, pp. 502-510.

Wilhelm, S. et al. (2016), Analysis of Nanoparticle Delivery to Tumours, Nat. Rev. Mater, vol. 1, No. 5, pp. 1-12.

Wong, C.E. et al. (2017), Cyclodextrins: A Weapon in the Fight Against Antimicrobial Resistance, vol. 5, No. 1, pp. 1740006-1-1740006-9.

Yu, Y., Sun, H., Cheng, C. (2017), "Chapter 8—Brush polymer-based nanostructures for drug delivery", Nanostructures for Drug Delivery, Elsevier Inc., pp. 271-298.

Zhang, H. et al. (2015), Well-Defined Polyethylene-Based Random, Block, and Bilayered Molecular Cobrushes, Macromolecules, vol. 48, pp. 3556-3562.

Zhao, X., Li, H., Lee, R. J. (2008), Targeted drug delivery via folate receptors, Expert Opin. Drug Deliv., vol. 5, No. 3, pp. 309-319.

* cited by examiner

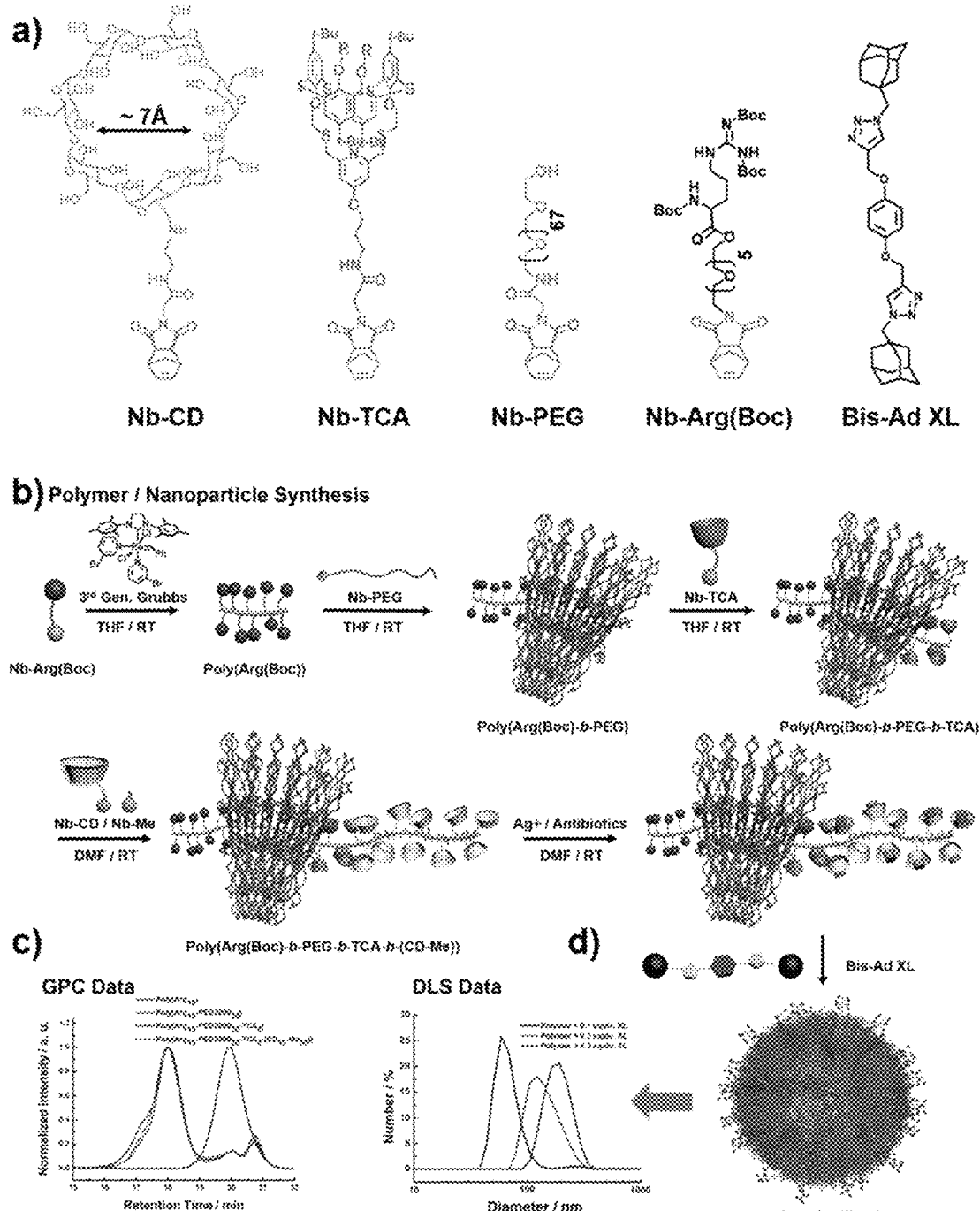

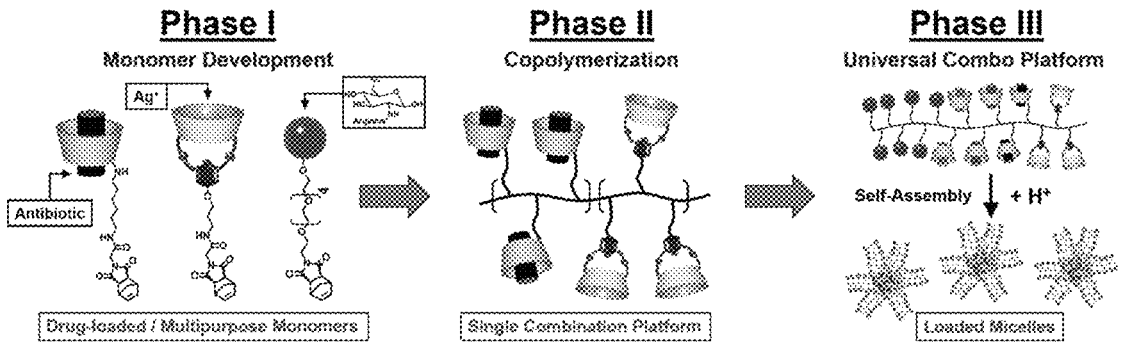
FIG. 5
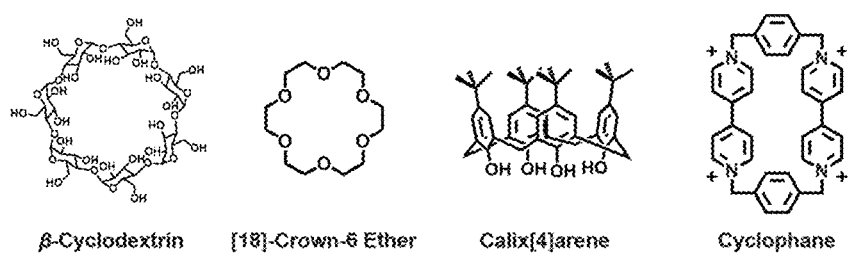
FIG. 6
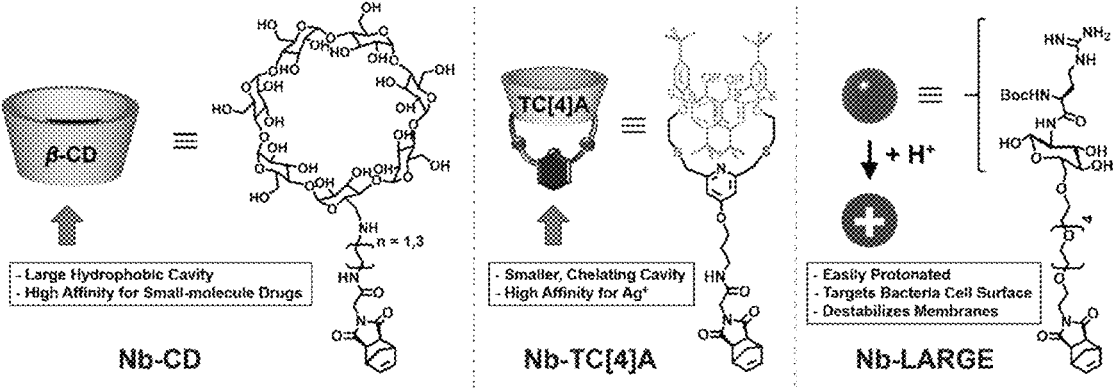

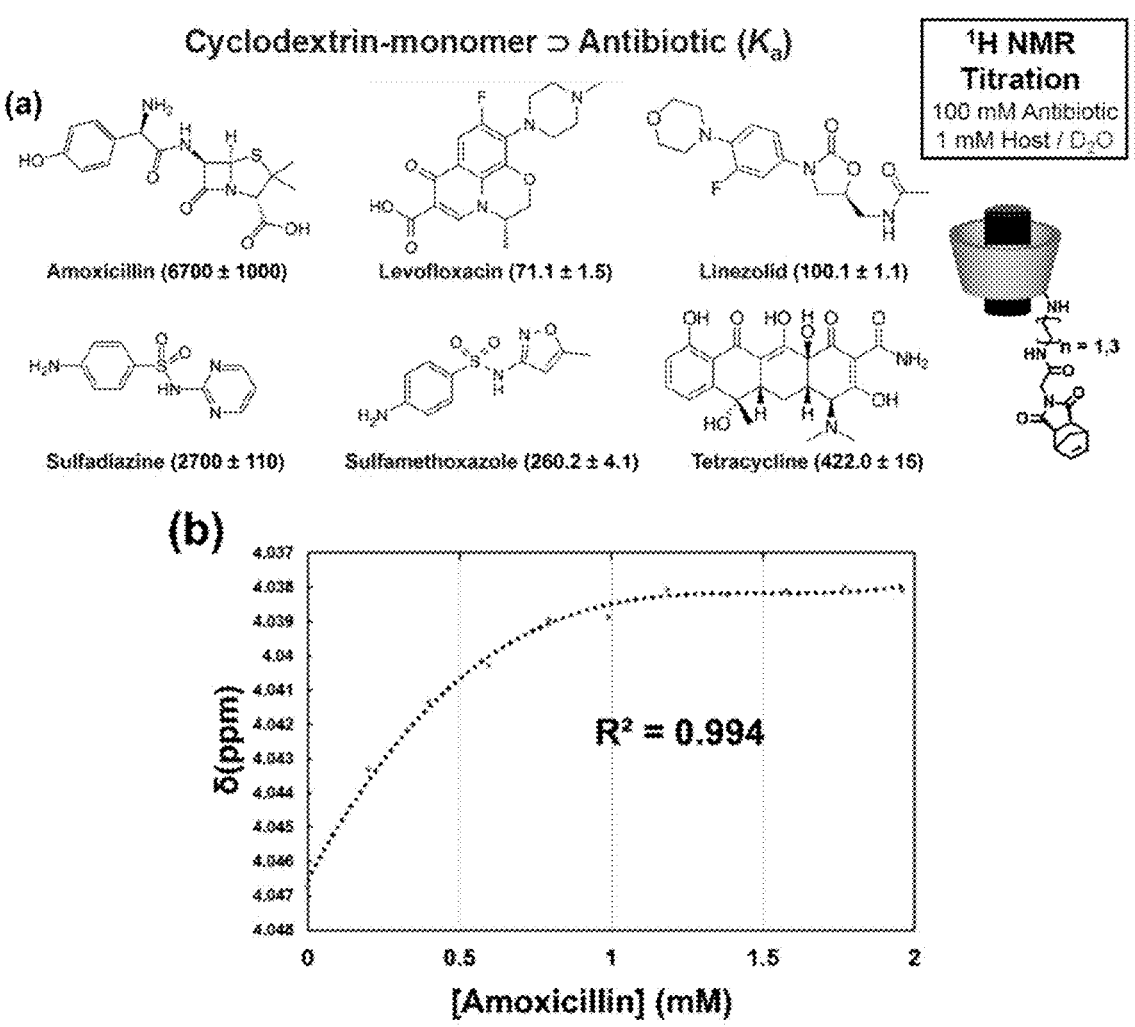
FIG. 8
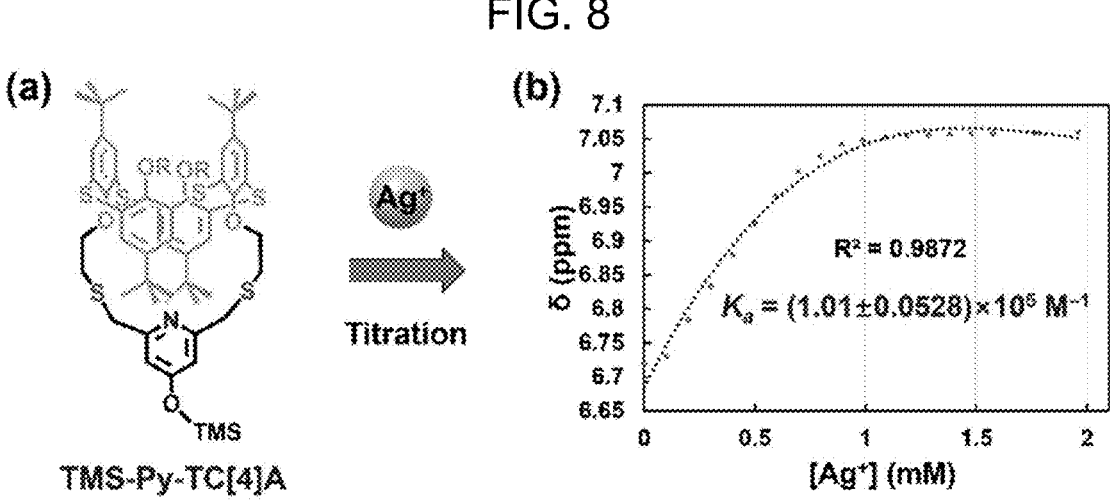

FIG. 24

Loading Ag⁺ and Amoxicillin Into Polymer-bound Receptors

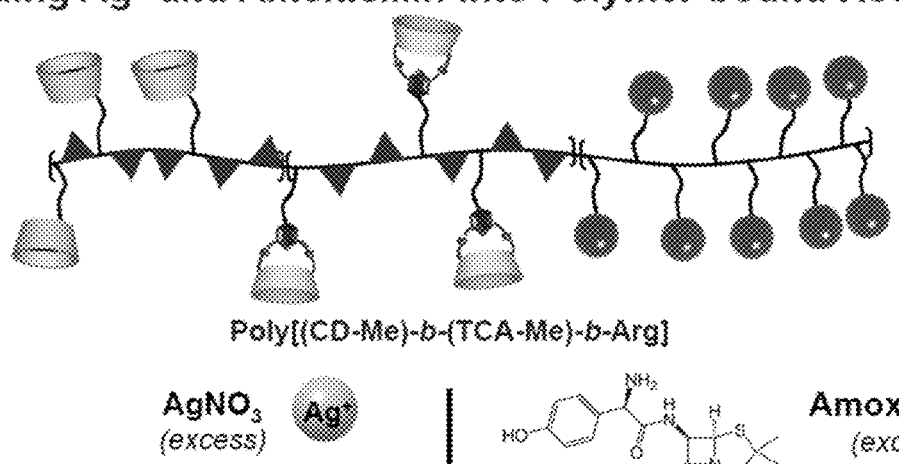

Poly[(CD-Me)-*b*-(TCA-Me)-*b*-Arg]

AgNO₃
(excess)   Ag⁺     Amoxicillin
(excess)

TFA | Deprotection

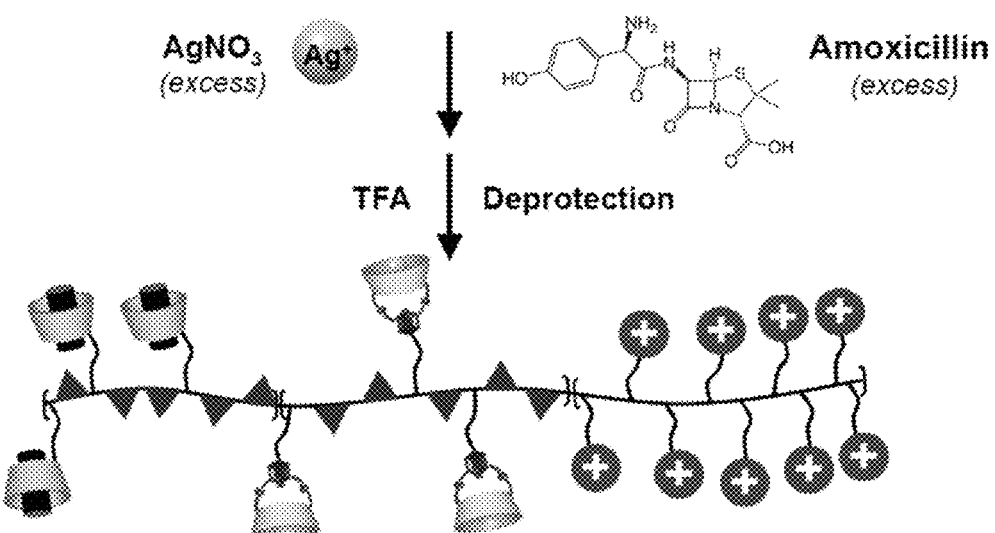

Poly[(CD-Me-Drug)-*b*-(TCA-Me-Ag⁺)-*b*-Arg²⁺]

FIG. 25

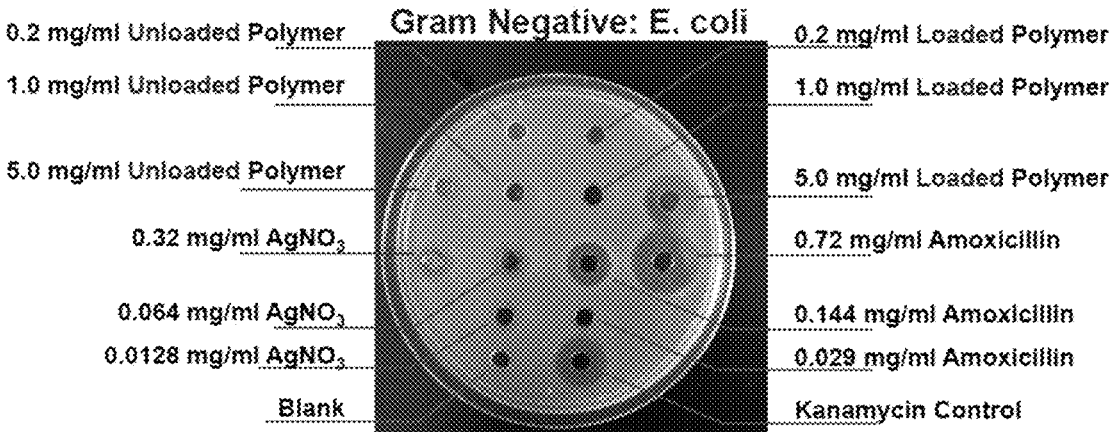

0.2 mg/ml Unloaded Polymer     Gram Negative: E. coli     0.2 mg/ml Loaded Polymer 1.0 mg/ml Unloaded Polymer     1.0 mg/ml Loaded Polymer 5.0 mg/ml Unloaded Polymer     5.0 mg/ml Loaded Polymer 0.32 mg/ml AgNO₃     0.72 mg/ml Amoxicillin 0.064 mg/ml AgNO₃     0.144 mg/ml Amoxicillin 0.0128 mg/ml AgNO₃     0.029 mg/ml Amoxicillin Blank     Kanamycin Control

FIG. 26

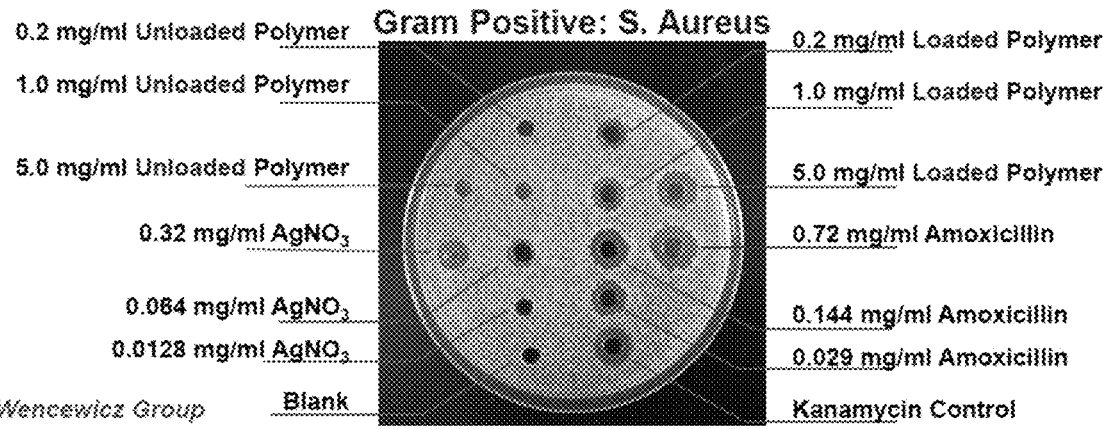

0.2 mg/ml Unloaded Polymer
1.0 mg/ml Unloaded Polymer
5.0 mg/ml Unloaded Polymer
0.32 mg/ml AgNO₃
0.084 mg/ml AgNO₃
0.0128 mg/ml AgNO₃
*Wencewicz Group*     Blank Gram Positive: S. Aureus 0.2 mg/ml Loaded Polymer
1.0 mg/ml Loaded Polymer
5.0 mg/ml Loaded Polymer
0.72 mg/ml Amoxicillin
0.144 mg/ml Amoxicillin
0.029 mg/ml Amoxicillin
Kanamycin Control

FIG. 27

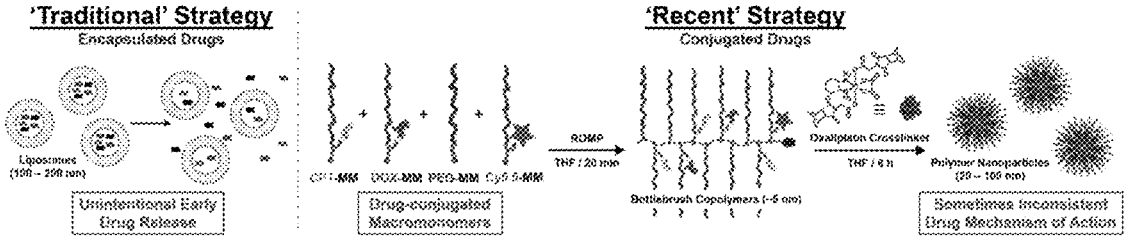

FIG. 28

Aim 1
Monomer Development

Aim 2
Copolymerization

Aim 3
Universal Combo Platform

1

COMPOSITIONS OF DRUG DELIVERY AGENTS AND METHODS OF USE THEREOF

CROSS-REFERENCE TO RELATED APPLICATIONS

This application claims priority from U.S. Provisional Application Ser. No. 62/649,735 filed on 29 Mar. 2018, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

Not applicable.

FIELD OF THE INVENTION

The present disclosure generally relates to methods and compositions for drug delivery in antibacterial and anticancer therapies.

BACKGROUND OF THE INVENTION

The Center for Disease Control and Prevention (CDC) estimates that each year over 2,000,000 reported cases of illnesses and 23,000 deaths are caused by antibiotic resistance in the United States (US). The World Health Organization (WHO) has identified antibiotic resistance as being one of the biggest threats to global health and food security. This urgent threat of multi-drug resistant (MDR) bacteria, combined with the fact that pharmaceutical companies have downsized their R&D efforts to pursue new antibiotics, has resulted in a broad-sweeping panic caused by the fear of a worldwide epidemic, a scenario which prompted the former Director-General of the WHO—Dr. Margaret Chan—to state that, "The world is heading towards a post-antibiotic era in which common infections will once again kill. [ . . . ] This may even bring the end of modern medicine as we know it."

The traditional approach to solve this growing problem typically relies on developing structural analogs of existing antibiotics, pursuing new leads, or perhaps revisiting previous compounds that were at one point considered extremely toxic. Combination therapy that combines multiple antibiotics into one treatment is also a common strategy to overcome resistance in bacteria; however, it can also be quite toxic. In recent years, these approaches have not only been outpaced by the onset of resistance, but the situation is exacerbated by the fact that the number one reason most antibiotics fail is due to a lack of solubility in water and their inability to permeate bacterial cell membranes.

Furthermore, treatments for aggressive and metastatic types of cancer often come in the form of "cocktails" that consist of multiple small-molecule anti-cancer drugs that are often administered multiple times intravenously over the course of a lengthy treatment regimen. One example of this combination-based strategy is FOLFIRINOX—consisting of Folinic acid, Fluorouracil, Irinotecan, and Oxaliplatin—which is often used to treat metastatic pancreatic cancer. Although it is an effective treatment capable of extending the median overall survival rate to 11.1 months, compared to only a few months with other single-drug-based systems, FOLFIRINOX is also incredibly toxic and may result in an increased rate of infection due to a drop in white blood cells, tiredness as a result of a lower red blood cell count, the formation of ulcers, hair loss, and so on. The drug delivery community has worked to develop systems capable of delivering anti-cancer drugs with improved pharmacokinetics and dramatically reduced toxicities; however, it remains a major challenge to construct platforms that can support the precise loading of three or more drugs without unintentional early release of drugs. Even more troubling, there are also now concerns emerging over how drugs that are conjugated directly to the delivery platform are not released completely and efficiently once inside the tumor, and even when they are released in vitro/vivo, their mode of action may be different than what is expected in comparison to the observed mechanisms of small-molecule free drugs. These major delivery issues can often perturb or completely derail clinical trials that investigate efficacy using modern drug delivery systems.

SUMMARY OF THE INVENTION

Among the various aspects of the present disclosure is the provision of compositions and methods related to drug-loaded nanoparticles comprising polymers (e.g., comprising various norbornene (Nb)-based monomers) used for the treatment of bacterial infections and or cancer.

An aspect of the present disclosure provides for a composition comprising a polymer-based drug-delivery agent, wherein the polymer-based drug-delivery agent comprises at least a first polymerized monomer and at least a second polymerized monomer; the first polymerized monomer comprises at least a first macrocyclic moiety and the second polymerized monomer comprises a second macrocyclic moiety; the first macrocyclic moiety is non-covalently bound or is capable of non-covalently binding a first antibiotic or a first anticancer agent; and/or the second macrocyclic moiety is non-covalently bound or is capable of non-covalently binding a second antibiotic, a second anticancer agent, an alkali metal cation, or a transition metal cation.

In some embodiments, a first macrocyclic moiety is non-covalently bound to a first antibiotic and the second macrocyclic moiety is non-covalently bound to a second antibiotic and the first antibiotic and the second antibiotic are not the same antibiotic.

In some embodiments, a first macrocyclic moiety is non-covalently bound to a first antibiotic and the second macrocyclic moiety is non-covalently bound to a an alkali metal cation or a transition metal cation.

In some embodiments, a first macrocyclic moiety is non-covalently bound to a first anticancer agent and the second macrocyclic moiety is non-covalently bound to a second antibiotic and the first anticancer agent and the second anticancer agent are not the same anticancer agent.

In some embodiments, a polymer-based drug-delivery agent comprises: a polymerized monomer comprising a protonatable subunit; a polymerized monomer comprising an imaging agent (NIR dye, contrast agent), a targeting group (e.g., folate to target breast cancer cells, peptide), or a binding group; a masked polymerization initiator, capable of being deprotected and initiating a polymerization; a glucosamine derivative; a norbornene group (e.g., a N-alkyl-5-exo-norbornene-2,3-dicarboxylic acid imide group); or a norbornene (Nb)-based hexaethylene glycol capped with an N-L-arginine-glucosamine subunit (Nb-LARGE monomer, Nb-Arg).

In some embodiments, the polymer-based drug-delivery agent is capable of self-assembly into a micelle.

In some embodiments, the composition comprises a non-covalent cross-linking group (e.g., adamantane-functionalized crosslinker, bis(adamantyl) crosslinker) capable of non-covalently binding two or more macrocyclic moieties.

In some embodiments, the first macrocyclic moiety is a cyclodextrin bound to an antibiotic and the second macrocyclic moiety is a calixarene bound to an $Ag^+$.

In some embodiments, the first macrocyclic moiety is a cyclodextrin bound to a first anticancer agent and the second macrocyclic moiety is a cyclodextrin bound to a second anticancer agent, wherein the first anticancer agent is not the same as the second anticancer agent.

In some embodiments, the polymer-based drug-delivery agent is easily protonated, targets a bacteria cell surface, or destabilizes cell membranes; is capable of self-assembly; exhibits a controlled and sustained delivery of a silver ion $(Ag^+)$ and one or more small-molecule antibiotic simultaneously; comprising $Ag^+$ induces oxidative stress in bacteria; comprising $Ag^+$ disrupts disulfide bond formation in proteins, resulting in an increase in permeability of their cellular membranes; or induces collagen synthesis during wound healing.

In some embodiments, the polymer-based drug-delivery agent comprises a polynorbornene backbone.

In some embodiments, the macrocyclic moiety comprises a hydrophobic cavity capable of binding a small molecule drug or alkali metal cations or transition metal cations with high affinity (e.g., for antibiotics or anticancer drugs, a $K_a$ of greater than about 100 $M^{-1}$ and for alkali metal cations or transition metal cations, a $K_a$ of greater than about $10^{2-5}$ $M^{-1}$).

In some embodiments, the first macrocyclic moiety or second macrocyclic moiety is independently selected from the group consisting of: a cyclodextrin; a β-cyclodextrin; a calixarene; a thiacalix[n]arene; a tert-butyl-thiacalix[4] arene; a cyclophane; a crown ether; and a [18]-crown-6 ether.

In some embodiments, the first anticancer agent and the second anticancer agent are independently selected from one or more of the group consisting of: camptothecin; doxorubicin; cisplatin; oxaliplatin; 5-fluoruracil; chlorambucil; methotrexate; and irinotecan HCl.

In some embodiments, the first antibiotic or the second antibiotic are independently selected from one or more of the group consisting of: a β-lactam; amoxicillin; imipenem; an aminoglycoside; a quinolone; a fluoroquinolone; Levofloxacin; chloramphenicol; a sulfonamide; Sulfadiazine, Sulfamethoxazole; tetracycline; linezolid; and a thiol NDM-1 inhibitor.

In some embodiments, the transition metal cation is selected from a copper $(Cu^{2+})$ ion or a silver $(Ag^+)$ ion.

In some embodiments, the polymer-based drug-delivery agent comprises: a PEG (e.g., a Nb-PEG-X monomer); a hexaethylene glycol capped with an N-L-arginine-glucosamine subunit (e.g., a Nb-LARGE monomer, Nb-Arg); a methyl (e.g., an Nb-Me monomer); or a norbornene (Nb)-based monomer.

In some embodiments, the first macrocyclic moiety or the second macrocyclic moiety is a calixarene comprising a thioether-pyridine bridge, wherein the thioether-pyridine bridge increases binding of the transition metal cation inside the calixarene compared to a calixarene without the thioether-pyridine bridge.

Another aspect of the present disclosure provides for a method of producing a polymer-based drug-delivery agent described herein, comprising: generating at least two monomers comprising a backbone and a first macrocyclic moiety and a second macrocyclic moiety; and polymerizing the monomers, wherein the first macrocyclic moiety and the second macrocyclic moiety are non-covalently bound to different therapeutic agents.

In some embodiments, the method comprises linking a targeting agent or imaging agent to the backbone.

In some embodiments, a polymerization is performed using a ratiometric ring-opening metathesis polymerization (ROMP) reaction; the ROMP reaction is conducted using Grubbs' third-generation ruthenium catalyst in non-polar tetrahydrofuran (THF) solvent; or a monomer has an active or 'living' ruthenium species on one end.

In some embodiments, the method comprises generating an amino-functionalized cyclodextrin comprising mono-to-sylating a cyclodextrin, resulting in a cyclodextrin with at least one tosyl group, nucleophilic displacement of the at least one tosyl group with ethylene diamine, resulting in an amino-functionalized cyclodextrin, wherein the amino-functionalized cyclodextrin is reacted with a norbornene-based acyl chloride, resulting in a norbornene-functionalized cyclodextrin.

In some embodiments, the method comprises generating a norborene-functionalized calixarene by generating a 1,2 calixarene conformer via a Mitsunobu reaction between a calixarene and a ortho-substituted norbornyl-pyridine with methylenethio ethanol linkers and functionalizing remaining tert-butyl phenol subunits of the calixarene ring with triethylene glycol monomethyl ether chains, resulting in improved solubility of a monomer in tetrahydrofuran (THF).

In some embodiments, the method comprises generating a tert-butyloxycarbonyl (Boc)-protected arginine monomer (Nb-Arg (Boc)) to serve as a precursor to a positively charged block of a functional copolymer.

In some embodiments, the method comprises generating a macromonomer consisting of poly(ethylene glycol) (PEG3000) bearing a norbornene group at one end (Nb-PEG).

In some embodiments, the method comprises initiating polymerization of a monomer comprising deprotecting a masked polymerization resulting in a three-dimensional polymer network.

Yet another aspect of the present disclosure provides for a method for treating a subject in need thereof comprising administration of an effective amount of a polymer-based drug-delivery agent to a patient in need thereof, wherein the polymer-based drug-delivery agent is loaded with a therapeutic agent and the subject has cancer, a bacterial infection, or a wound.

In some embodiments, subject has cancer, the cancer is selected from one or more of the group consisting of: pancreatic cancer, breast cancer, leukemia, lymphoma, ovarian cancer, and metastatic cancer;

In some embodiments, subject has a bacterial infection, the bacterial infection selected from or more of the group consisting of: gram-positive bacteria, gram-negative bacteria, multi-drug resistant-bacteria (MDR), methicillin-resistant *Staphylococcus aureus* (MRSA), *Pseudomonas aeruginosa, Escherichia coli*, or NDM-1 producing carbapenem-resistant Enterobacteriaceae.

In some embodiments, subject has a wound.

In some embodiments, cancer cells are targeted with a targeting agent; folate to target breast cancer cells; or peptides.

In some embodiments, anti-cancer drugs are released after administering the polymer-based drug-delivery agent to the subject.

Yet another aspect of the present disclosure provides for a device (e.g., a dual-syringe) used to treat hemorrhages and prevent bacterial infections of open wounds, wherein a first syringe delivers sodium alginate, which is a rapid hemostat; and/or a second syringe delivers the composition according to claim 1 (e.g., drug-loaded nanoparticles).

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1. Tetrablock copolymer synthesis and non-covalent crosslinking.

FIG. 2. Measuring $Ag^+$ and antibiotic binding in model diblock copolymers.

FIG. 4. The three phases for developing the combination antimicrobial/antibiotic platform are illustrated.

FIG. 5. The main classes of artificial hosts that have been synthesized and studied over the past half century.

FIG. 6. Monomer design and properties. The chemical structure of the three functional antimicrobial monomers.

FIG. 7. Cyclodextrin-monomer $\supset$ antibiotic. (A) The chemical structure of antibiotics that were evaluated as guests bound inside the cavity of the (n=3) Nb-CD monomer in water at 25° C. The values provided are the equilibrium affinity constant ($K_a$) at room temperature. (B) The binding titration curve illustrates saturation after one equivalent of amoxicillin is added to the Nb-CD host. Non-linear regression analysis was used to determine the $K_a$ values provided under each antibiotic structure.

FIG. 8. (A) Chemical structure of the precursor TMS-Py-TC[4]A and (B) its 1H NMR-based titration curve after addition of $Ag^+$ in THF-d8 at 25° C. (500 MHz).

FIG. 24. Loading $Ag^+$ and amoxicillin into polymer-bound receptors.

FIG. 25. Gram-negative: *E. coli*. In vitro efficacy against bacterial clinical isolates.

FIG. 26. Gram-positive: *S. Aureus*. In vitro efficacy against bacterial clinical isolates.

FIG. 27. A comparison of a 'traditional' drug delivery strategy with liposomes versus a 'recent' drug-conjugated approach that was previously carried out. Liposomes can result in early release, and prodrugs can have different mechanism of actions (MOAs).

FIG. 28. A visual abstract for the three aims employing a supramacromolecular approach to non-toxic combination anti-cancer therapeutics.

DETAILED DESCRIPTION OF THE INVENTION

Figure 3:
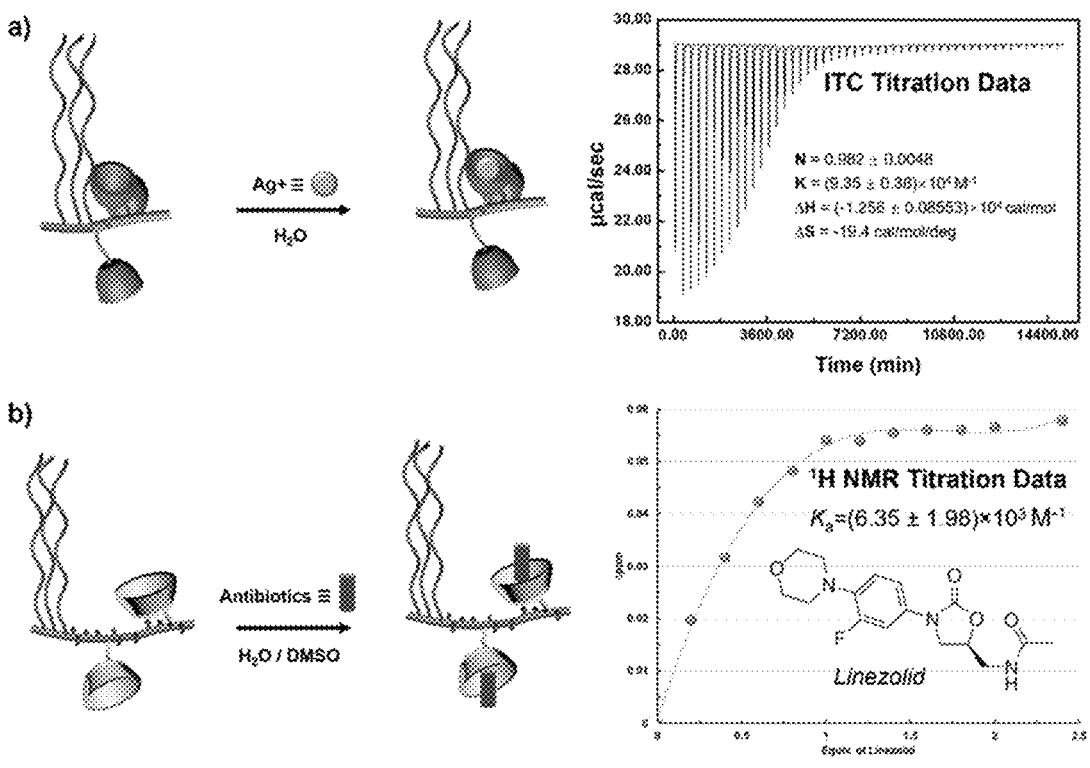
FIG. 3. Rate of release of $Ag^+$ from tetrablock copolymer and nanoparticle.

The present disclosure is based, at least in part, on the discovery that a polymer-based drug-delivery agent (e.g., nanoparticles constructed from norbornene (Nb)-based monomers) can be used for the delivery of drugs (or therapeutic agents) and small molecules to, for example, treat multidrug resistant bacteria or aggressive forms of cancer. Another application can be for agriculture seed coatings for protection and seedling growth.

Described herein is a next-generation universal plug-and-play drug delivery system comprised of linked supramolecular monomers that can act as 'smart' receptors for a wide variety of small-molecule therapeutics, such as anti-cancer or anti-bacterial drugs that can be polymerized together in precise monomer ratios to yield combination drug-loaded nanoparticles. This 'supramacromolecular' approach can completely bypass any issues associated with prodrug-to-drug conversion in vitro/vivo because the unmodified drug itself will be what is loaded into the receptors that are positioned along the polymer chain, and therefore the drug's mechanism of action will remain undistorted. Additionally, the small-molecule drugs will not need an external event in vitro/vivo to trigger their release from the platform, but rather the release will be governed by the non-covalent binding interactions between the receptor and the drug.

The difference between previous studies and the presently disclosed invention relates specifically to the method or manner in which the drugs and metal ions are incorporated into the polymer-based platform. Previous studies employed a method of physically (covalently) attaching the drugs to the monomer prior to polymerization and then relied on natural enzymes in an organism to cleave the covalent bonds and release the drugs. The presently disclosed approach does not chemically modify the drugs, but instead loads the free drug form into receptors that bind the drug or metal ion temporarily and slowly releases them over time. This distinction is significant because many drug-conjugated monomers and polymers often fail to release their cargo in vivo, and for some of the ones that do, they sometimes lose their original mechanism of action in the site of release (e.g., the site of infection).

Here is described the synthesis of supramolecular monomers and polymers. Also demonstrated is that supramolecular monomers and polymers can bind a wide variety of antibacterial and anticancer drugs and a metal ion e.g., silver ($Ag^+$). Described herein is in vitro efficacy data showing that the drug-loaded polymer platform can kill bacteria and inhibit further growth over time (see e.g., Example 4).

The present disclosure provides for a universal platform for the delivery of any combination of small-molecule drugs. Usually small-molecule drugs are not water-soluble and/or are toxic, the latter of which is especially true when used in drug cocktails consisting of multiple drugs, which is the current practice employed in the clinic for both multi-drug-resistant (MDR) bacterial infections and aggressive forms of cancer. The significance of the presently disclosed system is that it is not necessary to remake a new polymer to deliver different combinations of drugs. Here, one would simply choose the desired drug combination and precise ratio and add it to the disclosed polymers. The resultant drug-loaded polymers could then be used as a broad-spectrum antimicrobial that could be used as a broad-spectrum treatment against MDR bacterial infections or as a non-toxic chemotherapy for treatment of aggressive forms of cancer. Furthermore, the selective capture and slow release of small-molecule drugs or nutrients are ideal for agricultural applications, such as seed coatings for protection and seedling growth.

Overcoming Antibiotic Resistance

The present disclosure provides for compositions and methods for overcoming antibiotic resistance. The Center for Disease Control and Prevention (CDC) estimates that each year over 2,000,000 reported cases of illnesses and 23,000 deaths are caused by antibiotic resistance in the United States (US).

The continual rise of antibiotic resistance—coupled with the shrinking pipeline of new antibiotics—poses a major threat to global health. The traditional approach to solve this growing problem typically relies on developing structural analogs of existing antibiotics, pursuing new leads, or even revisiting previous compounds that were at one point considered very toxic. Combination therapy that combines multiple small-molecule antibiotics into one treatment is also a common strategy to overcome resistance in bacteria, however, it can also be quite toxic. In recent years, these approaches have not only been outpaced by the onset of resistance, but the situation is exacerbated by the fact that the number one reason most antibiotics fail is due to a lack of solubility in water and their inability to permeate bacterial cell membranes. Here is described a different strategy; one which involves precise supramolecular receptors built into a polymer platform, where each receptor can be loaded with different combinations of antimicrobial agents, depending on the type of multidrug-resistant bacteria that is to be treated. Moreover, this platform is easily converted into larger nano-based structures, which stabilize the loaded drugs and allows for selective targeting of bacteria through specific cell surface-based interactions. Since no pro-drugs are involved, the mechanism of action of each agent is unperturbed and each undergoes slow release in a predictable manner. Lastly, described herein, are in vivo efficacy studies against different drug-resistant bacterial strains, and how this next-generation platform is an ideal material for sustained protection that may prove useful in wound healing applications, among others.

In 2013, at least 2,049,442 estimated minimum number of illnesses and 23,000 deaths caused by antibiotic resistance. Decreased pharma pipeline leads to a shortage of new antimicrobials. Misuse of current antimicrobials has resulted in an increase in resistant strains of bacteria.

It is well-known that silver can be used as an antimicrobial, such as $Ag^+$-based Nanomaterials (Richter, 2015), Potentiating Antibiotics with $Ag^+$ (Morones, 2013), Disruption of Quorum Sensing Signalling (McGivney, 2018).

The World Health Organization (WHO) has identified antibiotic resistance as being one of the biggest threats to global health and food security. This urgent threat of multidrug-resistant (MDR) bacteria, combined with the fact that pharmaceutical companies have downsized their R&D efforts to pursue new antibiotics, has resulted in a broad-sweeping panic caused by the fear of a worldwide epidemic, a scenario which prompted the former Director-General of the WHO—Dr. Margaret Chan—to state that, "The world is heading towards a post-antibiotic era in which common infections will once again kill. [ . . . ] This may even bring the end of modern medicine as we know it."

Drug resistant bacteria have existed since the early 1940's, appearing shortly after penicillin and streptomycin were widely distributed to treat bacterial infections in hospitals and those associated with trauma injuries or surgical wounds during World War II. In the decades that followed, the spread of drug resistant bacteria was mitigated, in large part, by the identification and isolation of many other classes of antibiotics. In the absence of newly developed antibiotics over time, drug-related selective pressures have allowed bacteria to develop resistance, especially when the existing antibiotics are not properly prescribed to patients, are not used for the full duration of the prescribed amount, or are used in food-producing livestock to promote animal growth. The fact that drug resistance in bacteria is only a matter of time due to the persistence of some small population of bacterial cells after treatment—even with the proper use of antibiotics—many pharmaceutical companies have downsized their efforts to develop new antibiotics since the cost begins to outweigh the benefits. As a direct consequence of this pipeline shortage, more and more strains of bacteria are becoming resistant to one or more drugs, and in some cases, can require 6-7 drugs for a single infection in order to serve as an effective treatment. This trend results in a continual rise in the number of hospital-acquired (HA-) and community-acquired multidrug-resistant (CA-MDR) bacterial infections every year, which leads to $20 billion per year in excess health care costs and $35 billion per year in societal costs in the U.S. Even with an overall decrease in methicillin-resistant *Staphylococcus aureus* (MRSA) infections in hospital settings from 2005 to 2011, the number of people that die from MRSA infection in U.S. hospitals is more than the combined total of those suffering from HIV/AIDS and tuberculosis. Furthermore, over 2 million people in the U.S. in the year 2013 suffered from illnesses related to antibiotic resistant microbes, where approximately 23,000 of these cases ultimately proved to be fatal.

To curb these disturbing trends, either new antibiotics need to be discovered or alternative strategies need to be explored that can repurpose old antibiotics. Silver has long been known to behave as a broad-spectrum antimicrobial, and there is a substantial literature footprint describing silver nanoparticles (AgNPs) and their ability to leach silver ions (Ag$^+$) and kill Gram-negative *Escherichia coli* (*E. coli*), *Pseudomonas aeruginosa* (*P. aeruginosa*), and even antibiotic-resistant strains of bacteria. One issue associated with AgNP therapies is the lack of complete consumption of the nanoparticles during treatment, which may lead to an increase in antibiotic resistance, even potentially acquired resistance to drugs that do not contain silver. Collins and co-workers showed recently how sub-lethal concentrations of Ag$^+$ can serve as a chemical primer to induce oxidative stress in bacteria and can also disrupt disulfide bond formation in proteins, resulting in an increase in permeability of their cellular membranes. When the sub-lethal concentration of Ag$^+$ was used in a synergistic ratio with known antibiotics, resistant strains suddenly became susceptible again to antibiotics at minimum inhibitory concentrations (MIC) comparable to non-resistant strains. Even though this work is a beautiful investigation into the in vitro and in vivo efficacy employing Ag$^+$, the method of delivery consisted of a formulation, or "cocktail," injected into the peritoneal cavity, which allows the silver and antibiotics to be distributed throughout the body. This led to the development of mild liver damage during the first 48 hours of treatment, more than likely the result of using a concentration of antimicrobials greater than what is actually needed to treat the infection.

Conventional approaches for solving the growing problem of antibiotic resistance typically relies on developing structural analogs of existing antibiotics, pursuing new leads, or revisiting previous compounds that were at one point considered extremely toxic. Combination therapy that combines multiple antibiotics into one treatment can also be a strategy to overcome resistance in bacteria, however, it can also be quite toxic. In recent years, these approaches have not only been outpaced by the onset of resistance, but the situation is exacerbated by the fact that the number one reason most antibiotics fail is due to a lack of solubility in water and their inability to permeate bacterial cell membranes.

Described herein, is a completely different strategy; one which capitalizes on a versatile non-toxic multi-component polymer-based platform that can i) selectively target bacteria, ii) destabilize its membrane, and iii) exhibit well-controlled and sustained delivery of the combination of silver ions (Ag$^+$) and multiple (e.g., two or three or more) small-molecule antibiotics simultaneously from a single platform.

This supramacromolecular approach to drug delivery is highly innovative because it involves the design of two 'smart' supramolecular receptors that are built into the polymer-based platform and are tuned to selectively bind (and slowly release) precise ratios of Ag$^+$ alongside a wide variety of solubilized small-molecule antibiotics. Since the combination of Ag$^+$ and antibiotics has been shown to result in lower rates of antibiotic resistance in bacteria, any 'old' or once ineffective small-molecule antibiotics can be reinstated and easily delivered using the disclosed 'plug-and-play' platform. As a bonus, the electrostatic targeting agent that is described here, as the third monomer is also known to disrupt biofilms and promote collagen synthesis, two properties that are ideal for post-surgical wound healing or battlefield applications.

As described herein, the polymer-based drug delivery agent can incorporate an antibiotic or multiple antibiotics simultaneously. For example, the antibiotic or multiple antibiotics can be selected from the classes of a penicillin, a tetracycline, a cephalosporin, a quinolone, a lincomycin, a macrolide, a sulfonamide, a glycopeptide, an aminoglycoside, or a carbapenem.

As another example, the antibiotic or multiple antibiotics can be selected from amoxicillin, doxycycline, cephalexin, ciprofloxacin, clindamycin, metronidazole, azithromycin, sulfamethoxazole/trimethoprim, amoxicillin/clavulanate, or levofloxacin. As another example, the antibiotic or multiple antibiotics can be selected from vancomycin, trimethoprim/sulfamethoxazole, doxycycline, ceftobiprole, ceftaroline, clindamycin, dalbavancin, daptomycin, fusidic acid, linezolid, mupirocin (topical), omadacycline, oritavancin, tedizolid, telavancin, tigecycline, aminoglycosides, carbapenems, ceftazidime, cefepime, ceftobiprole, ceftolozane/tazobactam, fluoroquinolones, piperacillin/tazobactam, ticarcillin/clavulanic acid, linezolid, streptogramins, tigecycline, or daptomycin, or any antibiotic listed in TABLE 1 or TABLE 2. As another example, the antibiotic or multiple antibiotics can be selected from Augmentin™, Flagyl™, Flagyl ER™, Amoxil™, Cipro™, Keflex™, Bactrim™, Bactrim DS™, Levaquin™ Zithromax™, Avelox™, or Cleocin™.

TABLE 1

| Antibiotics by class. | | | | |
| --- | --- | --- | --- | --- |
| Generic name | Brand names | Common uses | Possible side effects | Mechanism of action |
| Aminoglycosides | | | | |
| Amikacin | Amikin ™ | Infections caused by Gram-negative bacteria, such as *Escherichia coli* and *Klebsiella* | Hearing loss | Binding to the bacterial 30S ribosomal subunit |
| Gentamicin | Garamycin ™ | | Vertigo | |
| Kanamycin | Kantrex ™ | | Kidney damage | |

TABLE 1-continued

| | | | | |
|---|---|---|---|---|
| | | | Possible | Mechanism |
| Generic name | Brand names | Common uses | side effects | of action |

<div align="center">Antibiotics by class.</div>

| Generic name | Brand names | Common uses | Possible side effects | Mechanism of action |
|---|---|---|---|---|
| Neomycin<br>Netilmicin<br>Tobramycin<br>Paromomycin | Neo-Fradin ™<br>Netromycin ™<br>Nebcin ™<br>Humatin ™ | particularly<br>*Pseudomonas*<br>*aeruginosa.*<br>Effective against<br>aerobic bacteria<br>(not<br>obligate/facultative<br>anaerobes) and<br>tularemia. All<br>aminoglycosides<br>are ineffective<br>when taken orally<br>as the stomach<br>will digest the drug<br>before it goes into<br>the bloodstream.<br>However<br>aminoglycosides<br>are effective in<br>Intravenous,<br>intramuscular and<br>topical forms. | | (some work<br>by binding<br>to the 50S<br>subunit),<br>inhibiting the<br>translocation<br>of the<br>peptidyl-<br>tRNA from<br>the A-site to<br>the P-site<br>and also<br>causing<br>misreading<br>of mRNA,<br>leaving the<br>bacterium<br>unable to<br>synthesize<br>proteins vital<br>to its growth. |
| Streptomycin<br>Spectinomycin(Bs) | Trobicin ™ | Tuberculosis<br>Gonorrhea | | |

<div align="center">Ansamycins</div>

| Geldanamycin<br>Herbimycin | | Experimental, as<br>antitumor<br>antibiotics | | Block DNA<br>transcription,<br>either via |
|---|---|---|---|---|
| Rifaximin | Xifaxan ™ | Traveler's<br>diarrhea caused<br>by *E. coli* | | inhibiting<br>DNA-<br>dependent<br>RNA<br>polymerase<br>by binding<br>to the β-<br>subunit |

<div align="center">Carbacephem</div>

| Loracarbef | Lorabid ™ | Discontinued | | Prevents<br>bacterial cell<br>division by<br>inhibiting<br>cell wall<br>synthesis. |
|---|---|---|---|---|

<div align="center">Carbapenems</div>

| Ertapenem | Invanz ™ | Bactericidal for<br>both Gram-<br>positive and<br>Gram-negative<br>organisms and | Gastrointes<br>tinal upset<br>and<br>diarrhea<br>Nausea | Inhibition of<br>cell wall<br>synthesis |
|---|---|---|---|---|
| Doripenem<br>Imipenem/Cilastatin<br>Meropenem | Doribax ™<br>Primaxin ™<br>Merrem ™ | therefore useful<br>for empiric broad-<br>spectrum<br>antibacterial<br>coverage. (Notes:<br>MRSA resistance<br>to this class. All<br>are active against<br>*Pseudomonas*<br>*aeruginosa* except<br>ertapenem.) | Seizures<br>Headache<br>Rash and<br>allergic<br>reactions | |

<div align="center">Cephalosporins (First generation)</div>

| Cefadroxil | Duricef ™ | Good coverage<br>against Gram-<br>positive infections. | Gastrointes<br>tinal upset<br>and<br>diarrhea | Same mode<br>of action as<br>other beta-<br>lactam |
|---|---|---|---|---|

TABLE 1-continued

| Generic name | Brand names | Common uses | Possible side effects | Mechanism of action |
|---|---|---|---|---|
| Cefazolin | Ancef ™, | | Nausea (if alcohol taken concurrently) | antibiotics: disrupt the synthesis of the |
| | Kefzol ™ | | Allergic reactions | peptidoglycan layer of bacterial cell walls. |
| Cephradine Cephapirin Cephalothin Cefalexin | Keflex ™ | | | |
| Cephalosporins (Second generation) | | | | |
| Cefaclor | Distaclor ™, Ceclor ™, Raniclor ™ | Less Gram-positive cover, improved Gram-negative cover. | Gastrointes tinal upset and diarrhea | Same mode of action as other beta-lactam |
| Cefoxitin | | | Nausea (if alcohol taken concurrently)- if contains methylthiot etrazole side group | antibiotics: disrupt the synthesis of the peptidoglycan layer of bacterial cell walls. |
| Cefotetan | Ceftan ™ | | Hypoprothr ombinemia- if contains methylthiot etrazole side group | |
| Cefamandole | | | Allergic reactions | |
| Cefmetazole Cefonicid Loracarbef Cefprozil | Cefzil ™ | | | |
| Cefuroxime | Ceftin ™, Zinnat ™ (UK) | | | |
| Cephalosporins (Third generation) | | | | |
| Cefixime (antagonistic with Chloramphenicol) | Cefspan ™ (Fujisawa), | Improved coverage of Gram-negative organisms, except *Pseudomonas*. | Gastrointes tinal upset and diarrhea | Same mode of action as other beta-lactam |
| | Suprax ™ | Reduced Gram-positive cover. But still not cover | Nausea (if alcohol taken concurrently) | antibiotics: disrupt the synthesis of the |
| Cefdinir | Omnicef ™, Cefdiel ™ | *Mycoplasma* and *Chlamydia* | Allergic reactions | peptidoglycan layer of |
| Cefditoren | Spectracef ™, Meiact ™ | | | bacterial cell walls. |
| Cefoperazone [Unlike most third-generation agents, cefoperazone is active against *Pseudomonas aeruginosa*], combination Cefoperazone with Sulbactam makes more effective antibiotic, because Sulbactam avoid degeneration of Cefoperazone | Cefobid ™ (discontinued) | | | |
| Cefotaxime | Claforan ™ | | | |
| Cefpodoxime | Vantin ™, Banadoz ™ | | | |

TABLE 1-continued

| | | | | |
|---|---|---|---|---|
| Antibiotics by class. | | | | |
| Generic name | Brand names | Common uses | Possible side effects | Mechanism of action |
| Ceftazidime (Unlike most third-generation agents, ceftazidime is active against *Pseudomonas aeruginosa*, but less active against *Staphylococci* and *Streptococci* compare to other 3rd generation of cephalosporins) | Fortaz ™, Ceptaz ™ | | | |
| Ceftibuten Ceftizoxime Moxalactam | Cedax ™ | | | |
| Ceftriaxone (IV and IM, not orally, effective also for syphilis and uncomplicated gonorrhea) | Rocephin ™ | | | |
| Cephalosporins (Fourth generation) | | | | |
| Cefepime | Maxipime ™ | Covers pseudomonal infections. | Gastrointes tinal upset and diarrhea Nausea (if alcohol taken concurrently) Allergic reactions | Same mode of action as other beta-lactam antibiotics: disrupt the synthesis of the peptidoglycan layer of bacterial cell walls. |
| Cephalosporins (Fifth generation) | | | | |
| Ceftaroline fosamil | Teflaro ™ | Used to treat MRSA | Gastrointes tinal upset and diarrhea Allergic reaction | Same mode of action as other beta-lactam antibiotics: disrupt the synthesis of the peptidoglycan layer of bacterial cell walls. |
| Ceftobiprole | Zeftera ™ | Used to treat MRSA (methicillin-resistant *Staphylococcus aureus*), penicillin-resistant *Streptococcus pneumoniae*, *Pseudomonas aeruginosa*, and enterococci | Gastrointes tinal upset and diarrhea Nausea (if alcohol taken concurrently) Allergic reactions | Same mode of action as other beta-lactam antibiotics: disrupt the synthesis of the peptidoglycan layer of bacterial cell walls. |
| Glycopeptides | | | | |
| Teicoplanin | Targocid ™ (UK) | Active against aerobic and anaerobic Gram-positive bacteria including MRSA; Vancomycin is used orally for the treatment of *C. difficile* colitis | | Inhibits peptidoglycan synthesis. |
| Vancomycin | Vancocin ™ | | | |
| Telavancin | Vibativ ™ | | | |
| Dalbavancin | Dalvance ™ | | | |
| Oritavancin | Orbactiv ™ | | | |

TABLE 1-continued

| Generic name | Brand names | Common uses | Possible side effects | Mechanism of action |
|---|---|---|---|---|
| | | Lincosamides(Bs) | | |
| Clindamycin Lincomycin | Cleocin ™ Lincocin ™ | Serious staph-, pneumo-, and streptococcal infections in penicillin-allergic patients, also anaerobic infections; clindamycin topically for acne Lipopeptide | Possible C. difficile-related pseudome mbranous enterocolitis | Binds to 50S subunit of bacterial ribosomal RNA thereby inhibiting protein synthesis. |
| Daptomycin | Cubicin ™ | Gram-positive organisms, but is inhibited by pulmonary surfactant so less effective against pneumonias | | Binds to the membrane and cause rapid depolarization, resulting in a loss of membrane potential leading to inhibition of protein, DNA and RNA synthesis. |
| | | Macrolides(Bs) | | |
| Azithromycin | Zithromax ™, Sumamed ™, Xithrone ™ | Streptococcal infections, syphilis, upper respiratory tract infections, lower respiratory tract infections, mycoplasmal infections, Lyme disease | Nausea, vomiting, and diarrhea (especially at higher doses) | Inhibition of bacterial protein biosynthesis by binding reversibly to the subunit 50S of the bacterial ribosome, thereby inhibiting translocation of peptidyl tRNA. |
| Clarithromycin | Biaxin ™ | | Prolonged cardiac QT interval (especially erythromycin) Hearing loss (especially at higher doses) | |
| Erythromycin | Erythocin ™, Erythroped ™ | | Jaundice | |
| Roxithromycin | | | | |
| Telithromycin | Ketek ™ | Pneumonia | Visual Disturbance, Liver Toxicity. | |
| Spiramycin | Rovamycine ™ | Mouth infections | | |
| Fidaxomicin | Dificid ™ | Treatment of Clostridioides (formerly Clostridium) difficile infection. May be more narrow-spectrum than vancomycin, resulting in less bowel microbiota alteration. | Nausea (11%), vomiting, and abdominal pain. | Bactericidal in susceptible organisms such as C. difficile by inhibiting RNA polymerase, thereby inhibiting protein synthesis. |
| | | Monobactams | | |
| Aztreonam | Azactam ™ | Gram-negative bacteria | | Same mode of action as other beta-lactam |

TABLE 1-continued

Antibiotics by class.

| Generic name | Brand names | Common uses | Possible side effects | Mechanism of action |
|---|---|---|---|---|
| | | | | antibiotics: disrupt the synthesis of the peptidoglycan layer of bacterial cell walls. |
| Nitrofurans | | | | |
| Furazolidone | Furoxone ™ | Bacterial or protozoal diarrhea or enteritis | | |
| Nitrofurantoin(Bs) | Macrodantin ™, Macrobid ™ | Urinary tract infections | | |
| Oxazolidinones(Bs) | | | | |
| Linezolid | Zyvox ™ | VRSA | Thrombo-cytopenia Peripheral neuropathy Serotonin Syndrome | Protein synthesis inhibitor; prevents the initiation step |
| Posizolid | Phase II clinical trials | | | |
| Radezolid | Phase II clinical trials | | | |
| Torezolid | Sivextro ™ | | | |
| Penicillins | | | | |
| Amoxicillin | Novamox ™, Amoxil ™ | Wide range of infections; penicillin used for streptococcal infections, syphilis, and Lyme disease | Gastrointes tinal upset and diarrhea | Same mode of action as other beta-lactam |
| Ampicillin | Principen ™ (discontinued) | | Allergy with serious anaphylactic reactions | antibiotics: disrupt the synthesis of the |
| Azlocillin | | | Brain and kidney damage (rare) | peptidoglycan layer of bacterial cell walls. |
| Dicloxacillin | Dynapen ™ (discontinued) | | | |
| Flucloxacillin | Floxapen ™ (Sold to European generics Actavis Group) | | | |
| Mezlocillin | Mezlin ™ (discontinued) | | | |
| Methicillin | Staphcillin ™ (discontinued) | | | |
| Nafcillin | Unipen ™ (discontinued) | | | |
| Oxacillin | Prostaphlin ™ (discontinued) | | | |
| Penicillin G | Pentids ™ (discontinued) | | | |
| Penicillin V | Veetids ™ (Pen-Vee-K) (discontinued) | | | |
| Piperacillin | Pipracil ™ (discontinued) | | | |
| Penicillin G | Pfizerpen ™ | | | |
| Temocillin | Negaban ™ (UK) (discontinued) | | | |
| Ticarcillin | Ticar ™ (discontinued) | | | |

TABLE 1-continued

| Antibiotics by class. | | | | |
| --- | --- | --- | --- | --- |
| Generic name | Brand names | Common uses | Possible side effects | Mechanism of action |
| Penicillin combinations | | | | |
| Amoxicillin/clavulanate | Augmentin ™ | Both Amoxicillin/ clavulanate and Ampicillin/ sulbactam are effective against non-recurrent acute otitis media. Amoxicillin/ clavulanate is one of the few oral antibiotics effective against skin and soft tissue infections. Can be given to children less than 40 kilograms in weight; for children heavier, the dosage is same as adults, twice daily. | | The second component reduces the effectivenes s of some forms of bacterial resistance to the first component |
| Ampicillin/sulbactam | Unasyn ™ | | | |
| Piperacillin/tazobactam | Zosyn ™ | | | |
| Ticarcillin/clavulanate | Timentin ™ | | | |
| Polypeptides | | | | |
| Bacitracin | | Eye, ear or bladder infections; usually applied directly to the eye or inhaled into the lungs; rarely given by injection, although the use of intravenous colistin is experiencing a resurgence due to the emergence of multi drug resistant organisms. | Kidney and nerve damage (when given by injection) | Inhibits isoprenyl pyro- phosphate, a molecule that carries the building blocks of the peptidoglycan bacterial cell wall outside of the inner membrane |
| Colistin | Coly-Mycin-S ™ | | | Interact with the Gram- negative bacterial outer membrane and cytoplasmic membrane, displacing bacterial counterions, which destabilizes the outer membrane. Act like a detergent against the cytoplasmic membrane, which alters its permeability. Polymyxin B and E are bactericidal even in an isosmotic solution. |
| Polymyxin B | | | | |

TABLE 1-continued

| Generic name | Brand names | Common uses | Possible side effects | Mechanism of action |
|---|---|---|---|---|
| | | Antibiotics by class. | | |
| | | Quinolones/Fluoroquinolones | | |
| Ciprofloxacin | Cipro ™, Ciproxin ™, Ciprobay ™ | Urinary tract infections, bacterial | Nausea (rare), irreversible | Inhibits the bacterial DNA gyrase |
| Enoxacin | Penetrex ™ | prostatitis, | damage to | or the |
| Gatifloxacin | Tequin ™ | community- | central | topoisomera |
| Gemifloxacin | Factive ™ | acquired | nervous | se IV |
| Levofloxacin | Levaquin ™ | pneumonia, | system | enzyme, |
| Lomefloxacin | Maxaquin ™ | bacterial diarrhea, | (uncommon), | thereby |
| Moxifloxacin | Avelox ™ | mycoplasmal | tendinosis | inhibiting |
| Nadifloxacin | | infections, | (rare) | DNA |
| Nalidixic acid | NegGram ™ | gonorrhea | | replication |
| Norfloxacin | Noroxin ™ | | | and |
| Ofloxacin | Floxin ™ (discontinued), Ocuflox ™ | | | transcription |
| Trovafloxacin | Trovan ™ | Withdrawn | | |
| Grepafloxacin | Raxar ™ | Withdrawn | | |
| Sparfloxacin | Zagam ™ | Withdrawn | | |
| Temafloxacin | Omniflox ™ | Withdrawn | | |
| | | Sulfonamides(Bs) | | |
| Mafenide | Sulfamylon ™ | Urinary tract infections (except sulfacetamide, used for eye | Nausea, vomiting, and diarrhea | Folate synthesis inhibition. They are |
| Sulfacetamide | Sulamyd ™, Bleph-10 ™ | infections, and mafenide and silver sulfadiazine, used topically for | Allergy (including skin rashes) | competitive inhibitors of the enzyme dihydro- |
| Sulfadiazine | Micro-Sulfon ™ | burns) | Crystals in urine | pteroate synthetase, |
| Silver sulfadiazine | Silvadene ™ | | Kidney failure | DHPS. DHPS catalyses |
| Sulfadimethoxine | Di-Methox ™ Albon ™ | | Decrease in white blood cell count | the conversion of PABA |
| Sulfamethizole | Thiosulfil Forte ™ | | Sensitivity to sunlight | (para-aminobenzo- |
| Sulfamethoxazole | Gantano ™ | | | ate) to |
| Sulfanilimide (archaic) | | | | dihy- |
| Sulfasalazine | Azulfidine ™ | | | dropteroate, a |
| Sulfisoxazole | Gantrisin ™ | | | key step in |
| Trimethoprim-Sulfamethoxazole (Co-trimoxazole) (TMP-SMX) | Bactrim ™ Septra ™ | | | folate synthesis. Folate is necessary for the cell to synthesize nucleic acids (nucleic acids are essential building blocks of DNA and RNA), and in its absence cells cannot divide. |
| Sulfonamidochrysoidine (archaic) | Prontosil ™ | | | |

TABLE 1-continued

| Generic name | Brand names | Common uses | Possible side effects | Mechanism of action |
|---|---|---|---|---|
| Antibiotics by class. | | | | |
| Tetracyclines(Bs) | | | | |
| Demeclocycline | Declomycin ™ | Syphilis, chlamydial | Gastrointestinal upset | Inhibits the binding of |
| Doxycycline | Vibramycin ™ | infections, Lyme disease, | Sensitivity to sunlight | aminoacyl-tRNA to the |
| Metacycline | | mycoplasmal infections, acne rickettsial infections, malaria | Potential toxicity to mother and fetus during pregnancy | mRNA-ribosome complex. They do so mainly by |
| Minocycline | Minocin ™ | | Enamel hypoplasia (staining of teeth; potentially permanent) | binding to the 30S ribosomal subunit in the mRNA translation |
| Oxytetracycline | Terramycin ™ | | Transient depression of bone growth | complex. But Tetracycline cannot be taken together with all dairy products, aluminium, iron and zinc minerals. |
| Tetracycline | Sumycin ™, Achromycin VTM, Steclin ™ | | | |
| Drugs against mycobacteria | | | | |
| Clofazimine | Lamprene ™ | Antileprotic | | |
| Dapsone | Avlosulfon ™ | Antileprotic | | |
| Capreomycin | Capastat ™ | Antituberculosis | | |
| Cycloserine | Seromycin ™ | Antituberculosis, urinary tract infections | | |
| Ethambutol(Bs) | Myambutol ™ | Antituberculosis | | |
| Ethionamide | Trecator ™ | Antituberculosis | | Inhibits peptide synthesis |
| Isoniazid | I.N.H. ™ | Antituberculosis | | |
| Pyrazinamide | Aldinamide ™ | Antituberculosis | | |
| Rifampicin (Rifampin in US) | Rifadin ™, Rimactane ™ | mostly Gram-positive and mycobacteria | Reddish-orange sweat, tears, and urine | Binds to the β subunit of RNA polymerase to inhibit transcription |
| Rifabutin | Mycobutin ™ | *Mycobacterium avium* complex | Rash, discolored urine, GI symptoms | |
| Rifapentine | Priftin ™ | Antituberculosis | | |
| Streptomycin | | Antituberculosis | Neurotoxicity ototoxicity | As other amino-glycosides |
| Others | | | | |
| Arsphenamine | Salvarsan ™ | Spirochaetal infections (obsolete) | | |
| Chloramphenicol(Bs) | Chloro-mycetin ™ | Meningitis, MRSA, topical use, or for low-cost internal treatment. Historic: typhus, cholera. Gram-negative, Gram-positive, anaerobes | Rarely: aplastic anemia. | Inhibits bacterial protein synthesis by binding to the 50S subunit of the ribosome |

TABLE 1-continued

Antibiotics by class.

| Generic name | Brand names | Common uses | Possible side effects | Mechanism of action |
|---|---|---|---|---|
| Fosfomycin | Monurol ™, Monuril ™ | Acute cystitis in women | This antibiotic is not recommended for children and 75 up of age | Inactivates enolpyruvyl transferase, thereby blocking cell wall synthesis |
| Fusidic acid | Fucidin ™ | | | |
| Metronidazole | Flagyl ™ | Infections caused by anaerobic bacteria; also amoebiasis, trichomoniasis, giardiasis | Discolored urine, headache, metallic taste, nausea; alcohol is contraindicated | Produces toxic free radicals that disrupt DNA and proteins. This non-specific mechanism is responsible for its activity against a variety of bacteria, amoebae, and protozoa. |
| Mupirocin | Bactroban ™ | Ointment for impetigo, cream for infected cuts | | Inhibits isoleucine t-RNA synthetase (IleRS) causing inhibition of protein synthesis |
| Platensimycin | | | | |
| Quinupristin/Dalfopristin | Synercid ™ | | | |
| Thiamphenicol | | Gram-negative, Gram-positive, anaerobes. Widely used in veterinary medicine. | Rash. Lacks known anemic side-effects. | A chlor-amphenicol analog. May inhibit bacterial protein synthesis by binding to the 50S subunit of the ribosome |
| Tigecycline(Bs) | Tigacyl ™ | Slowly Intravenous. Indicated for complicated skin/skin structure infections, soft tissue infections and complicated intra-abdominal infections. Effective for gram-positive, gram-negative, anaerobic, and against multi-antibiotic resistant bacteria (such as *Staphylococcus aureus* [MRSA] and *Acinetobacter baumannii*), but not effective for | Teeth discoloration and same side effects as tetracycline. Not to be given for children and pregnant or lactate women. Relatively safe and no need dose adjusted when be given for mild to moderate liver | Similar structure with tetracycline, but 5 times stronger, big volume distribution and long half-time in the body |

TABLE 1-continued

| Antibiotics by class. | | | | |
|---|---|---|---|---|
| Generic name | Brand names | Common uses | Possible side effects | Mechanism of action |
| | | *Pseudomonas* spp. and *Proteus* spp. | function or renal patients | |
| Tinidazole | Tindamax ™ Fasigyn ™ | Protozoal infections | Upset stomach, bitter taste, and itchiness | |
| Trimethoprim(Bs) | Proloprim ™, Trimpex ™ | Urinary tract infections | | |

Note:
(Bs): Bacteriostatic

TABLE 2

| Antibiotic candidates. | | | | |
|---|---|---|---|---|
| Generic name | Origin | Susceptible phyla | Stage of development | Mechanism of action |
| Unclassified | | | | |
| Teixobactin | Eleftheria terrae | Gram-positive, including antibiotic resistant *S. aureus* and *M. tuberculosis* | No human trials scheduled | Binds fatty acid precursors to cell wall |
| Malacidins | Uncultured Bacterium | Gram-positive, including antibiotic resistant *S. aureus* | No human trials scheduled | Binds fatty acid precursors to cell wall |

The compositions described herein can treat any bacterial infection, such as an antibiotic resistant infection. As an example, the compositions described herein can treat methicillin-resistant *Staphylococcus aureus* (MRSA), *Pseudomonas aeruginosa*, or vancomycin-resistant *Enterococcus* (VRE).

Other infections that can be treated using the compositions described herein can include acne, bronchitis, conjunctivitis (pink eye), otitis media (Ear Infection), sexually transmitted diseases (STDs), skin or soft tissue infection, streptococcal pharyngitis (strep throat), traveler's diarrhea, upper respiratory tract infection, urinary tract infection (UTI), or any infection listed in TABLE 1 or TABLE 2.

Overcoming Drug Toxicity

The present disclosure provides for compositions and methods to overcome the major challenge of drug toxicity. Here is described a next-generation universal plug-and-play drug delivery system comprised of linked supramolecular monomers that can act as 'smart' receptors for a wide variety of small-molecule anti-cancer drugs that can be polymerized together in precise monomer ratios to yield combination drug-loaded nanoparticles.

Treatments for aggressive and metastatic types of cancer often come in the form of "cocktails" that consist of multiple small-molecule anti-cancer drugs that are often administered multiple times intravenously over the course of a lengthy treatment regimen. One example of this combination-based strategy is FOLFIRINOX—consisting of Folinic acid, Fluorouracil, Irinotecan, and Oxaliplatin—which is often used to treat metastatic pancreatic cancer. Although it is an effective treatment capable of extending the median overall survival rate to 11.1 months, compared to only a few months with other single-drug-based systems, FOLFIRINOX is also incredibly toxic and may result in an increased rate of infection due to a drop in white blood cells, tiredness as a result of a lower red blood cell count, the formation of ulcers, hair loss, and so on. The drug delivery community has worked to develop systems capable of delivering anticancer drugs with improved pharmacokinetics and dramatically reduced toxicities, however, it remains a major challenge to construct platforms that can support the precise loading of three or more drugs without unintentional early release of drugs (see e.g., FIG. 27), 'Traditional' liposomal strategy). Even more troubling, there are also now concerns emerging over how drugs that are conjugated directly to the delivery platform are not released completely and efficiently once inside the tumor, and even when they are released in vitro/vivo, their mode of action may be different than what is expected in comparison to the observed mechanisms of small-molecule free drugs (see e.g., FIG. 27), 'Recent' polymer nanoparticle strategy). These major delivery issues can often perturb or completely derail clinical trials that investigate efficacy using modern drug delivery systems.

The drug delivery agent described herein can mitigate the above challenges for combination anti-cancer therapeutics. For example, the drug delivery agent as described herein can include any anti-cancer therapeutic or chemotherapeutic agent known in the art. For example, the drug delivery agent as described herein can incorporate one or more anti-cancer therapeutic or chemotherapeutic agents. As an example, the one or more chemotherapeutic agent can be Abiraterone Acetate; Abitrexate (Methotrexate); Abraxane (Paclitaxel Albumin-stabilized Nanoparticle Formulation); ABVD; ABVE; ABVE-PC; AC; AC-T; Adcetris (Brentuximab Vedotin); ADE; Ado-Trastuzumab Emtansine; Adriamycin (Doxorubicin Hydrochloride); Afatinib Dimaleate; Afinitor (Everolimus); Akynzeo (Netupitant and Palonosetron Hydrochloride); Aldara (Imiquimod); Aldesleukin; Alecensa (Alectinib); Alectinib; Alemtuzumab; Alkeran (Melphalan Hydrochloride); Alkeran (Melphalan); Alimta (Pemetrexed Disodium); Aloxi (Palonosetron Hydrochloride); Ambochlorin/Amboclorin (Chlorambucil); Amifostine; Aminolevulinic Acid; Anastrozole; Aprepitant; Aredia (Pamidronate Disodium); Arimidex (Anastrozole); Aromasin (Exemestane); Arranon (Nelarabine); Arsenic Trioxide; Arzerra (Ofatumumab); Asparaginase *Erwinia chrysanthemi*; Atezolizumab; Avastin (Bevacizumab); Avelumab; Axitinib; Azacitidine; Bavencio (Avelumab); BEACOPP; Becenum (Carmustine); Beleodaq (Belinostat); Belinostat; Benda-mustine Hydrochloride; BEP; Bevacizumab; Bexarotene; Bexxar (Tositumomab and Iodine|131 Tositumomab); Bicalutamide; BiCNU (Carmustine); Bleomycin; Blinatu-momab; Blincyto (Blinatumomab); Bortezomib; Bosulif (Bosutinib); Bosutinib; Brentuximab Vedotin; BuMel; Busulfan; Busulfex (Busulfan); Cabazitaxel; Cabometyx (Cabozantinib-S-Malate); Cabozantinib-S-Malate; CAF; Campath (Alemtuzumab); Camptosar (Irinotecan Hydro-chloride); Capecitabine; CAPOX; Carac (Fluorouracil—Topical); Carboplatin; Carboplatin-Taxol; Carfilzomib; Car-mubris (Carmustine); Casodex (Bicalutamide); CEM; Ceritinib; Cerubidine (Daunorubicin Hydrochloride); Cer-varix (Recombinant HPV Bivalent Vaccine); Cetuximab; CEV; Chlorambucil; Chlorambucil-prednisone; CHOP; Cis-platin; Cladribine; Clafen (Cyclophosphamide); Clofara-bine; Clofarex (Clofarabine); Clolar (Clofarabine); CMF; Cobimetinib; Cometriq (Cabozantinib-S-Malate); COP-DAC; COPP; COPP-ABV; Cosmegen (Dactinomycin); Cotellic (Cobimetinib); Crizotinib; CVP; Cyclophosph-amide; Cyfos (Ifosfamide); Cyramza (Ramucirumab); Cyt-arabine; Cytarabine Liposome; Cytosar-U (Cytarabine); Cytoxan (Cyclophosphamide); Dabrafenib; Dacarbazine; Dacogen (Decitabine); Dactinomycin; Daratumumab; Darzalex (Daratumumab); Dasatinib; Daunorubicin Hydro-chloride; Decitabine; Defibrotide Sodium; Defitelio (Defi-brotide Sodium); Degarelix; Denileukin Diftitox; Deno-sumab; DepoCyt (Cytarabine Liposome); Dexamethasone; Dexrazoxane Hydrochloride; Dinutuximab; Docetaxel; Doxil (Doxorubicin Hydrochloride Liposome); Doxorubicin Hydrochloride; Doxorubicin Hydrochloride Liposome; Dox-SL (Doxorubicin Hydrochloride Liposome); DTIC-Dome (Dacarbazine); Efudex (Fluorouracil—Topical); Eli-tek (Rasburicase); Ellence (Epirubicin Hydrochloride); Elotuzumab; Eloxatin (Oxaliplatin); Eltrombopag Olamine; Emend (Aprepitant); Empliciti (Elotuzumab); Enzaluta-mide; Epirubicin Hydrochloride; EPOCH; Erbitux (Cetux-imab); Eribulin Mesylate; Erivedge (Vismodegib); Erlotinib Hydrochloride; Erwinaze (Asparaginase *Erwinia chrysan-themi*); Ethyol (Amifostine); Etopophos (Etoposide Phos-phate); Etoposide; Etoposide Phosphate; Evacet (Doxorubi-cin Hydrochloride Liposome); Everolimus; Evista (Raloxifene Hydrochloride); Evomela (Melphalan Hydro-chloride); Exemestane; 5-FU (Fluorouracil Injection); 5-FU (Fluorouracil—Topical); Fareston (Toremifene); Farydak (Panobinostat); Faslodex (Fulvestrant); FEC; Femara (Letrozole); Filgrastim; Fludara (Fludarabine Phosphate); Fludarabine Phosphate; Fluoroplex (Fluorouracil-Topical); Fluorouracil Injection; Fluorouracil—Topical; Flutamide; Folex (Methotrexate); Folex PFS (Methotrexate); FOLFIRI; FOLFIRI-BEVACIZUMAB; FOLFIRI-CETUXIMAB; FOLFIRINOX; FOLFOX; Folotyn (Pralatrexate); FU-LV; Fulvestrant; Gardasil (Recombinant HPV Quadrivalent Vac-cine); Gardasil 9 (Recombinant HPV Nonavalent Vaccine); Gazyva (Obinutuzumab); Gefitinib; Gemcitabine Hydro-chloride; Gemcitabine-Cisplatin; GEMCITABINE-OXA-LIPLATIN; Gemtuzumab Ozogamicin; Gemzar (Gemcit-abine Hydrochloride); Gilotrif (Afatinib Dimaleate); Gleevec (Imatinib Mesylate); Gliadel (Carmustine Implant); Gliadel wafer (Carmustine Implant); Glucarpidase; Goser-elin Acetate; Halaven (Eribulin Mesylate); Hemangeol (Pro-pranolol Hydrochloride); Herceptin (Trastuzumab); HPV Bivalent Vaccine, Recombinant; HPV Nonavalent Vaccine, Recombinant; HPV Quadrivalent Vaccine, Recombinant; Hycamtin (Topotecan Hydrochloride); Hydrea (Hy-droxyurea); Hydroxyurea; Hyper-CVAD; Ibrance (Palboci-clib); Ibritumomab Tiuxetan; Ibrutinib; ICE; Iclusig (Ponatinib Hydrochloride); Idamycin (Idarubicin Hydrochloride); Idarubicin Hydrochloride; Idelalisib; Ifex (Ifosfamide); Ifos-famide; Ifosfamidum (Ifosfamide); IL-2 (Aldesleukin); Ima-tinib Mesylate; Imbruvica (Ibrutinib); Imiquimod; Imlygic (Talimogene Laherparepvec); Inlyta (Axitinib); Interferon Alfa-2b, Recombinant; Interleukin-2 (Aldesleukin); Intron A (Recombinant Interferon Alfa-2b); Iodine|131 Tositumo-mab and Tositumomab; Ipilimumab; Iressa (Gefitinib); Iri-notecan Hydrochloride; Irinotecan Hydrochloride Lipo-some; Istodax (Romidepsin); Ixabepilone; Ixazomib Citrate; Ixempra (Ixabepilone); Jakafi (Ruxolitinib Phosphate); JEB; Jevtana (Cabazitaxel); Kadcyla (Ado-Trastuzumab Emtansine); Keoxifene (Raloxifene Hydrochloride); Kepi-vance (Palifermin); Keytruda (Pembrolizumab); Kisqali (Ri-bociclib); Kyprolis (Carfilzomib); Lanreotide Acetate; Lapa-tinib Ditosylate; Lartruvo (Olaratumab); Lenalidomide; Lenvatinib Mesylate; Lenvima (Lenvatinib Mesylate); Letrozole; Leucovorin Calcium; Leukeran (Chlorambucil); Leuprolide Acetate; Leustatin (Cladribine); Levulan (Ami-nolevulinic Acid); Linfolizin (Chlorambucil); LipoDox (Doxorubicin Hydrochloride Liposome); Lomustine; Lon-surf (Trifluridine and Tipiracil Hydrochloride); Lupron (Leuprolide Acetate); Lupron Depot (Leuprolide Acetate); Lupron Depot-Ped (Leuprolide Acetate); Lynparza (Olapa-rib); Marqibo (Vincristine Sulfate Liposome); Matulane (Procarbazine Hydrochloride); Mechlorethamine Hydro-chloride; Megestrol Acetate; Mekinist (Trametinib); Mel-phalan; Melphalan Hydrochloride; Mercaptopurine; Mesna; Mesnex (Mesna); Methazolastone (Temozolomide); Metho-trexate; Methotrexate LPF (Methotrexate); Methylnaltrex-one Bromide; Mexate (Methotrexate); Mexate-AQ (Metho-trexate); Mitomycin C; Mitoxantrone Hydrochloride; Mitozytrex (Mitomycin C); MOPP; Mozobil (Plerixafor); Mustargen (Mechlorethamine Hydrochloride); Mutamycin (Mitomycin C); Myleran (Busulfan); Mylosar (Azacitidine); Mylotarg (Gemtuzumab Ozogamicin); Nanoparticle Pacli-taxel (Paclitaxel Albumin-stabilized Nanoparticle Formula-tion); Navelbine (Vinorelbine Tartrate); Necitumumab; Nelarabine; Neosar (Cyclophosphamide); Netupitant and Palonosetron Hydrochloride; Neulasta (Pegfilgrastim); Neupogen (Filgrastim); Nexavar (Sorafenib Tosylate); Nilandron (Nilutamide); Nilotinib; Nilutamide; Ninlaro (Ixazomib Citrate); Nivolumab; Nolvadex (Tamoxifen Cit-rate); Nplate (Romiplostim); Obinutuzumab; Odomzo (Sonidegib); OEPA; Ofatumumab; OFF; Olaparib; Olara-tumab; Omacetaxine Mepesuccinate; Oncaspar (Pegaspar-gase); Ondansetron Hydrochloride; Onivyde (Irinotecan Hydrochloride Liposome); Ontak (Denileukin Diftitox); Opdivo (Nivolumab); OPPA; Osimertinib; Oxaliplatin; Paclitaxel; Paclitaxel Albumin-stabilized Nanoparticle For-mulation; PAD; Palbociclib; Palifermin; Palonosetron Hydrochloride; Palonosetron Hydrochloride and Netupitant; Pamidronate Disodium; Panitumumab; Panobinostat; Para-plat (Carboplatin); Paraplatin (Carboplatin); Pazopanib Hydrochloride; PCV; PEB; Pegaspargase; Pegfilgrastim; Peginterferon Alfa-2b; PEG-Intron (Peginterferon Alfa-2b); Pembrolizumab; Pemetrexed Disodium; Perjeta (Per-tuzumab); Pertuzumab; Platinol (Cisplatin); Platinol-AQ (Cisplatin); Plerixafor; Pomalidomide; Pomalyst (Pomalido-mide); Ponatinib Hydrochloride; Portrazza (Necitumumab); Pralatrexate; Prednisone; Procarbazine Hydrochloride; Pro-leukin (Aldesleukin); Prolia (Denosumab); Promacta (El-trombopag Olamine); Propranolol Hydrochloride; Provenge (Sipuleucel-T); Purinethol (Mercaptopurine); Purixan (Mer-captopurine); Radium 223 Dichloride; Raloxifene Hydro-chloride; Ramucirumab; Rasburicase; R-CHOP; R-CVP; Recombinant Human Papillomavirus (HPV) Bivalent Vaccine; Recombinant Human Papillomavirus (HPV) Nonavalent Vaccine; Recombinant Human Papillomavirus (HPV) Quadrivalent Vaccine; Recombinant Interferon Alfa-2b; Regorafenib; Relistor (Methylnaltrexone Bromide); R-EPOCH; Revlimid (Lenalidomide); Rheumatrex (Methotrexate); Ribociclib; R-ICE; Rituxan (Rituximab); Rituximab; Rolapitant Hydrochloride; Romidepsin; Romiplostim; Rubidomycin (Daunorubicin Hydrochloride); Rubraca (Rucaparib Camsylate); Rucaparib Camsylate; Ruxolitinib Phosphate; Sclerosol Intrapleural Aerosol (Talc); Siltuximab; Sipuleucel-T; Somatuline Depot (Lanreotide Acetate); Sonidegib; Sorafenib Tosylate; Sprycel (Dasatinib); STANFORD V; Sterile Talc Powder (Talc); Steritalc (Talc); Stivarga (Regorafenib); Sunitinib Malate; Sutent (Sunitinib Malate); Sylatron (Peginterferon Alfa-2b); Sylvant (Siltuximab); Synribo (Omacetaxine Mepesuccinate); Tabloid (Thioguanine); TAC; Tafinlar (Dabrafenib); Tagrisso (Osimertinib); Talc; Talimogene Laherparepvec; Tamoxifen Citrate; Tarabine PFS (Cytarabine); Tarceva (Erlotinib Hydrochloride); Targretin (Bexarotene); Tasigna (Nilotinib); Taxol (Paclitaxel); Taxotere (Docetaxel); Tecentriq (Atezolizumab); Temodar (Temozolomide); Temozolomide; Temsirolimus; Thalidomide; Thalomid (Thalidomide); Thioguanine; Thiotepa; Tolak (Fluorouracil—Topical); Topotecan Hydrochloride; Toremifene; Torisel (Temsirolimus); Tositumomab and Iodine|131 Tositumomab; Totect (Dexrazoxane Hydrochloride); TPF; Trabectedin; Trametinib; Trastuzumab; Treanda (Bendamustine Hydrochloride); Trifluridine and Tipiracil Hydrochloride; Trisenox (Arsenic Trioxide); Tykerb (Lapatinib Ditosylate); Unituxin (Dinutuximab); Uridine Triacetate; VAC; Vandetanib; VAMP; Varubi (Rolapitant Hydrochloride); Vectibix (Panitumumab); VelP; Velban (Vinblastine Sulfate); Velcade (Bortezomib); Velsar (Vinblastine Sulfate); Vemurafenib; Venclexta (Venetoclax); Venetoclax; Viadur (Leuprolide Acetate); Vidaza (Azacitidine); Vinblastine Sulfate; Vincasar PFS (Vincristine Sulfate); Vincristine Sulfate; Vincristine Sulfate Liposome; Vinorelbine Tartrate; VIP; Vismodegib; Vistogard (Uridine Triacetate); Voraxaze (Glucarpidase); Vorinostat; Votrient (Pazopanib Hydrochloride); Wellcovorin (Leucovorin Calcium); Xalkori (Crizotinib); Xeloda (Capecitabine); XELIRI; XELOX; Xgeva (Denosumab); Xofigo (Radium 223 Dichloride); Xtandi (Enzalutamide); Yervoy (Ipilimumab); Yondelis (Trabectedin); Zaltrap (Ziv-Aflibercept); Zarxio (Filgrastim); Zelboraf (Vemurafenib); Zevalin (Ibritumomab Tiuxetan); Zinecard (Dexrazoxane Hydrochloride); Ziv-Aflibercept; Zofran (Ondansetron Hydrochloride); Zoladex (Goserelin Acetate); Zoledronic Acid; Zolinza (Vorinostat); Zometa (Zoledronic Acid); Zydelig (Idelalisib); Zykadia (Ceritinib); or Zytiga (Abiraterone Acetate).

Methods and compositions as described herein can be used for the prevention, treatment, or slowing the progression of cancer. For example, the cancer can be Acute Lymphoblastic Leukemia (ALL); Acute Myeloid Leukemia (AML); Adrenocortical Carcinoma; AIDS-Related Cancers; Kaposi Sarcoma (Soft Tissue Sarcoma); AIDS-Related Lymphoma (Lymphoma); Primary CNS Lymphoma (Lymphoma); Anal Cancer; Appendix Cancer; Gastrointestinal Carcinoid Tumors; Astrocytomas; Atypical Teratoid/Rhabdoid Tumor, Childhood, Central Nervous System (Brain Cancer); Basal Cell Carcinoma of the Skin; Bile Duct Cancer; Bladder Cancer; Bone Cancer (including Ewing Sarcoma and Osteosarcoma and Malignant Fibrous Histiocytoma); Brain Tumors; Breast Cancer; Bronchial Tumors; Burkitt Lymphoma; Carcinoid Tumor (Gastrointestinal); Childhood Carcinoid Tumors; Cardiac (Heart) Tumors; Central Nervous System cancer; Atypical Teratoid/Rhabdoid Tumor, Childhood (Brain Cancer); Embryonal Tumors, Childhood (Brain Cancer); Germ Cell Tumor, Childhood (Brain Cancer); Primary CNS Lymphoma; Cervical Cancer; Cholangiocarcinoma; Bile Duct Cancer Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell; Ductal Carcinoma In Situ (DCIS); Embryonal Tumors, Central Nervous System, Childhood (Brain Cancer); Endometrial Cancer (Uterine Cancer); Ependymoma, Childhood (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Intraocular Melanoma; Retinoblastoma; Fallopian Tube Cancer; Fibrous Histiocytoma of Bone, Malignant, or Osteosarcoma; Gallbladder Cancer; Gastric (Stomach) Cancer; Gastrointestinal Carcinoid Tumor; Gastrointestinal Stromal Tumors (GIST) (Soft Tissue Sarcoma); Germ Cell Tumors; Central Nervous System Germ Cell Tumors (Brain Cancer); Childhood Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Heart Tumors; Hepatocellular (Liver) Cancer; Histiocytosis, Langerhans Cell; Hodgkin Lymphoma; Hypopharyngeal Cancer (Head and Neck Cancer); Intraocular Melanoma; Islet Cell Tumors; Pancreatic Neuroendocrine Tumors; Kaposi Sarcoma (Soft Tissue Sarcoma); Kidney (Renal Cell) Cancer; Langerhans Cell Histiocytosis; Laryngeal Cancer (Head and Neck Cancer); Leukemia; Lip and Oral Cavity Cancer (Head and Neck Cancer); Liver Cancer; Lung Cancer (Non-Small Cell and Small Cell); Lymphoma; Male Breast Cancer; Malignant Fibrous Histiocytoma of Bone or Osteosarcoma; Melanoma; Melanoma, Intraocular (Eye); Merkel Cell Carcinoma (Skin Cancer); Mesothelioma, Malignant; Metastatic Cancer; Metastatic Squamous Neck Cancer with Occult Primary (Head and Neck Cancer); Midline Tract Carcinoma Involving NUT Gene; Mouth Cancer (Head and Neck Cancer); Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms; Nasal Cavity and Paranasal Sinus Cancer (Head and Neck Cancer)' Nasopharyngeal Cancer (Head and Neck Cancer)' Neuroblastoma; Non-Hodgkin Lymphoma; Non-Small Cell Lung Cancer; Oral Cancer, Lip or Oral Cavity Cancer; Oropharyngeal Cancer (Head and Neck Cancer); Osteosarcoma and Malignant Fibrous Histiocytoma of Bone; Ovarian Cancer Pancreatic Cancer; Pancreatic Neuroendocrine Tumors (Islet Cell Tumors); Papillomatosis; Paraganglioma; Paranasal Sinus and Nasal Cavity Cancer (Head and Neck Cancer); Parathyroid Cancer; Penile Cancer; Pharyngeal Cancer (Head and Neck Cancer); Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer Renal Cell (Kidney) Cancer; Retinoblastoma; Rhabdomyosarcoma, Childhood (Soft Tissue Sarcoma); Salivary Gland Cancer (Head and Neck Cancer); Sarcoma; Childhood Rhabdomyosarcoma (Soft Tissue Sarcoma); Childhood Vascular Tumors (Soft Tissue Sarcoma); Ewing Sarcoma (Bone Cancer); Kaposi Sarcoma (Soft Tissue Sarcoma); Osteosarcoma (Bone Cancer); Uterine Sarcoma; Sézary Syndrome (Lymphoma); Skin Cancer; Small Cell Lung Cancer; Small Intestine Cancer; Soft Tissue Sarcoma; Squamous Cell Carcinoma of the Skin; Squamous Neck Cancer with Occult Primary, Metastatic (Head and Neck Cancer); Stomach (Gastric) Cancer; T-Cell Lymphoma, Cutaneous; Lymphoma; Mycosis Fungoides and Sèzary Syndrome; Testicular Cancer; Throat Cancer (Head and Neck Cancer); Nasopharyngeal Cancer; Oropharyngeal Cancer; Hypopharyngeal Cancer; Thymoma and Thymic Carcinoma; Thyroid Cancer; Thyroid Tumors; Transitional Cell Cancer of the Renal Pelvis and Ureter (Kidney (Renal Cell) Cancer); Ureter and Renal Pelvis; Transitional Cell Cancer (Kidney (Renal Cell) Cancer; Urethral Cancer; Uterine Cancer, Endometrial; Uterine Sarcoma; Vaginal Cancer; Vascular Tumors (Soft Tissue Sarcoma); Vulvar Cancer; or Wilms Tumor.

Polymer-Based Drug-Delivery Agent

Provided herein are compositions and methods of making and using drug-binding polymers for targeted combination antibacterial and anticancer therapies.

Briefly, the invention disclosed herein involves the design, synthesis, and efficacy of a polymer-based platform consisting of drug-binding receptors (or macrocycles) and targeting agents attached to a polynorbornene backbone for the purpose of serving as a 'universal' platform for the delivery of different combinations of small-molecule drugs and/or metal ions (e.g., silver ($Ag^+$) or copper ($Cu^{2+}$)) in an effort to treat infections caused by multidrug-resistant (MDR) bacteria or to treat aggressive forms of cancer. The novelty of the disclosed design relates to the drug-binding (or supramolecular) monomers that were synthesized and used to make the functional drug delivery polymers. Each selective receptor (one for binding small-molecule drugs and the other for binding metal ions) is functionalized with a polymerizable group—in this case a norbornene capable of undergoing ring-opening metathesis polymerization (ROMP)—which can be polymerized together in precise ratios to afford a polymer that can temporarily house the small-molecule drugs and metal ions that serve as antimicrobials or as imaging agents if radioisotopes are used. Additionally, targeting monomers and/or other polyethylene glycol (PEG)-based biocompatible monomers can be added in during the ROMP step of the supramolecular monomers to build a complete polymer-based drug delivery platform capable of delivering any combination of clinically relevant drug cocktails, which are usually incredibly toxic, as well as imaging and targeting moieties that aid in the process of finding the site of infection and in tracking the material in vivo.

The disclosed platform technology is different from other drug delivery polymer systems because the presently disclosed drug-binding receptors can bind a wide range of small molecule drugs and metal ions. This means it is unnecessary to re-synthesize drug-conjugated monomers and polymers for each application. Instead, the same batch of drug-binding polymers can be used with any combination of drugs and metal ions, the composition of which depends on the desired treatment regimen, thus circumventing the excessive time that is generally required to evaluate a wide range of drug combinations.

Macrocyclic Moiety

As shown herein, one or more macrocyclic moieties (i.e., macrocycles) can be incorporated into a polymer-based drug-delivery agent. Any macrocyclic moiety known in the art can be used in the polymer-based drug-delivery agent as described herein. For example, the polymer-based drug-delivery agent can comprise one or more of a cyclodextrin, a calixarene, a crown ether, or a cyclophane.

Host-guest systems using macrocyclic moieties are well known; see e.g. Canceill et al. Supramolecular Chemistry I—Directed Synthesis and Molecular Recognition Springer-Verlag 1993; Container Molecules and Their Guests. By D. J. Cram and J. M. Cram. (Series: Monographs in Supramolecular Chemistry, Vol. 4; Neri et al. Calixarenes and Beyond Springer International Publishing Switzerland 2016). Except as otherwise noted herein, therefore, the compositions and processes of the present disclosure can be as described or carried out in accordance with such processes.

Macrocyclic moieties can be modified to change their receptor size or functional groups can added to tune the receptor to be a suitable size for binding of a drug and for drug release.

Cyclodextrins

As described herein, a cyclodextrin can be incorporated into a polymer-based drug-delivery agent. Cyclodextrins are a family of cyclic oligosaccharides, consisting of a macrocyclic ring of glucose subunits joined by $\alpha$-1,4 glycosidic bonds. Cyclodextrins can be produced from starch by enzymatic conversion. They can be used in food, pharmaceutical, drug delivery, and chemical industries, as well as agriculture and environmental engineering.

Cyclodextrins can be composed of 5 or more $\alpha$-D-glucopyranoside units linked 1→4, as in amylose (a fragment of starch). The largest cyclodextrin contains 32 1,4-anhydroglucopyranoside units, while as a poorly characterized mixture, at least 150-membered cyclic oligosaccharides are also known. Typical cyclodextrins can contain a number of glucose monomers ranging from six to eight units in a ring, creating a cone shape. For example, $\alpha$ (alpha)-cyclodextrin has 6 glucose subunits, $\beta$ (beta)-cyclodextrin has 7 glucose subunits, and $\gamma$ (gamma)-cyclodextrin has 8 glucose subunits.

Cyclodextrins can be constituted by 6-8 glucopyranoside units. These subunits can be linked by 1,4 glycosidic bonds. Cyclodextrins can have toroidal shapes, with the larger and the smaller openings of the toroid exposing to the solvent secondary and primary hydroxyl groups respectively. Because of this arrangement, the interior of the toroids is not hydrophobic, but considerably less hydrophilic than the aqueous environment and thus able to host other hydrophobic molecules. In contrast, the exterior is sufficiently hydrophilic to impart cyclodextrins (or their complexes) water solubility. They are not typically soluble in typical organic solvents.

Calixarenes

As described herein, a calixarene can be incorporated into a polymer-based drug-delivery agent. A calixarene is a macrocyclic moiety (e.g., a macrocycle or a cyclic oligomer) based on a hydroxyalkylation product of a phenol and an aldehyde.

The word calixarene is derived from calix or chalice because this type of molecule resembles a vase and from the word arene that refers to the aromatic building block. Calixarenes can have hydrophobic cavities that can hold smaller molecules or ions and belong to the class of cavitands known in host-guest chemistry. Calixarene nomenclature is straightforward and involves counting the number of repeating units in the ring and include it in the name. A calix[4]arene has 4 units in the ring and a calix[6]arene has 6. A substituent in the meso position Rb is added to the name with a prefix C- as in C-methylcalix[6]arene.

The aromatic components can be derived from phenol, resorcinol, or pyrogallol. For phenol, the aldehyde most often used is simple formaldehyde, while larger aldehydes, like acetaldehyde, are usually required in condensation reactions with resorcinol and pyrogallol. The chemical reaction qualifies as electrophilic aromatic substitution, followed by an elimination of water, and then a second aromatic substitution. The reaction is catalyzed by acids or bases.

Calixarenes are characterized by a three-dimensional basket, cup or bucket shape. In calix[4]arenes the internal volume is around 10 cubic angstroms. Calixarenes are characterised by a wide upper rim and a narrow lower rim and a central annulus. With phenol as a starting material the 4 hydroxyl groups are intrannular on the lower rim. In a resorcin[4]arene 8 hydroxyl groups are placed extraannular on the upper ring. Calixarenes can exist in different chemical conformations because rotation around the methylene bridge is not difficult. In calix[4]arene 4 up-down conformations exist: cone (point group $C_{2v}, C_{4v}$), partial cone $C_s$, 1,2 alternate $C_{2h}$ and 1,3 alternate $D_{2d}$. The 4 hydroxyl groups interact by hydrogen bonding and stabilize the cone conformation. This conformation is in dynamic equilibrium with the other conformations. Conformations can be locked in place with proper substituents replacing the hydroxyl groups which increase the rotational barrier. Alternatively placing a bulky substituent on the upper rim also locks a conformation. The calixarene based on p-tert-butyl phenol is also a cone. Calixarenes are structurally related to the pillararenes.

Calixarenes can be efficient ionophores and, thus, can be useful in delivery of ions, such as $Ag^+$, as described herein. Derivatives or homologues of calix[4]arene exhibit highly selective binding behavior towards anions (especially halogen anions).

Crown Ethers

As described herein, a crown ether can be incorporated into a polymer-based drug-delivery agent.

Crown ethers are cyclic chemical compounds that consist of a ring containing several ether groups. The most common crown ethers are cyclic oligomers of ethylene oxide, the repeating unit being ethyleneoxy, i.e., —$CH_2CH_2O$—. Important members of this series are the tetramer (n=4), the pentamer (n=5), and the hexamer (n=6). The term "crown" refers to the resemblance between the structure of a crown ether bound to a cation, and a crown sitting on a person's head. The first number in a crown ether's name refers to the number of atoms in the cycle, and the second number refers to the number of those atoms that are oxygen. Crown ethers are much broader than the oligomers of ethylene oxide; an important group are derived from catechol.

Crown ethers strongly bind certain cations, forming complexes. The oxygen atoms are well situated to coordinate with a cation located at the interior of the ring, whereas the exterior of the ring is hydrophobic. The resulting cations often form salts that are soluble in nonpolar solvents, and for this reason crown ethers are useful in phase transfer catalysis. The denticity of the polyether influences the affinity of the crown ether for various cations. For example, 18-crown-6 has high affinity for potassium cation, 15-crown-5 for sodium cation, and 12-crown-4 for lithium cation.

Crown ethers have been shown to coordinate to Lewis acids through electrostatic, σ-hole (see halogen bond) interactions, between the Lewis basic oxygen atoms of the crown ether and the electrophilic Lewis acid center.

Crown ethers have a high affinity for potassium cations. For example, 18-crown-6 can also bind to protonated amines and form very stable complexes in both solution and the gas phase. Some amino acids, such as lysine, contain a primary amine on their side chains. Those protonated amino groups can bind to the cavity of 18-crown-6 and form stable complexes in the gas phase. Hydrogen-bonds are formed between the three hydrogen atoms of protonated amines and three oxygen atoms of 18-crown-6. These hydrogen-bonds make the crown ether inclusion complex a stable adduct.

Cyclophanes

As described herein, a cyclophane can be incorporated into a polymer-based drug-delivery agent.

A cyclophane is a hydrocarbon consisting of an aromatic unit (typically a benzene ring) and an aliphatic chain that forms a bridge between two non-adjacent positions of the aromatic ring. More complex derivatives with multiple aromatic units and bridges forming cagelike structures are also known. Cyclophanes are well-studied in organic chemistry because they adopt unusual chemical conformations due to build-up of strain.

Basic cyclophane types are [n]metacyclophanes (I), [n]paracyclophanes (II), and [n,n']cyclophanes (III). The prefixes meta and para correspond to the usual arene substitution patterns and n refers to the number of atoms making up the bridge.

Paracyclophanes adopt the boat conformation normally observed in cyclohexanes but are still able to retain aromaticity. The smaller the value of n the larger the deviation from aromatic planarity. In [6]paracyclophane which is one of the smallest, yet stable, cyclophanes X-ray crystallography shows that the aromatic bridgehead carbon atom makes an angle of 20.5° with the plane. The benzyl carbons deviate by another 20.2°. The carbon-to-carbon bond length alternation has increased from 0 for benzene to 39 pm.

Molecular Self-Assembly and Three Dimensional Polymer Networks

As described herein, the polymer-based drug-delivery agents are capable of molecular self-assembly. Molecular self-assembly of macrocyclic moieties (macrocycles) can lead to larger supramolecular assemblies (e.g., micelles, nanoparticles).

Furthermore, a series of polymerized monomers, as described herein, can also incorporate a masked polymerization initiator that can be deprotected and used to initiate a polymerization, thus changing the particle morphology, such as incorporation into a three-dimensional polymer network.

Additionally, the series of polymerized monomers, as described herein, can also form a three dimensional network by the use of a non-covalent cross-linking group (e.g., adamantane-functionalized crosslinker, bis(adamantyl) crosslinker) capable of non-covalently binding two or more macrocyclic moieties.

Binding of Therapeutic Agents

As described herein, the macrocyclic moieties in the polymer-based drug delivery agents can bind a variety of therapeutic agents such as one or more of an antibiotic, an alkali metal cation, transition metal cation, or an anticancer agent.

As described herein, the macrocyclic moiety can bind a small molecule therapeutic, antibiotic, or anticancer drug with a $K_a$ of greater than about 100 $M^{-1}$ ($1 \times 10^2$ $M^{-1}$). For example, a therapeutic can bind to a macrocyclic moiety with a $K_a$ on the order of $10^2$, $10^3$, $10^4$, or $10^5$ or greater. Recitation of each of these discrete values is understood to include ranges between each value. Recitation of each range is understood to include discrete values within the range.

As described herein, the macrocyclic moiety can bind an alkali or transition metal cation with a $K_a$ of greater than about $10^{2-5}$ $M^{-1}$. For example, a therapeutic can bind to a macrocyclic moiety with a $K_a$ on the order of $10^2$, $10^3$, $10^4$, or $10^5$ or greater. Recitation of each of these discrete values is understood to include ranges between each value. Recitation of each range is understood to include discrete values within the range.

Monomers

As shown herein, the monomers (e.g., norbornene (Nb)-based) can comprise macrocyclic moieties, drug-loaded macrocyclic moieties, metal-loaded macrocyclic moieties, targeting agents, imaging agents, protonated groups, etc.

For example, the monomers can comprise a macrocyclic moiety such as a β-cyclodextrin macrocycle groups (β-CD monomer) that can bind anti-cancer or anti-bacterial drugs. Anti-cancer drugs that can be accommodated within the β-CD comprise hydrophobic, small-molecule drugs, such as camptothecin, doxorubicin, cisplatin, oxaliplatin, 5-fluorouracil, Chlorambucil, Methotrexate, or Irinotecan HCl. Anti-bacterial drugs that can be accommodated within the β-CD comprise drugs such as β-lactams (e.g., Amoxicillin, Imipenem), aminoglycosides, quinolones or fluoroquinolones (e.g., Levofloxacin), chloramphenicol, sulfonamides (e.g., Sulfadiazine, Sulfamethoxazole), Tetracycline, Linezolid, or thiol NDM-1 inhibitors.

The monomers can also comprise a macrocyclic moiety such as a thiacalixarene group (TC monomer) that can hold anti-bacterial silver ($Ag^+$) ions. The TC monomer can comprise a tert-butyl-thiacalix[4]arene (TC) derivative. The silver ($Ag^+$) ions can be supplied by $AgNO_3$. As another example, a monomer can comprise a dual-functional tert-butyl-thiacalix[4]arene (TC) derivative and a mono-functionalized β-cyclodextrin (CD) (e.g., a TCCD monomer).

Furthermore, the monomers can also comprise Nb-PEG-X monomers linked to a targeting group (e.g., folate to target breast cancer cells, peptides) or an imaging group (e.g., near-IR dye, MRI contrast agent).

The monomers can also comprise a norbornene (Nb)-based hexaethylene glycol capped with an N-L-arginine-glucosamine subunit (e.g., a Nb-LARGE monomer, Nb-Arg) or Arg-Boc. The monomer can form the outer shell of the self-assembled micelle, is easily protonated, targets bacterial cell surfaces, destabilizes membrane, and induces collagen synthesis during wound healing.

Drug Delivery

With a hydrophobic interior and hydrophilic exterior, macrocyclic moieties (or macrocycles), such as cyclodextrins form complexes with hydrophobic compounds. For example, alpha-, beta-, and gamma-cyclodextrin are all generally recognized as safe by the U.S. FDA. The macrocycles can confer solubility and stability to a variety of drugs. The inclusion compounds of macrocycles with hydrophobic molecules are able to penetrate body tissues. The inclusion compounds can be used to release biologically active compounds under specific conditions. In many cases, the mechanism of controlled degradation of such complexes is based on pH change of water solutions, leading to the loss of hydrogen or ionic bonds between the host and the guest molecules. Alternative means for the disruption of the complexes take advantage of heating or action of enzymes able to cleave α-1,4 linkages between glucose monomers. Cyclodextrins are also shown to enhance mucosal penetration of drugs.

Synthesis

As shown herein, the polymer-based drug-delivery agent (e.g., a drug-loaded nanoparticle) can be synthesized by first synthesizing polymers from norbornene (Nb)-based monomers, and second, the assembly of nanoparticles from polynorbornene polymers. The polymers are synthesized from norbornene (Nb)-based monomers through ratiometric ring-opening metathesis polymerization (ROMP). Furthermore, the ROMP reactions can be conducted using Grubbs' third-generation ruthenium catalyst in non-polar tetrahydrofuran (THF) solvent, and or the polymers can have an active or 'living' ruthenium species on one end.

As an example, the polymers can be synthesized and ordered in precise blocks of monomers with similar functions. Such ordering can result in nanoparticles with distinct layers, blocks, or shells. For example, the nanoparticle can have an inner core of drug-loaded β-CD groups, an inner core of $Ag^+$-loaded TC groups, an outer shell of positively charged, protonated L-arginine-glucosamine monomer (LARGE) groups, and or an outer shell of PEG-X groups, optionally linked to targeting groups or imaging groups.

The assembly of nanoparticles from polynorbornene polymers can occur via self-assembly into micellular nanoparticles at critical micelle concentration (CMC), or through crosslinking monomers using a bis(adamantyl) moiety.

Formulation

The agents and compositions described herein can be formulated by any conventional manner using one or more pharmaceutically acceptable carriers or excipients as described in, for example, Remington's Pharmaceutical Sciences (A.R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A.R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a subject in need of administration of a therapeutically effective amount of a small molecule therapeutic (e.g., antimicrobial, antibiotic, chemotherapeutic) with a drug-loaded polymer-based drug-delivery agent, so as to treat a subject having a disease such as cancer, a wound, infection, etc.

Methods described herein are generally performed on a subject in need thereof. A subject in need of the therapeutic methods described herein can be a subject having, diagnosed with, suspected of having, or at risk for developing cancer, a wound, or infection. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of drug-loaded polymer-based drug-delivery agent is, for example, that amount that would cause the desired therapeutic effect in a subject while minimizing undesired side effects. In various embodiments, an effective amount of drug-loaded polymer-based drug-delivery agent described herein can substantially inhibit a disease such as cancer, a wound, infection, etc., slow the progress of a disease such as cancer, a wound, infection, etc., or limit the development of a disease such as cancer, a wound, infection, etc.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a drug-loaded polymer-based drug-delivery agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit a disease such as cancer, a wound, infection, etc., slow the progress of a disease such as cancer, a wound, infection, etc., or limit the development of a disease such as cancer, a wound, infection, etc., The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a drug-loaded polymer-based drug-delivery agent can occur as a single event or over a time course of treatment. For example, a drug-loaded polymer-based drug-delivery agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a disease such as cancer, a wound, infection, etc.

A drug-loaded polymer-based drug-delivery agent can be administered simultaneously or sequentially with another agent, such as an antibiotic, an anti-inflammatory, or another agent. For example, a drug-loaded polymer-based drug-delivery agent can be administered simultaneously with another agent, such as an antibiotic or an anti-inflammatory. Simultaneous administration can occur through administration of separate compositions, each containing one or more of a drug-loaded polymer-based drug-delivery agent, an antibiotic, an anti-inflammatory, or another agent. Simultaneous administration can occur through administration of one composition containing two or more of a drug-loaded polymer-based drug-delivery agent, an antibiotic, an anti-inflammatory, or another agent. A drug-loaded polymer-based drug-delivery agent can be administered sequentially with an antibiotic, an anti-inflammatory, or another agent. For example, a drug-loaded polymer-based drug-delivery agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10:0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a polymer-based drug-delivery agent, a monomer, a macrocyclic moiety, backbone material, linker groups, polymerization agents, antibiotics, antimicrobials, an alkali or transition metal cation, chemotherapeutic agents, anticancer agents, imaging agents, or targeting agents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10:0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice.

However, those of skill in the art should, in light of the present disclosure, appreciate that many changes can be made in the specific embodiments that are disclosed and still obtain a like or similar result without departing from the spirit and scope of the present disclosure.

Example 1: Non-Covalently Crosslinked Polymeric
Nanoparticles With Precise Macrocyclic
Drug-Loading Sites for Combination Antimicrobial
Delivery The following example describes an antimicrobial-loaded nanoparticle comprising norbornene-based block copolymers bearing selective macrocyclic receptors—namely, thiacalix[4]arene (TCA) and β-cyclodextrin (CD)—that bind (and release) silver ions ($Ag^+$) and a wide range of small-molecule antibiotics.

The rise of antibiotic resistant strains of bacteria represents one of the biggest threats to global health. More frequently, combinations of antibiotics are needed to combat multi-drug-resistant (MDR) bacterial infections, but these are not always effective and may be toxic. Here is described a new and versatile combination antimicrobial-loaded nanoparticle comprising norbornene-based block copolymers bearing selective macrocyclic receptors—namely, thiacalix[4]arene (TCA) and β-cyclodextrin (CD)—that bind (and release) silver ions ($Ag^+$) and a wide range of small-molecule antibiotics, respectively. Crosslinking of the functional block copolymers is achieved in water through host-guest interactions between vacant CD sites and an adamantane-functionalized crosslinker that is added after the loading of $Ag^+$ and antibiotics. Host-antimicrobial binding affinities, nanoparticle release kinetics, and cytotoxicity were investigated, and bioactivity against several MDR strains of bacteria was demonstrated.

Design and Synthesis of a Functional Tetrablock Copolymer

To combine TCA and CD into a single polymer, and ultimately a nanoparticle, each macrocycle was functionalized as its cis-5-norbornene-2,3-dicarboxylic acid imide to give Nb-TCA and Nb-CD (see e.g., FIG. 1A), both of which undergo ring-opening metathesis polymerization (ROMP) using Grubbs' third-generation ruthenium catalyst (G3). The addition of norbornene to TCA was achieved by generating its 1,2 conformer via a Mitsunobu reaction between commercially available TCA and a custom norbornyl-pyridine that is ortho-substituted with methylenethio ethanol linkers. Functionalization of the remaining tert-butyl phenol subunits of the TCA ring with triethylene glycol monomethyl ether chains was carried out to improve the solubility of the monomer in tetrahydrofuran (THF), which was used in the first few steps of the polymerization. The synthesis of Nb-CD was achieved in fewer overall steps by mono-tosylating commercially available CD, followed by nucleophilic displacement of the tosyl group with ethylene diamine. The resultant amino-functionalized CD was reacted with a norbornene-based acyl chloride to afford pure Nb-CD on a multi-gram scale.

Additional monomers were synthesized on a gram scale to enhance functionality of the resultant copolymer and nanoparticle, while also facilitating their solubility in water. A tert-butyloxycarbonyl (Boc)-protected arginine monomer (see e.g., FIG. 1A; Nb-Arg(Boc)) was prepared to serve as a precursor to a positively charged block of the functional copolymer. Similarly, a macromonomer consisting of poly (ethylene glycol) ($PEG_{3000}$) bearing a norbornene group at one end (Nb-PEG) was also synthesized in a few steps and serves as a polar, solubilizing block of the final tetrablock copolymer and corresponding nanoparticle.

Sequential ROMP of each monomer was performed (see e.g., FIG. 1B) at room temperature in an $N_2$-saturated glovebox starting with the arginine-based monomer at a 10:1 ratio of Nb-Arg (Boc):G3. Although the corresponding 'living' homopolymer can be obtained after approx. 30 min, the polymerization proceeded for 2-3 h to ensure complete conversion of monomer. Next, 20 equiv of macromonomer (Nb-PEG) was added to the solution of poly(Arg(Boc)) and the next block was allowed to polymerize for 2-3 h to generate successfully the diblock copolymer poly(Arg (Boc)-b-PEG). Once completed, five equiv of Nb-TCA was added to the growing block copolymer and the reaction ran for 4-6 h to obtain the triblock poly(Arg(Boc)-b-PEG-b-TCA). Finally, the THF solution containing the triblock copolymer was added to a dimethylformamide (DMF) solution containing a mixture of 10 equiv of Nb-CD and 30 equiv of N-methyl-5-norbornene-2,3-dicarboxylic acid imide (Nb-Me). The time required to complete this last polymerization step was longer than the previous steps (8-10 h), however, the multi-functional tetrablock copolymer poly (Arg(Boc)-b-PEG-b-TCA-b-(CD-Me)) was obtained successfully, as determined by gel permeation chromatography (GPC) in DMF (see e.g., FIG. 1C aqueous-based GPC of tetrablock copolymer formation) and proton nuclear magnetic resonance ($^1$H NMR) was performed. It is important to note that the purpose of adding Nb-Me in the last step of the ROMP is two-fold. Firstly, it disrupts the potential for any formation of a supramolecular polymer comprising head-to-tail self-assembly of Nb-CD since a portion of the norbornene group can occupy the hydrophobic cavity of CD, much like that of a small-molecule antibiotic. Secondly, it serves as a spacer to provide some distance between the much larger CD macrocycles along the polynorbornene backbone. This latter point was confirmed by unsuccessful earlier attempts to generate just the homopolymer consisting of 10 subunits of CD. Instead, it was routinely observed, that a degree of polymerization (DP) of only 4-5 CD subunits even though a 10:1 ratio of Nb-CD:G3 was used. It is presently believed that without the addition of the spacer monomer, the ruthenium carbene at the end of the growing polymer chain becomes too crowded at a certain point and therefore unable to ring-open the next incoming Nb-CD. Conversely, the statistical introduction of Nb-Me along the polynorbornene backbone allows for more room in between each CD subunit, and therefore the final block of the tetrablock copolymer can be formed. Using this spacer strategy, it is possible to form pendant CD-based polymers without having to do post-polymerization functionalization, the latter of which is often used to make poly (CD).

Non-Covalent Crosslinking of Tetrablock Copolymer to Obtain Self-Assembled Nanoparticles With the synthesis of the tetrablock copolymer optimized, the ability to crosslink multiple tetrablock copolymers into nanoparticles was assessed by dynamic light scattering (DLS) and scanning tunneling electron microscopy (STEM). It was believed that by controlling the amount of crosslinking between tetrablock copolymers, it would be possible to slow the release of $Ag^+$ and antibiotics from the nanoparticle core (vide infra). The stoichiometric ratio of a bis-adamantane crosslinker (see e.g., FIG. 1A) to the number of vacant CD macrocycles in the tetrablock copolymer that leads to nanoparticle formation was screened by adding as low as 10%, and up to as much as 90%, of the crosslinker. The percentage was calculated by dividing the total number of adamantane groups by the number of available CD macrocycles, assuming an average theoretical DP of 10 CD subunits per tetrablock copolymer. The DLS results shown in FIG. 1D indicate an increase in nanoparticle diameter when 10%, 20%, or 30% adamantane groups are added to an aqueous solution containing poly(Arg(Boc)-b-PEG-b-TCA-b-(CD-Me)). The initial tetrablock copolymer alone is approx. 25 nm in diameter, however, the addition of 10% crosslinker results in nanoparticles that are nearly 60 nm in diameter. When 20% crosslinker is added, the diameter increases to just over 100 nm. At 30% crosslinker, the nanoparticle diameter reaches almost 200 nm. Based on these results, 20% crosslinker is ideal because it generates nanoparticles consisting of multiple tetrablock copolymers, whilst leaving up to 80% of the CD macrocycles vacant for drug binding. See the Supplementary Information file for additional DLS and STEM characterization data for the nanoparticles investigated in this study.

Assessment of Model Diblock Copolymers Affinity Towards Binding Silver and Antibiotics In order to demonstrate the delivery of silver ions and antibiotics simultaneously, the cargo should be loaded into the macrocycles of the tetrablock copolymer prior to the crosslinking step. To ensure binding of $Ag^+$ and different antibiotics into TCA and CD macrocycles that are attached to the polynorbornene backbone, two model diblock copolymers were synthesized (see e.g., FIG. 2A, FIG. 2B). The silver-binding model copolymer consisted of three subunits of PEG and TCA on average (i.e., poly(PEG$_3$-b-TCA$_3$), whereas the model antibiotic-binding copolymer possessed on average three subunits of PEG and a 2:6 CD:Me block, both separated by four Me subunits (i.e., poly(PEG$_3$-b-Me$_4$-b-(CD$_2$-Me$_6$)). To determine an apparent binding constant between the TCA-based diblock copolymer and $Ag^+$, an isothermal titration calorimetry (ITC) experiment was performed (see e.g., FIG. 2A), where the host cell contained poly(PEG$_3$-b-TCA$_3$) dissolved in water and 0.2 mM concentration of TCA was present. Then, a 4 mM solution of AgNO$_3$ was titrated into the host solution in injections that contained 0.1 equiv of $Ag^+$ per TCA macrocycle in the model copolymer. The apparent binding constant ($K_{app}$) measured from this experiment was approx. $6 \times 10^4$ $M^{-1}$ in water, which is very similar to the results obtained from an ITC titration of AgNO$_3$ into a host solution containing the monomer Nb-TCA. It is worth mentioning that by comparing the binding of $Ag^+$ in the case of the model diblock copolymer to that of the corresponding monomer, it is clear the long PEG chains emanating from the polynorbornene backbone do not interfere with uptake of the metal ion in water by the TCA macrocycle. Moreover, the results from the ITC experiment show that the binding process is thermodynamically favorable ($\Delta G = -6.8$ kcal/mol) and enthalpically driven ($\Delta H = -1.26$ kcal/mol).

Multiple attempts to carry out similar ITC experiments to measure $K_{app}$ for the binding of antibiotics by poly(PEG$_3$-b-Me$_4$-b-(CD$_2$-Me$_6$) proved unsuccessful because most of the antibiotics that were investigated are hydrophobic and are therefore not soluble in water. When DMF or dimethyl sulfoxide (DMSO) was used to prepare the stock solution of antibiotics in the syringe, followed by injection into the host solution, the mixing of DMF or DMSO in water prevented the establishment of a stable baseline for the experiment. Thus, $^1$H NMR titrations were carried out (see e.g., FIG. 2B) instead to determine $K_{app}$ for the binding of different antibiotics by the model diblock copolymer. Titration of a 100 mM solution of the antibiotic linezolid in DMF (at 0.1 equiv/addition) into a solution containing poly(PEG$_3$-b-Me$_4$-b-(CD$_2$-Me$_6$) with 1 mM equivalent of CD macrocycles present resulted in shifting of key diagnostic proton resonances from 3.7-3.9 ppm that are associated with the internal cavity of the CD ring. A plot of the change in chemical shift (ppm) versus the number of equiv of linezolid (see e.g., FIG. 2B, right) indicates saturation of the host at one equiv of the guest antibiotic—the stoichiometry of which was also confirmed by performing Job's plots in native CD (i.e., no norbornene, just the macrocycle itself). From this titration, the apparent binding affinity was determined to be $K_{app} = 6.4 \times 10^3$ $M^{-1}$. Similar binding affinities were calculated from titrations involving the model diblock copolymer and other antibiotics. These apparent binding affinities ($K_{app}$) were compared directly to the binding affinities ($K_a$) that were determined from titrations involving native CD and the same antibiotic guest molecules to ensure the affinity of the functional polymer to bind antibiotics is not perturbed when the CD-based drug receptors are tethered to a polynorbornene backbone versus the free macrocycle floating in solution.

Comparison of the Rates of Silver and Antibiotic Release from the Tetrablock Copolymer and the Corresponding Nanoparticle Since each functional aspect of this investigation relies on non-covalent interactions—e.g., binding antimicrobials or crosslinking to form nanoparticles—it was believed that the rate of release of the cargo could be slowed by encapsulation in the macrocyclic receptors of the tetrablock copolymer, and even more so when the copolymer was crosslinked into nanoparticles. The adoption of a core-shell morphology upon crosslinking is therefore expected to result in a core comprising localized TCA and CD macrocycles that can freely exchange antimicrobial cargo, and thus result in slower release kinetics than that observed for the non-crosslinked antimicrobial-loaded copolymer. To test this, the release kinetics were investigated in two separate experiments for $Ag^+$ and 7-hydroxycoumarin, which is a fluorescent small molecule (excitation: 324 nm; emission: 450 nm) that simulates drug binding/release because its $K_a$ is also on the order of $10^3$ $M^{-1}$. To a solution containing poly(Arg (Boc)-b-PEG-b-TCA-b-(CD-Me)) at 6 mg/mL, AgNO$_3$ was added (at 2 equiv per TCA macrocycle) and the solution was allowed to stir for approx. 60 min. Next, 1 mL of the solution was placed in dialysis tubing with a molecular weight cutoff (MWCO) of 1000 Da, and the sealed tubing was placed in a 1 L beaker containing 500 mL H$_2$O. Aliquots of 100 μL were collected at set time points from the surrounding beaker solution over the course of approx. 20 h, and the amount of $Ag^+$ released in ppb was determined (see e.g., FIG. 3A) using inductively coupled plasma mass spectrometry (ICP-MS). The point at which 50% of $Ag^+$ was released was determined to be approx. 45 min and 100% was released after 7.5 h. This rate of release is much slower when compared to releasing the same concentration of $Ag^+$ from just the dialysis tubing when no polymer is present, where after 60 min, 100% of the 'cargo' has been released. When the tetrablock copolymer was crosslinked (at 20% occupancy of CD macrocycles), the experiment was repeated and the point at which 50% of $Ag^+$ was released is almost 3 h, with full release (100%) after approx. 9 h (see e.g., FIG. 3B).

A similar release study was carried out using 7-hydroxy-coumarin as a drug mimic whose release could be monitored by fluorescence spectroscopy.

Example 2: a Supramacromolecular Strategy for Overcoming Antibiotic Resistance in Wound Healing The following example describes compositions, methods of synthesis, and methods of treatments related to drug-loaded nanoparticles comprising various norbornene (Nb)-based monomers. Here is described, in detail, the chemistry associated with the developed supramolecular monomers and polymers that are being investigated as a 'universal' platform for the delivery of different drug combinations.

The disclosed studies comprise three phases (see e.g., FIG. 4). (I) Monomer Development, (II) Copolymerization, and (III) Universal Combo Platform.

Monomer development (I) involves the design and synthesis of two types of functional supramolecular monomers based on thiacalixarene (TC) and beta-cyclodextrin (8-CD) macrocycles—which act as receptors for $Ag^+$ ions and small-molecule antibiotics, respectively—as well as a third monomer that is a glucosamine derivative that is added for self-assembly, targeting, and wound healing purposes.

Copolymerization (II) involves the ratiometric ring-opening metathesis polymerization (ROMP) of the two $Ag^+$/drug-loaded monomers together into precise "blocks" along a polymer backbone. The cytotoxicity of this block copolymer will be assessed against healthy mammalian endothelial cells, and characterization of the release kinetics associated with each receptor will also be investigated.

In the universal combo platform (III), the glucosamine-based monomer is brought on board via polymerization into a third block, which sets the stage for self-assembly of the triblock copolymer into micellular nanomaterials; an overall composition which represents a versatile "super" combination antimicrobial platform that may be used in wound healing applications. The cytotoxicity of these micelles will also be assessed, and their ability to exhibit in vitro efficacy and overcome antibiotic resistance will be evaluated. Optimization of the monomers, copolymers, and the final platforms can be accomplished as needed to obtain optimal drug combinations and release kinetics.

When viewing this broad-spectrum "super" combination platform from the general perspective of the drug delivery community, it is important to note that it also has great potential to solve some of the most common issues that plague many delivery systems. For example, many standard delivery platforms often exhibit early and/or unintended leakage of non-covalent encapsulated drugs, or on the other end of the spectrum, little to no release of covalent (pro) drugs requiring an external trigger for release. The disclosed supramacromolecular strategy described here would overcome these issues since the $Ag^+$/drug-loaded monomers represent stable ($K_a > 10^{3-5}$ $M^{-1}$), well-studied host-guest complexes with predictable properties and release kinetics, and the micellular morphology of the final self-assembled nanomaterial would only further stabilize their encapsulation, while simultaneously presenting outwardly the bacteria-selective targeting agents. These studies can lead to development of the chemistry associated with the disclosed next-generation drug delivery platform that is believed to be capable of laying the foundation for a universal 'plug-and-play' approach to small-molecule drug delivery, and specifically within the context of evaluating the platform as a potent candidate for broad-spectrum antimicrobial therapy that stifles the onset of antibiotic resistance.

(I) Design, Synthesis, and Properties of Three Functional Antimicrobial Monomers The docking of a guest within the cavity of a complimentary host is a strategy that is often employed in nature. Following in nature's footsteps, chemists have developed many different 'artificial' hosts or receptors over the past half century that can bind a wide range of guests. Some of the more commonly studied artificial hosts include (see e.g., FIG. 5) cyclodextrins ($\alpha$-, $\beta$-, and $\gamma$-CD), crown ethers, calix[n]arenes (where n equals the number of aromatic rings in the macrocycle), and cyclophanes. Each receptor binds its preferred guest through precise secondary non-covalent bonding interactions—such as hydrophobic-hydrophobic, ion-dipole, hydrogen bonding, and charge-transfer, to name a few. Of these macrocyclic receptors, $\delta$-CD is the oldest and best-studied, especially in the context of drug delivery on account of its ability to bind hydrophobic small-molecule drugs in a 1:1 ratio, while maintaining its solubility in water. Calix[n]arenes (CA) on the other hand, and in particular thiacalix[n]arenes (TC[n]A), are generally hydrophobic, unless functionalized with charged solubilizing groups. Moreover, a TC[n]A comprised of only four aromatic rings, separated on either side by thioether bridges (see e.g., FIG. 6, middle), possesses a smaller cavity size in comparison to $\beta$-CD ($\sim 3.5$ Å vs. 7.0 Å, respectively). The smaller cavity size for TC[4]A is ideal for selectively binding ions, such as alkali and transition metal cations. For example, the binding affinity between $Ag^+$ ions and traditional TC[4]A is on the order of $K_a = \sim 10^4$ in organic solvents and $10^{2-3}$ $M^{-1}$ in water.

Knowing that it would be possible to capitalize on the binding selectivity of each host as a function of guest size, it was set out to design and synthesize norbornene (Nb)-based derivatives of $\beta$-CD and TC[4]A (see e.g., FIG. 6), which could function as two selective supramolecular monomers capable of binding selectively $Ag^+$ and a range of small-molecule antibiotics. These monomers-namely, Nb-CD and Nb-TC[4]A-would ultimately be polymerized with a third multipurpose Nb-based L-arginine-glucosamine monomer (Nb-LARGE), which will contribute to the final triblock copolymer's ability to self-assemble into micelles, and therefore target bacteria and destabilize their cellular membranes, while also promoting wound healing. The ratio of these monomers in the triblock copolymer can be controlled easily from the outset by setting the relative monomer stoichiometry prior to polymerization. The synthesis to prepare each monomer consists of approximately 4-8 steps, where in the case of some of the synthetic steps, time-consuming column chromatography is not required for purification. Thus far, two versions of the Nb-CD monomer (with n=1 or 3 for the aliphatic tether lengths) shown in FIG. 6 were synthesized, and the synthesis of the Nb-TC[4]A and Nb-LARGE monomers was started. It is important to note here, that if needed, the synthetic methods can enable the production of a library of monomer analogs, which can allow for tuning the properties of the final copolymer and micelle.

Next, binding studies were carried out to show that Nb-CD has a high affinity towards known clinical antibiotics. This study was conducted by carrying out titrations in water where several different antibiotics were slowly added (see e.g., FIG. 7A) into dilute solutions (0.5 mM) of the (n=3) CD-based monomer. The progress of the titrations was monitored using proton nuclear magnetic resonance ($^1$H NMR), and the $K_a$ was calculated using a non-linear regression analysis. The binding data ($K_a$) for each antibiotic $\supset$ Nb-CD complex is shown directly under each chemical structure in FIG. 7A, and a representative binding titration curve ($\Delta$ppm vs. [Guest]) is shown in FIG. 7B. It was concluded from this binding study that the Nb-CD monomer is capable of binding a wide variety of small-molecule antibiotics that range from β-lactams such as amoxicillin (bactericidal, cell wall synthesis inhibitor), or sulfonamides like sulfadiazine (bacteriostatic agent, inhibits the enzyme dihydropteroate synthase), to tetracycline (bacteriostatic, disrupts protein synthesis). This level of binding promiscuity indicates the ability to polymerize several pre-loaded Nb-CD monomers in precise (potentially synergistic) ratios with other monomers.

TMS-Py-TC[4]A (see e.g., FIG. 8A), a precursor to the monomer Nb-TC[4]A was successfully synthesized. This is a new derivative for TC[n]A receptors in general since it consists of two additional thioether bridges that are linked by a pyridine ring on the lower rim of the macrocycle. The addition of this thioether-pyridine bridge effectively increases the binding of Ag$^+$ inside the receptor cavity by an order of magnitude, while also providing a useful functional handle onto which it is planned to couple the polymerizable norbornene group. To quantify the binding between Ag$^+$ and TMS-Py-TC[4]A, another $^1$H NMR titration was carried out where the host was present at 0.5 mM in a deuterated tetrahydrofuran (THF-d$_8$) solution, and the guest was added in 0.1 equivalents as a concentrated aqueous AgNO$_3$ solution. The results from this titration (see e.g., FIG. 8B) indicate that in a predominantly organic solvent like THF, the TMS-Py-TC[4]A derivative exhibits a high affinity (~1× $10^5$ M$^{-1}$) for Ag$^+$. This is advantageous because it implies that the polymerization can be carried out in THF or dimethylformamide (DMF) to make the block copolymer of Nb-CD and Nb-TC[4]A, where each supramolecular monomer is preloaded with their respective cargoes that will remain inside the host cavity during polymerization and subsequently during dialysis against either THF or DMF.

These preliminary binding studies are promising and suggest that Nb-TC[4]A will also be able to carry the Ag$^+$ payload with the desired binding affinity. Moreover, the disclosed synthetic strategy to make Nb-TC[4]A, where the phenolic R groups can be converted into useful metal binding ligands, for example, will allow us to optimize the properties of the Ag$^+$ receptor as needed.

Figure 9:
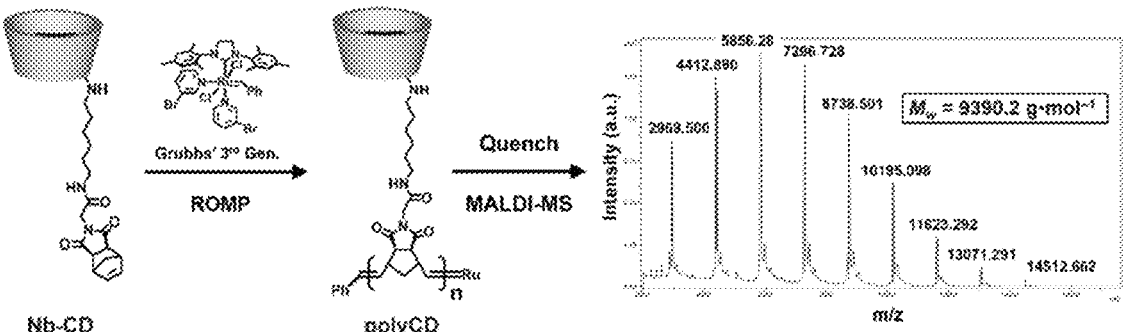
FIG. 9. (A) ROMP of Nb-CD using Grubbs' 3rd generation catalyst to generate polyCD. (B) Matrix-assisted laser desorption/ionization mass spectrometry (MALDI-MS) data for polyCD.
Figure 10:
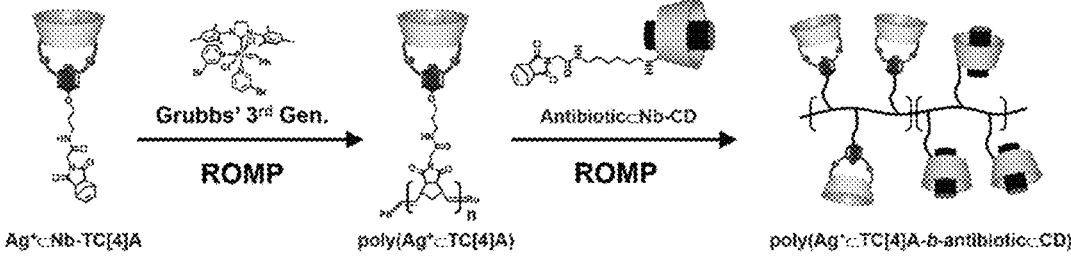
FIG. 10. ROMP of $Ag^+ \subset$ Nb-TC[4]A and antibiotic $\subset$ Nb-CD using Grubbs' 3rd generation catalyst to generate poly (Ag+$\subset$TC[4]A-b-antibiotic$\subset$CD).

(II) Establishing the Ring-Opening Metathesis Polymerization of Ag$^+$/Drug-Loaded Monomers, Cytotoxicity, and Release Kinetics Each functional monomer was designed to have an N-alkyl-5-exo-norbornene-2,3-dicarboxylic acid imide group (Nb for short) since it possesses a ring-strained double bond that is very reactive in the presence of ruthenium-based catalysts, such as Grubbs' 1$^{st}$-3$^{rd}$ generation catalysts. This strategy is ideal since the initiation and propagation kinetics associated with the polymerization are typically very fast and often high molecular weight polymers can be obtained in a few hours or less. Based on this, it was first attempted to synthesize (see e.g., FIG. 9A) the CD-based homopolymer (polyCD), where only the catalyst and Nb-CD monomer were added together in DMF at moderate monomer concentrations (~50 mM). This polymerization reaction yielded a polymer with a weight-average molecular weight (M$_w$) of 9390.2 g·mol$^{-1}$ (see e.g., FIG. 9B) and a moderate dispersity (Đ) value of 1.148, which is a measure of the molar mass distribution of a batch of polymers. Optimization of this polymerization continues to prepare even higher molecular weight polymers with narrower dispersity values. This early result is very encouraging and suggests that the polymerization to make the diblock copolymer (poly(TC[4]A-b-CD) is feasible. Once the synthesis of Nb-TC[4]A is finished, a polymerization screen will be set up to make the diblock copolymer, where Nb-CD and Nb-TC[4]A are mixed in a 1:1 ratio in the presence of Grubbs' 3$^{rd}$ generation catalyst, and the polymerization kinetics and molecular weight outputs as a function of solvent, temperature, and monomer-to-catalyst ratio will be assessed. Once the copolymerization conditions have been optimized using the unloaded monomers, each monomer will be loaded with their respective cargoes—i.e., antibiotic $\supset$ Nb-CD and Ag$^+$ $\supset$ Nb-TC[4]A—and carry out the polymerization (see e.g., FIG. 10) using the same conditions.

After the Ag$^+$/drug-loaded diblock copolymer has been synthesized successfully, the cytotoxicity of the loaded and unloaded two-component polymer will be measured at different concentrations against healthy mammalian cells-specifically, human umbilical vein endothelial cells (HU-VEC)—which will be quantified using a luminescent cell viability assay called CellTiter-Glo®. These experiments will be carried out in a BSL-2 cell culture laboratory and will quickly allow us to determine the concentration of copolymer that results in a lethal dose of 50% (LD$^{50}$) of the HUVECs. Having carried out these types of cell viability experiments on other polynorbornene-based anticancer drug delivery systems it is believed that it is possible to go to relatively high concentrations of polymer before appreciable toxicity is observed.

In addition to measuring the cytotoxicity of the two-component platform, the rate of release of each of the respective guests (i.e., Ag$^+$ and antibiotics) will also be characterized. The latter experiment can be carried out in a straightforward manner, whereby a known concentration of the loaded diblock copolymer poly(Ag$^+$ $\supset$ TC[4]A-b-antibiotic $\supset$ CD) will be dissolved in either THF or DMF and place this polymer solution in a dialysis bag (with molecular weight cutoff=1000 g·mol$^{-1}$). Next, the dialysis bag will be placed in a 1 L beaker containing a phosphate buffered saline (PBS) solution, which will diffuse into the dialysis bag and saturate the polymer in an aqueous environment. The release of the Ag$^+$ will be monitored by taking aliquots from the outer PBS solution and subjecting the sample to inductively coupled plasma mass spectrometry (ICP-MS). Likewise, the amount of antibiotic that is released will be assessed by taking an aliquot from the surrounding PBS solution and quantifying the concentration of released drug by using internal standards and basic techniques such as $^1$H NMR, UV-Vis, and LC-MS. The concentrations of the released ions and drugs will be plotted as a function of time and the release profile will help identify the ratios of the two components that are present at any given time. Moreover, since the synthesis to make the supramolecular monomers is very modular—especially in the case of the Nb-TC[4]A monomer where the upper rim can be functionalized with any additional metal binding ligand derivatives—the release of the Ag$^+$ will be tunable relative to that of the small-molecule antibiotics, which could have great implications in terms of releasing synergistic vs. additive ratios of the antimicrobial/antibiotics.

Figure 11:
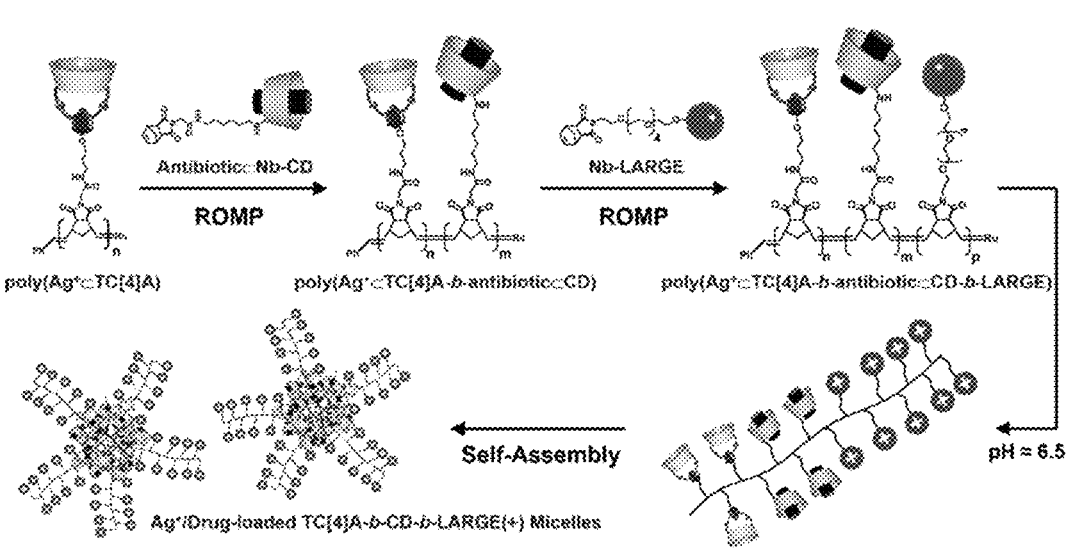
FIG. 11. Sequential ROMP of each monomer gives the triblock copolymer poly(Ag+$\subset$TC[4]A-b-antibiotic$\subset$CD-b-LARGE), which upon protonation, can self-assemble into micellular nanomaterials based on the differences in polarity between the blocks. The design adopts a core-shell morphology that places the antimicrobial/antibiotics in the core and the positively charged groups (red spheres) facing outwards to selectively target bacteria.
Figure 12:
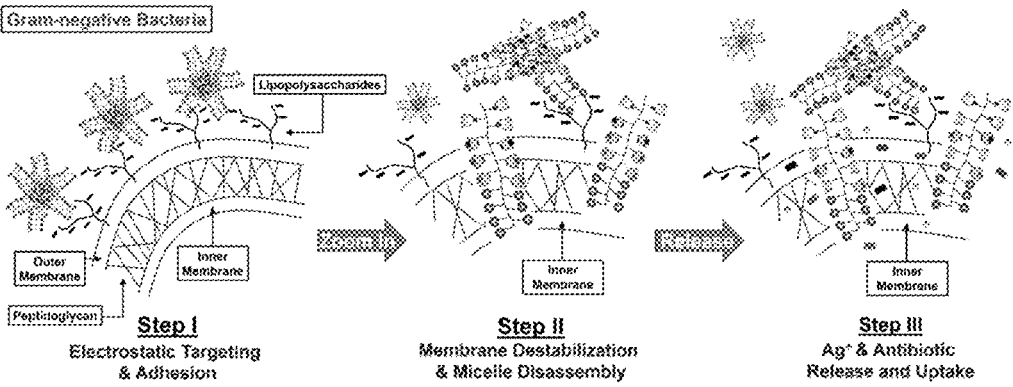
FIG. 12. Three-step mechanism of adhesion to outer cell membrane of gram-negative bacteria followed by membrane destabilization, micelle disassembly, and ultimately the release of the $Ag^+$ and antibiotics into the cell.

(III) Synthesis and Self-Assembly of the Triblock Copolymer, and Assessment of its In Vitro Efficacy and Ability to Overcome Resistance in MDR Strains of Bacteria The last phase of the research builds on the first two by adding in a third functional block to the copolymer—originating from the so-called Nb-LARGE monomer (see e.g., FIG. 11)—that, upon protonation of the arginine subunit, can induce self-assembly of the triblock copolymer into micellular-based nanomaterials (as a consequence of polarity differences between the blocks), while also serving as a targeting agent capable of adhering to, and punching holes in, the cell membranes of bacteria (see e.g., FIG. 12). This micellular morphology will help protect the drug cargo in its core, while also projecting outwards the positively charged LARGE moieties that allow for adhesion to bacterial cell membranes. Additionally, it has been reported that arginine-functionalized glucosamine can disrupt biofilms and promote collagen synthesis: two key properties which are ideal for wound healing. The synthesis of the Nb-LARGE monomer can be theoretically achieved in five steps and its polymerization onto the diblock copolymer poly($Ag^+ \subset TC$ [4]A-b-antibiotic $\subset CD$) to give the triblock copolymer poly ($Ag^+ \subset TC$[4]A-b-antibiotic $\subset CD$-b-LARGE) is possible because ROMPs behave as 'living' reactions, which means that the active ruthenium carbene at the end of the growing polymer chain will continue to react with any additional monomers that are added, at least until the polymerization is finally quenched, typically with ethyl vinyl ether.

This supramacromolecular strategy affords a general platform that combines an antimicrobial in the form of $Ag^+$ with that of almost any number and combination of appropriately sized small-molecule antibiotics, a favorable pairing which makes it possible to repurpose 'old' antibiotics that certain bacterial strains may have developed a resistance to. Moreover, this combination platform is unique from traditional drug delivery systems in that only a single monomer (Nb-CD) need be synthesized in order to load onto one platform several different types of antibiotics that possess orthogonal mechanisms of action towards MDR bacteria. The introduction of the Nb-LARGE monomer further enhances the capabilities of the combination antimicrobial platform (see e.g., FIG. 12), whereby the micelles (which will be characterized by dynamic light scattering) first adhere electrostatically to the negatively-charged surface of the bacterial cells, followed by disassembly of the micelle into individual triblock copolymers. Since the triblock copolymers will be localized at the cell surface, which is being disrupted by the polycationic LARGE block, the slow release of the $Ag^+$ and antibiotics from the 'smart' receptors stand a high probability of being taken up by the bacteria. This approach allows for the re-use of several different antibiotics simultaneously.

The combination platform will be evaluated against MDR Gram-positive bacteria, such as methicillin-resistant *S. aureus* (MRSA), as well as MDR Gram-negative bacteria, such as *P. aeruginosa*, *E. coli*, and one of the CDC's most urgent threats, NDM-1 producing carbapenem-resistant Enterobacteriaceae, which will be treated using the described platform loaded with $Ag^+$, Imipenem, and thiol NDM-1 Inhibitor, a potentially potent combination. The in vitro efficacy of the combination micellular platform will be assessed by challenging each bacterial cell line over 1, 12, 24, 48, and 96 hr, and after plating on agar plates, the number of colony forming units (CFU) will be counted to assess the overall bactericidal properties. Additionally, disc diffusion experiments will be carried out, where a filter paper disc is impregnated with the combination platform and then placed on agar plates that have been inoculated with the specific MDR bacteria. The zone of inhibition can be measured for different combinations, and moreover, the length of time that the discs are capable of killing, or preventing growth of, the MDR bacteria will be assessed. This latter property is important to quantify since one of the intended goals of the platform is to be able to slowly release the different cargo combinations over extended periods of time-preferably days, if not weeks, which is on par with the rates associated with healing of severe wounds. Lastly, the combination platform will be evaluated by carrying out a liquid culture study with the micelles directly in solution with the MDR bacteria, versus the polymeric micelle in a dialysis bag in the presence of the bacteria. This latter experiment would serve as a control to determine what effect the polycationic LARGE block will have in killing bacteria relative to what the other drugs contribute.

Larger antibiotics like glyco- and lipo-peptides can be too large to fit inside the cavity of β-CD. But, by functionalizing the larger drugs with adamantane groups or other hydrophobic groups can allow for docking or anchoring, of larger drugs inside the CD cavity. Furthermore, there are still entire classes of antibiotics of appropriate size that can be encapsulated by the β-CD-based monomer, such as β-lactams, aminoglycosides, quinolones, chloramphenicol, sulfonamides, and tetracyclines. Moreover, the strategy of using $Ag^+$ to repurpose 'old' antibiotics increases the total number of antibiotics that may now be effective using the combination platform strategy.

The timing of when the drugs are added to the supramolecular monomer hosts could be important. For example, the first approach will consist of polymerizing the pre-loaded monomers, however, if it is learned that a high percentage of drug cargo is released prematurely during the polymerization and dialysis steps, then the loading the $Ag^+$/antibiotics will be investigated post-polymerization since the Nb-TC [4]A host cavity is half as large as that of Nb-CD.

Here is described the development of a nearly universal 'plug-and-play' technology for the delivery of a wide variety of small-molecule drug combinations, and in particular antibiotics that at some point along the way have been deemed ineffective as a consequence of the rapid rise of antibiotic resistance in the world. Thus, any medical professional could choose a drug combo for a specific target pathogen and/or resistance factor, and treat a patient using the presently disclosed combination platform. The disclosed multi-functional combination antimicrobial platform could lead to a new non-toxic and broad-spectrum treatment option for infectious MDR bacteria that can be utilized for post-surgical wound healing and battlefield applications, and in the very least it would establish new fundamental designs in the drug delivery arena that could potentially solve some of the longstanding challenges that plague this field, such as early release of potentially toxic drug combinations, or no release at all because the environmental trigger fails in an in vivo setting.

The studies herein are innovative and has the potential to greatly impact simultaneously many different fields of research and medicine. Currently, there is still no method that can precisely pair $Ag^+$ and multiple antibiotics using a single platform. Moreover, there is not a clean method for the controlled release of the antimicrobial and the antibiotic of choice over an extended period of time. The presently described combination platform solves both of these issues. Also, this single-antibiotic-binding monomer approach opens up a plethora of possibilities in terms of the number of small-molecule antibiotics that can be combined without having to synthesize a new monomer. This means that pre-loaded Nb-CD monomers could be stored for long periods of time and quickly polymerized in whatever combination is required for a particular infection, or thinking more broadly, this technology makes possible the idea that a combination antimicrobial micelle could be prepared with $Ag^+$, three or more antibiotics, and the targeting/antimicrobial component, and then stored, waiting for when an individual has been infected with a lethal MDR bacteria and there is little to no time to test 26 different antibiotics before the infection turns fatal. Lastly, there are many structural similarities between some antibiotics and anticancer drugs, which means that this technology could also be beneficial for the delivery of combinations of incredibly toxic anticancer drugs, such as those that are currently used to treat pancreatic cancer. Overall, the chemistry has the potential to introduce new fundamental knowledge in the areas of polymer and supramolecular chemistries, as well as in the treatment of infectious pathogens, and possibly for the treatment of aggressive forms of cancer.

Example 3: Combating Multidrug Resistant Bacteria: A Supramolecular Block Copolymer Approach for Synergistic Release of Silver Ions and Antibiotics The following example describes combating multidrug resistant bacteria: a supramolecular block copolymer approach for synergistic release of silver ions and antibiotics.

(1) Biocompatible, Combination Antimicrobial and Hemostatic Micelle

Figure 13:
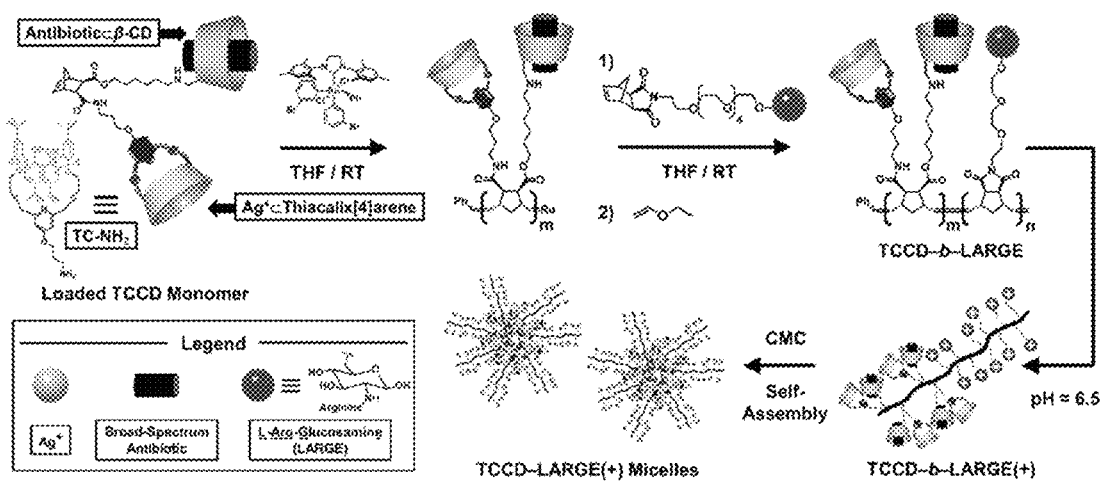
FIG. 13. Synthesis and self-assembly of the polymer-based combination antimicrobial platform.

The first strategy to synthesize (see e.g., FIG. 13) a biocompatible, combination antimicrobial and hemostatic micelle capitalizes on the functional-group tolerant ruthenium-catalyzed method of ring-opening metathesis polymerization (ROMP) of functional norbornene-based monomers. The first monomer (see e.g., FIG. 13, top left) is hydrophobic and consists of two orthogonal macrocyclic receptors—namely, a tert-butyl-thiacalix[4]arene (TC) derivative and a mono-functionalized β-cyclodextrin (CD), a so-called TCCD monomer. The second monomer (see e.g., FIG. 13, blue sphere) consists of a hydrophilic norbornene-hexaethylene glycol capped with an N-L-arginine-glucosamine subunit (referred to hereafter as LARGE monomer), which will function as the outer shell of the self-assembled micelle, and will be responsible for establishing the electrostatic interaction with the negatively charged moieties on the surface of Gram-negative bacteria and will also help induce collagen synthesis during wound healing. Once synthesized, the branched TCCD monomer will be loaded with $Ag^+$ (from $AgNO_3$) and a water-soluble broad-spectrum antibiotic, such as tetracycline, in a 75:25 THF:$H_2O$ solvent mixture, followed by precipitation using copious amounts of diethyl ether ($Et_2O$). The issue of cross-loading the drug and $Ag^+$ into the two different receptors is negated by the fact that cyclodextrin in general prefers to bind in its cavity only hydrophobic substrates (e.g., the majority of the chemical surface area of tetracycline), while the thiacalix[4]arene derivative described herein can bind positively charged ions with several orders of magnitude greater affinity than it binds hydrophobic moieties as a consequence of the soft-soft thiol-silver interactions. After each receptor of the TCCD monomer has been loaded with their respective cargo—which will be characterized in solution using the individual macrocycles and compared to the branched TCCD monomer—it will undergo ROMP (see e.g., FIG. 13) using Grubbs' third-generation ruthenium catalyst in non-polar tetrahydrofuran (THF) solvent to synthesize the first block, followed by the addition of the LARGE monomer to add onto the ruthenium end of the "living" polymer. This synthetic strategy will produce the desired block copolymer (TCCD-block-LARGE; FIG. 13, top right) before the ruthenium catalyst is quenched with either ethyl vinyl ether or a vinyl fluorophore for in vitro tracking purposes. Finally, the block copolymer brushes can self-assemble (see e.g., FIG. 13, bottom middle) into micelles above the critical micelle concentration (CMC) after protonation of the guanidine functional groups of the LARGE subunits and the addition of water to the copolymer in a residual amount of THF. These micelles may even be lyophilized in the presence of 5% glucose solutions in order to store them for long periods of time before use as either a wound cleansing agent in phosphate buffered saline (PBS) solutions, or as the antimicrobial ingredient in a hemostatic chitosan-based bandage.

One of the advantages in using ROMP with multifunctional monomers as a means to construct the block copolymers is that the process is highly modular. In other words, if the preferred ratio of the antimicrobial agents needed to be changed to ensure synergy, then either the loading ratio would be changed, or structurally speaking, the norbornene-based monomers can be synthesized such that each macrocyclic receptor is its own monomer. Thus, the ratio of the antimicrobial agents can be controlled easily by varying the stoichiometry of the individual monomers during the ROMP step. Also, the degree of polymerization (DP) can be controlled by setting the monomer stoichiometry against the amount of catalyst. The control over DP is advantageous because a longer hydrophobic block may be necessary to induce micellar formation. These features make this approach highly modular and can allow for personalized combinations of antimicrobials to treat against specific infectious pathogens.

Finally, the biocompatibility of these types of polynorbornene backbones have been evaluated previously in highly positively charged antimicrobial systems from Tew and co-workers, as well as in the delivery of anti-cancer drugs by Johnson and co-workers for the purposes of treating aggressive forms of ovarian cancer. Nonetheless, the cytotoxicity of the individual monomers (loaded and unloaded), as well as the final micelles, will be evaluated by carrying out an MTT cell viability assay on different human primary cells and cell lines. The bactericidal capability of the dual-loaded micelles will also be evaluated against standard Gram-negative bacterial cells, such as *E. coli, P. aeruginosa*, and a quaternary-amine-resistant bacterial strain *Ralstonia* sp. as a control. After challenging each cell line with the antimicrobial micelles for 1, 12, 24, 48, and 96 hr, the number of colony forming units (CFU) will be counted to assess the ability of the dual-loaded system to kill Gram-negative bacteria.

(II) Development of a Dual-Tube Syringe

Figure 14:
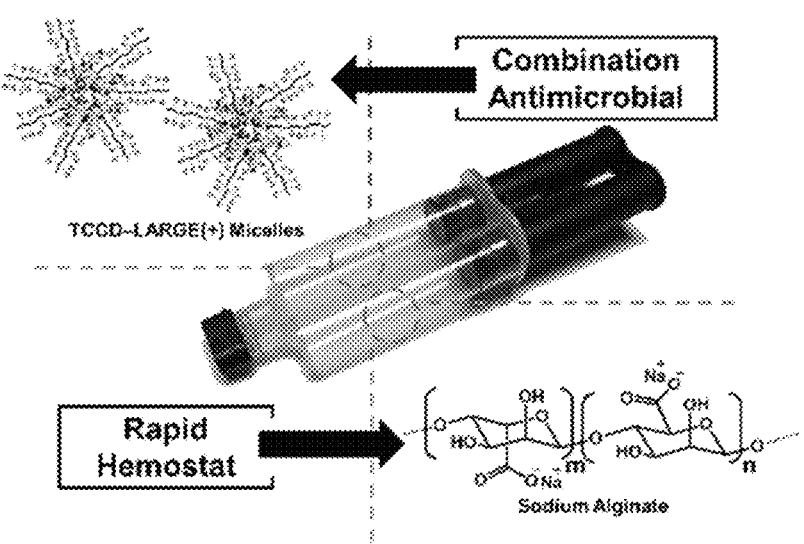
FIG. 14. A dual-syringe system for co-delivery of the combination antimicrobial platform and sodium alginate, which is a rapid hemostat.
Figure 15:
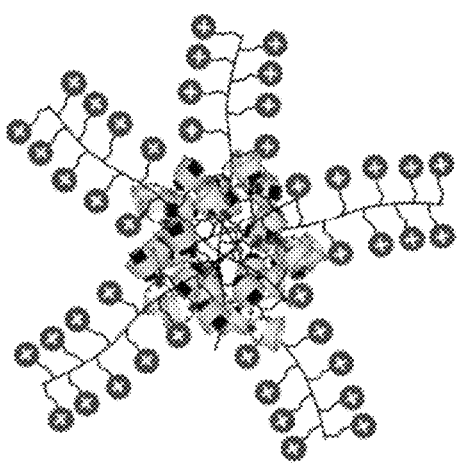
FIG. 15. Loaded micelle.

Hemorrhaging from a truncal injury during wartime efforts is one of the leading causes of death on the battlefield. Due to the location and nature of the injury, it is not possible to place a tourniquet or small bandage on this type of wound to prevent further blood loss. Therefore, a quick and injectable hemostatic material is necessary to stem the bleeding, while also serving as an antimicrobial to stave off bacterial infections of the open wound. The disclosed supramolecular combination platform can help function as the antimicrobial and wound healing components of such an injectable material, however, in the case of severe injury to the torso, a rapid water-absorbing material is necessary to aid thrombosis. Therefore, described here, is a dual-tube syringe (see e.g., FIG. 14), much like those used for the industrial use of epoxy resins. One of the tubes will contain a PBS solution comprised of the combination antimicrobial material (polymer-based drug-delivery agent), while the second tube will consist of a gel of biocompatible and FDA-approved sodium alginate, which has been moderately hydrated to allow for it to flow out of the tube. Dispensing the contents separately from each tube into the open wound will lead to rapid activation of the coagulation cascade on account of the alginate absorbing multiple times its starting weight in water. This mixture will allow for stoppage of bleeding as well as prolonged protection from harmful infectious microbes, allowing the wound to heal properly. This system will be tested first in swine-based ballistics gelatin, before being investigated in vivo in live animal models.

These studies describe a highly modular supramolecular antimicrobial platform capable of controlled loading and sustained release of synergistic ratios of $Ag^+$ and a variety of broad-spectrum antimicrobials. These studies will also assess the affinity, enthalpy, and entropy associated with the binding of silver ions and small-molecule antibiotics inside the cavity of the supramolecular receptors that are part of the delivery platform. Additionally, the kinetics associated with the binding and release of the drugs can be analyzed so that time points can be identified for ideal (i.e., synergistic) concentrations of each antimicrobial agent are present and therefore the most potent. Isothermal titration calorimeter (ITC) will be used that can quantify the aforementioned thermodynamic parameters, and their fluorescence lifetime spectrometer that will reveal the kinetics associated with the binding and release stages.

Example 4: Supramolecular Strategy to Combat Multidrug-Resistant Bacteria

Figure 16:
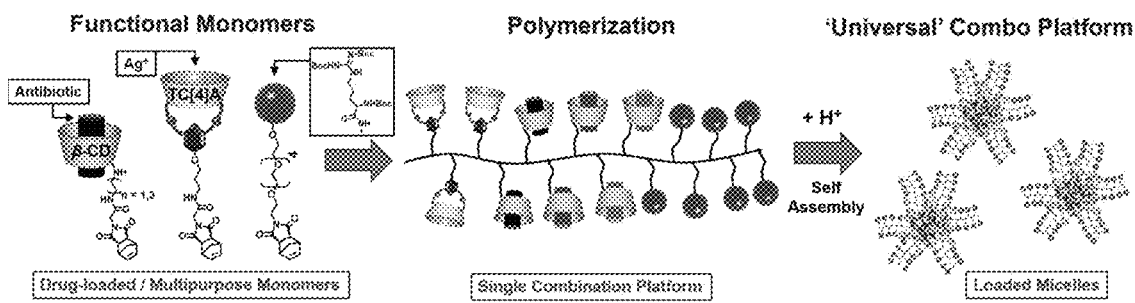
FIG. 16. Supramacromolecular strategy to combat multi-drug-resistant bacteria resulting in a 'universal' combination platform.
Figure 17:
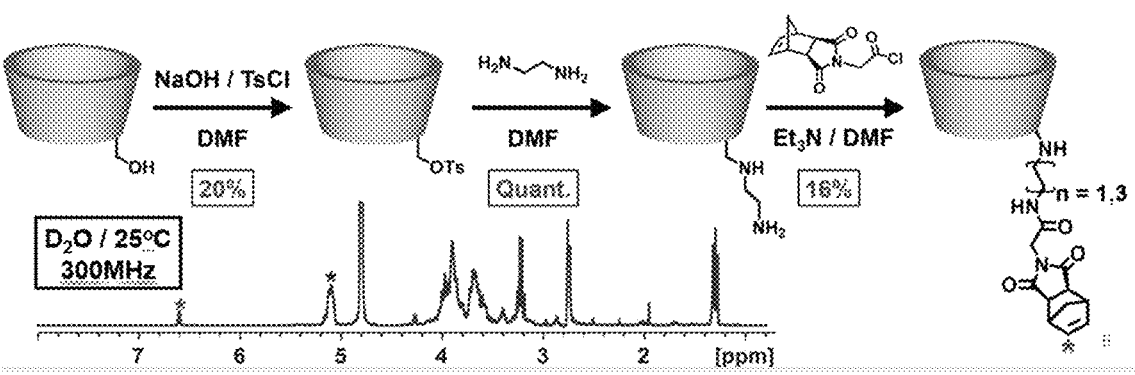
FIG. 17. Nb-cyclodextrin (Nb-CD) synthesis.
Figure 18:
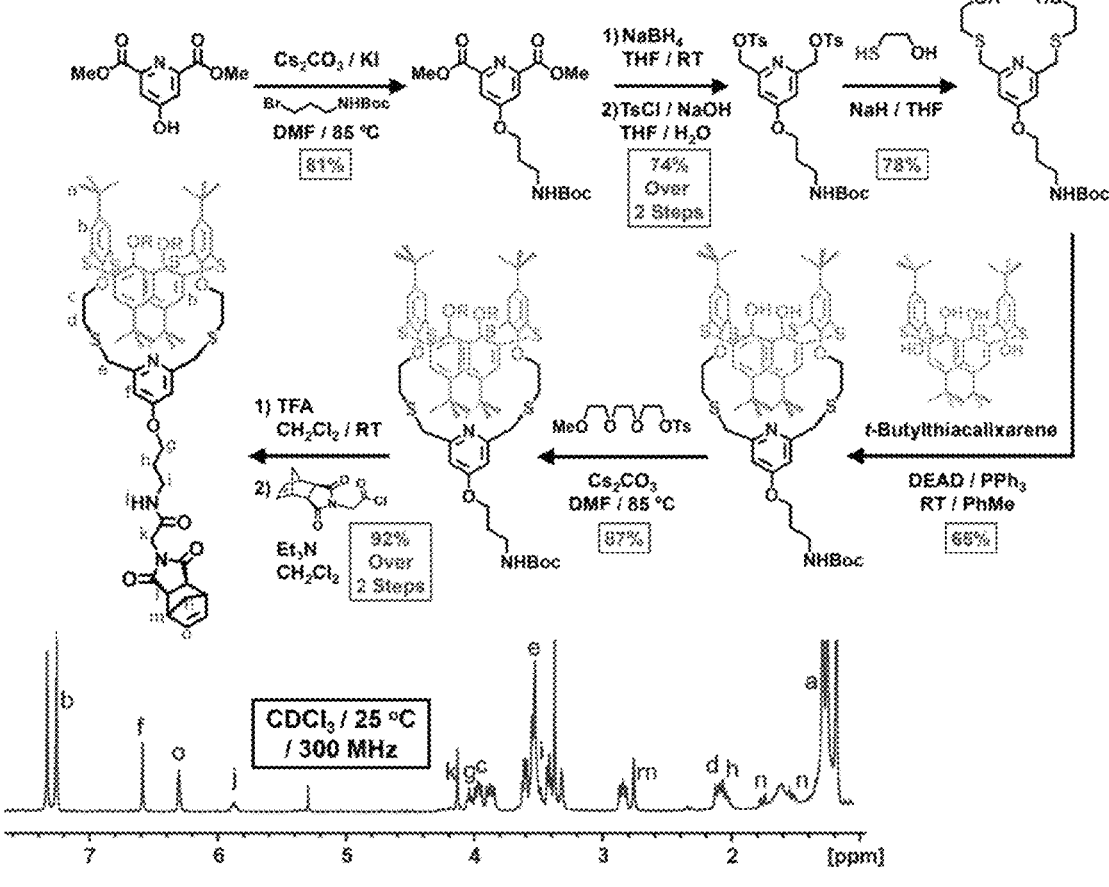
FIG. 18. Nb-Thiacalix[4]arene (Nb-TC[4]A) synthesis.
Figure 19:
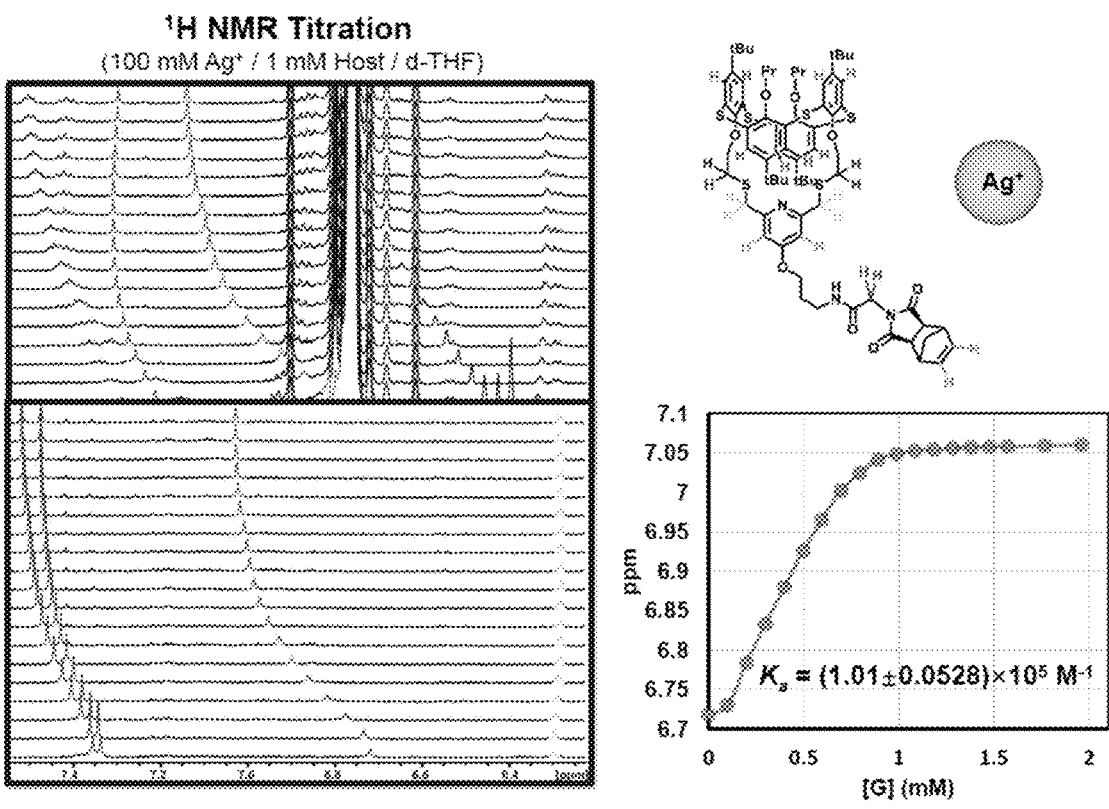
FIG. 19. Thiacalixarene-monomer $\supset$ Metal ion ($Ag^+$).

The following example describes a supramolecular strategy to combat multidrug-resistant bacteria. Here, is described a supramacromolecular strategy to combat multidrug-resistant bacteria (see FIG. 16).
Design, Synthesis, and Properties of Functional Monomers
Monomer Design and Properties are illustrated in FIG. 6. Three functional monomers were synthesized: Nb-Cyclodextrin (Nb-CD) (see e.g., FIG. 17), Nb-Thiacalix[4]arene (Nb-TC[4]A) (see e.g., FIG. 18) and Thiacalixarene-monomer ⊃ Metal ion ($Ag^+$) (see e.g., FIG. 19), and cyclodextrin-monomer ⊂ Antibiotic (see e.g., FIG. 20).

Figure 20:
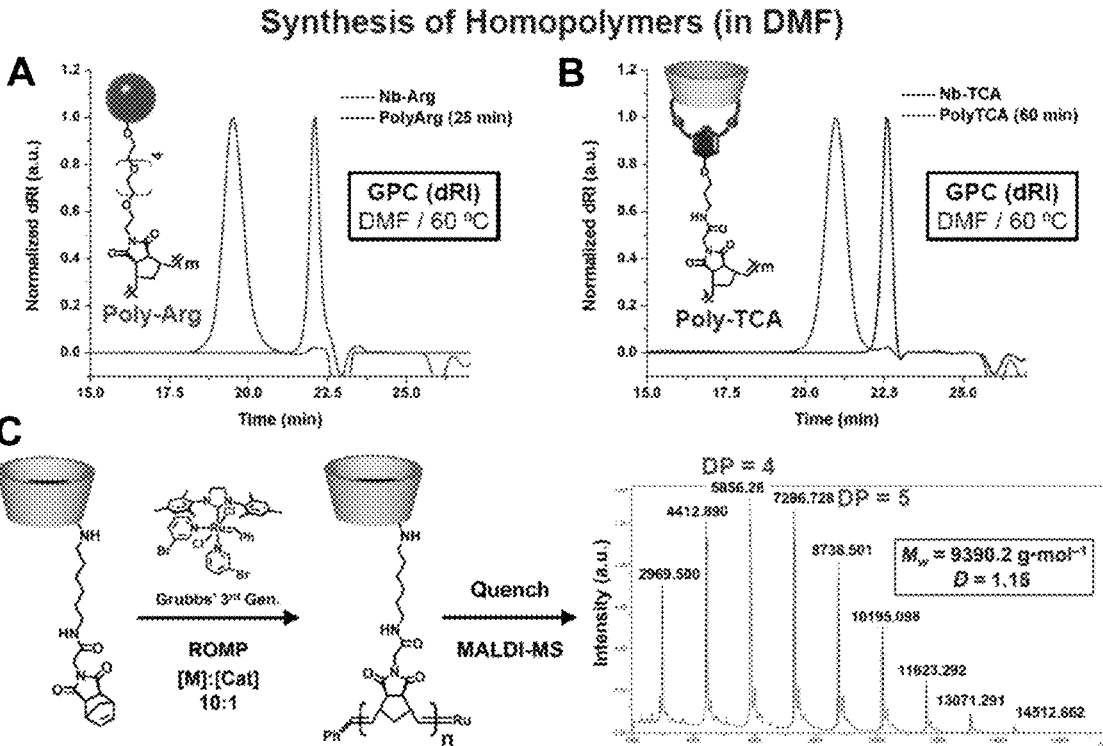
FIGS. 20. (A and B) Synthesis of homopolymers (in DMF). (C) Polymerization scheme to make polyCD from Nb-CD. The spectrum on the right indicates the molecular weight and mass distribution of the initial polyCD.
Figure 21:
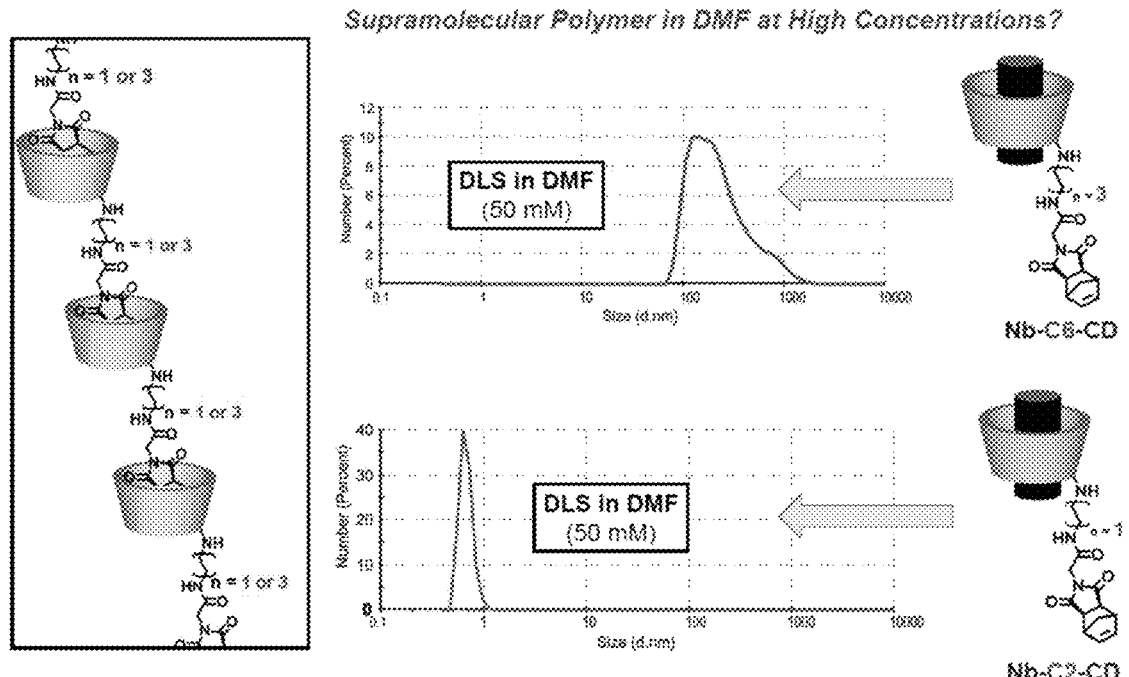
FIG. 21. Supramolecular polymer in DMF at high concentrations.
Figure 22:
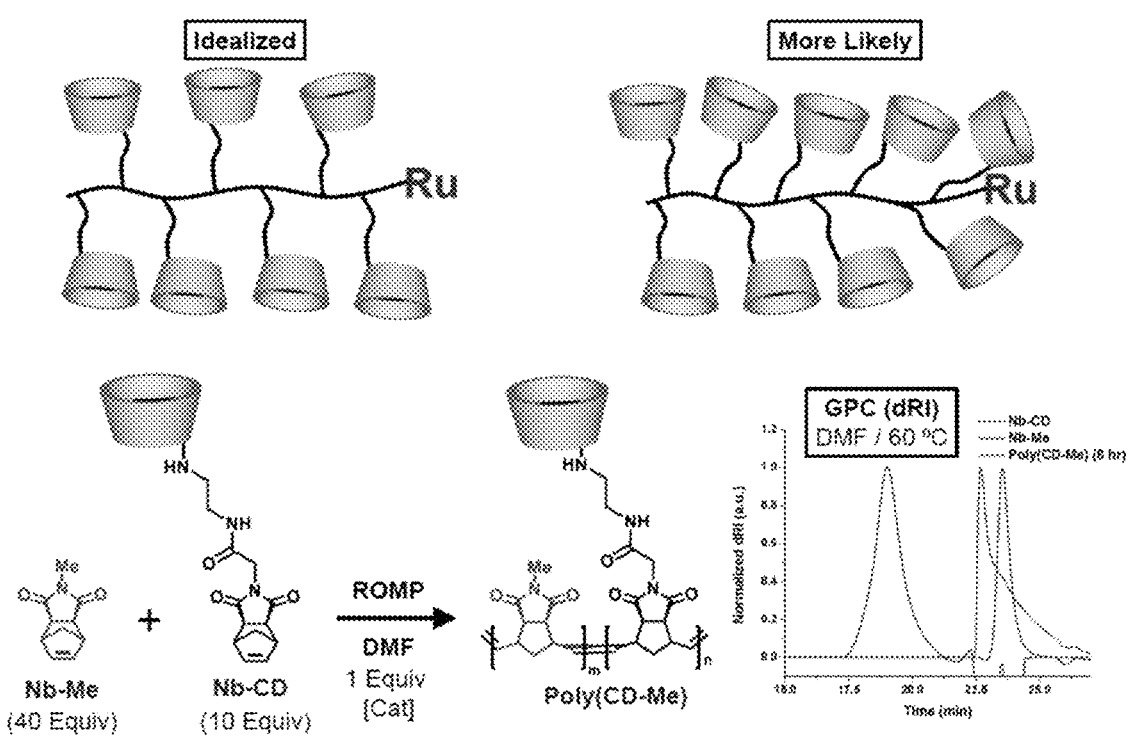
FIG. 22. Steric crowding of growing chain end.
Figure 23:
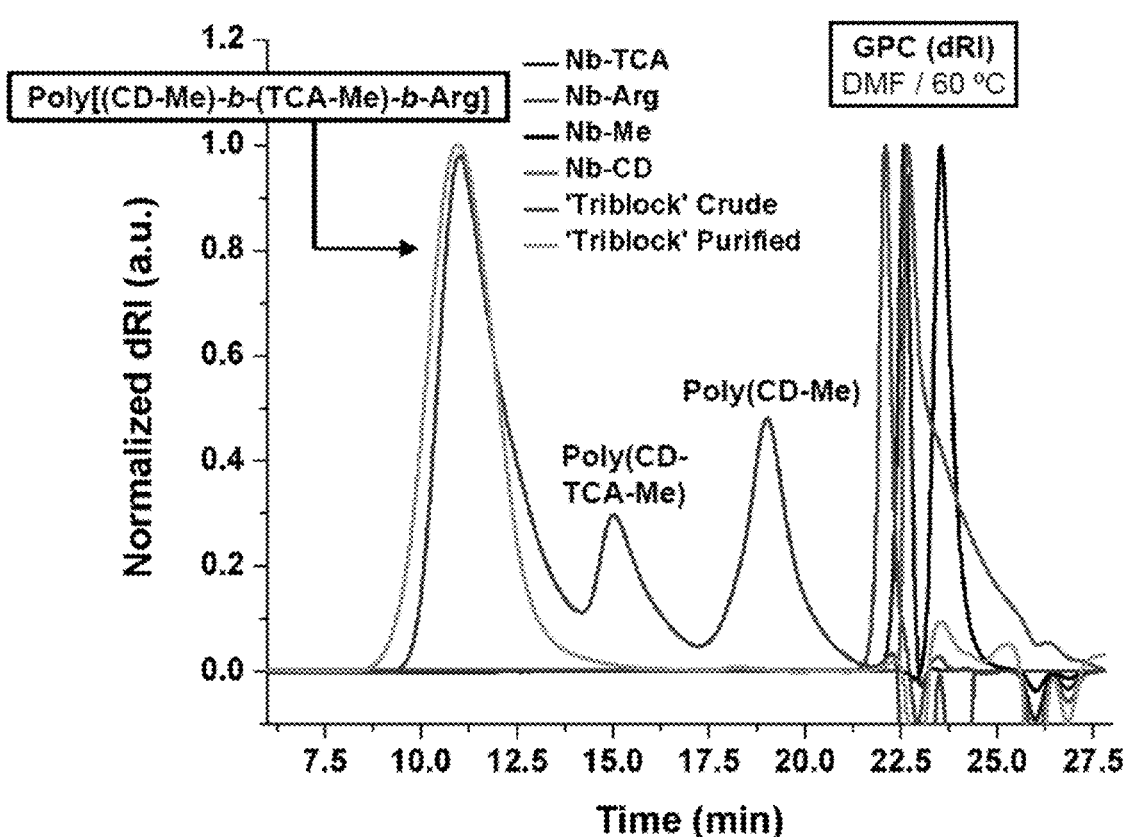
FIG. 23. Synthesis of a 'triblock' copolymer.

Host-guest binding properties of supramolecular monomers were tested with various antibiotics. Antibiotics bound to a cyclodextrin monomer were Amoxicillin ($K_a$=6700±1000), Levofloxacin ($K_a$=71.1±1.5), Linezolid ($K_a$=100.1±1.1), Sulfadiazine ($K_a$=2700±110), Sulfamethoxazole ($K_a$=260.2±4.1), and Tetracycline ($K_a$=422.0±15).
Polymerization of Functional Monomers
Synthesis of homopolymers (in DMF) is shown in FIG. 20. Synthesis of a 'triblock' copolymer (poly[(CD-Me)-b-(TCA-Me)-b-Arg]) is shown in FIG. 23. FIG. 24 shows an illustration of the poly[(CD-Me)-b-(TCA-Me)-b-Arg] and the loading of $Ag^+$ and an antibiotic (e.g., Amoxicillin) into the poly[(CD-Me)-b-(TCA-Me)-b-Arg] (and deprotection thereof with TFA).

In vitro efficacy against bacterial clinical isolates were measured. Gram negative: *E. coli* (see e.g., FIG. 25) and gram positive: *S. Aureus* (see e.g., FIG. 26) were tested with various loading levels of loaded and unloaded polymer, $AgNO_3$, and antibiotic controls.

Example 5: A Novel Supramacromolecular Approach to Non-Toxic Combination Anti-Cancer Therapeutics The following example describes a novel supramacromolecular approach to non-toxic combination anti-cancer therapeutics.

To overcome major challenges of anticancer agent toxicity, described here, is the development of a next-generation universal plug-and-play drug delivery system comprised of linked supramolecular monomers that act as 'smart' receptors for a wide variety of small-molecule anti-cancer drugs that can be polymerized together in precise monomer ratios to yield combination drug-loaded nanoparticles. This 'supramacromolecular' approach (see e.g., FIG. 28) will completely bypass any issues associated with prodrug-to-drug conversion in vitro/vivo because the unmodified drug itself will be what is loaded into the receptors that are positioned along the polymer chain, and therefore the drug's mechanism of action will remain undistorted. Additionally, the small-molecule drugs will not need an external event in vitro/vivo to trigger their release from the platform, but rather the release will be governed by the non-covalent binding interactions between the receptor and the drug. In other words, it is possible to accurately characterize the binding affinity constant ($K_a$), as well as the release kinetics, for each receptor-drug combination, and thus predict the exact concentrations of a combination of drugs that are released into the local environment at any given time, so long as the temperature, pH, and salt concentration of the surrounding environment or media is known. This supramacromolecular strategy (see e.g., FIG. 28) will result in a general platform for personalized medicine, where any desired combination of small-molecule anti-cancer drugs can be implemented to treat a particular type of cancer.

Figure 29:
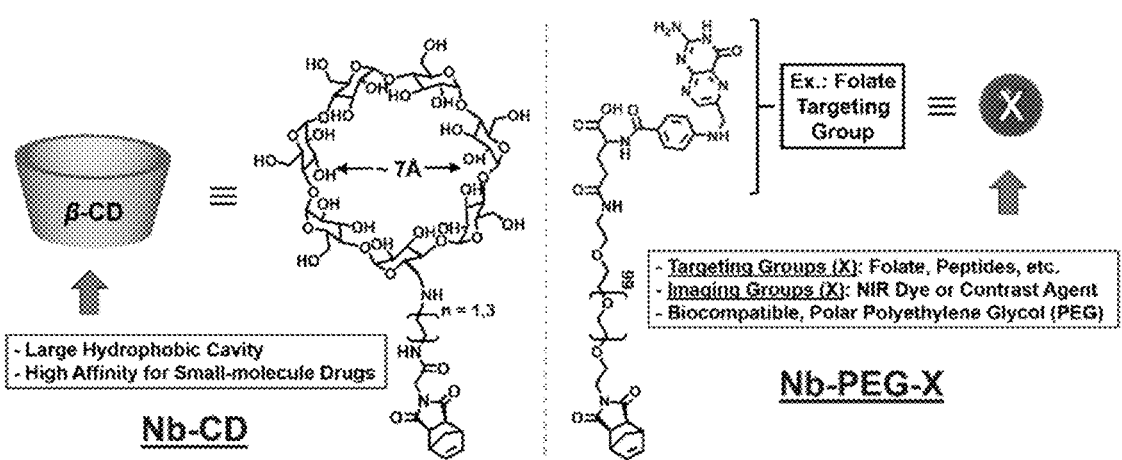
FIG. 29. The design of two functional monomers: a norbornene-based β-cyclodextrin monomer (Nb-CD) and a norbornene-PEG-targeting/imaging monomer (Nb-PEG-X), and their corresponding properties.

The three aims of the disclosed studies are illustrated in FIG. 28. (I) Monomer Development, entails the synthesis of two key monomers, one which has a β-cyclodextrin macrocycle attached to it that can house hydrophobic small-molecule drugs, and the other which is comprised largely of polyethylene glycol (PEG)—a biocompatible and biodegradable polymer approved by the FDA—that can be end-functionalized with either targeting or imaging moieties to help actively direct the nanoparticle to the site of cancerous tissue, and/or allow for tracking of the nanoparticles by way of near-IR dyes or MRI contrast agents. (II) Copolymerization, involves the polymerization of each monomer together into a single platform. (III) Universal Combo Platform, describes being able to load three or more different types of anti-cancer drugs into a single platform using a single supramolecular monomer, which will be combined with the targeting/imaging PEG-based monomer, and the 'living' copolymer crosslinked into drug-loaded nanoparticles that will be assessed in vitro.
(I) Design, Synthesis, and Properties of the Functional Monomers
The Nb-CD monomer shown in FIG. 29 was recently synthesized. The monomer has a hydrophobic cavity that spans 7 Å at its widest point, which is the perfect size to bind hydrophobic small-molecule anticancer drugs. The other functional monomer depicted in FIG. 29 is a long PEG chain functionalized with a polymerizable norbornene group on one end and either a targeting agent (called group 'X', which can consist of a folate moiety for example that targets receptors on the surface of breast cancer cells to trigger cellular uptake), or a near-IR dye or MRI contrast agent (not shown) to observe localization of the nano-particles in the cells and ultimately tumors once the project is ready for in vivo efficacy studies.

Figure 30:
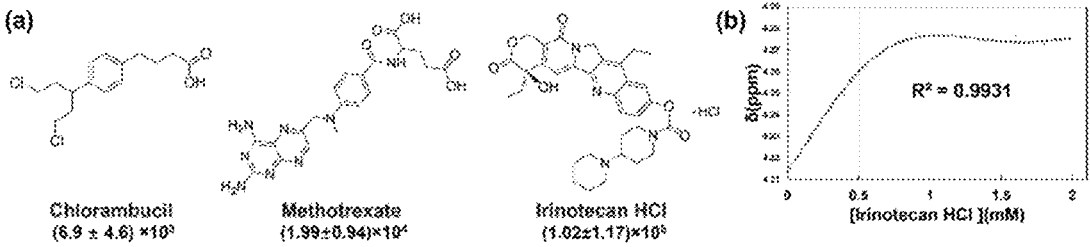
FIG. 30. (A) The chemical structure and names of three anti-cancer drugs are shown with their respective $K_a$ values for binding inside Nb-CD are shown in black underneath each name. (B) A titration curve for irinotecan that shows saturation at a 1:1 ratio of host to guest.

Recently, binding data (i.e., $K_a$ values) for the Nb-CD monomer was acquired with three common anti-cancer drugs (see e.g., FIG. 30). Each of these drugs show relatively high binding inside the cavity of CD, where irinotecan (one of the drugs used in FOLFIRNIOX) was found to bind the best with $K_a$=~$10^5$. These higher values are important in terms of the drug remaining inside the receptor during polymerization, as well as during cell uptake or transport in the blood stream to the site of cancerous tissue; ultimately resulting in continual release once localized in a tumor. In (I), the binding of an even larger set of anti-cancer drugs—that possess orthogonal mechanisms of action—inside the cavity of the Nb-CD monomer will be investigated, while also working to synthesize the Nb-PEG-X monomer. For the last part of (I) research, the release kinetics of all loaded drugs will be quantified to determine whether it is possible to release synergistic ratios that are more effective at killing aggressive forms of cancer.

(II) Establishing the Ring-Opening Metathesis Polymerization of Drug-Loaded Monomers, Cytotoxicity, and Release Kinetics The objective in (II) is to identify and optimize the conditions that are needed to polymerize each monomer, separately at first, and then ultimately together to generate the diblock copolymer consisting of drug-loaded Nb-CD and Nb-PEG-X. Since the Nb-CD monomer is already in hand, the initial conditions suitable for efficient ring-opening metathesis polymerization (commonly referred to as ROMP) will be established to make the unloaded homopolymer. The initial ROMP experiments of Nb-CD to make polyCD (see e.g., FIG. 9) were carried out in dimethylformamide as the solvent and at room temperature in the presence of a ruthenium-based catalyst—namely, Grubbs' $3^{rd}$ generation metathesis catalyst. This polymerization reaction yielded a polymer with a weight-average molecular weight ($M_w$) of 9390.2 g·mol$^{-1}$ (see e.g., FIG. 9, rightmost plot) and a moderate dispersity (Đ) value of 1.68, which is a measure of the molar mass distribution of a batch of polymers. Optimization of this polymerization (by adjusting the monomer concentration, temperature, catalyst loading, solvents, etc.) is continuing to prepare even higher molecular weight polymers with narrower dispersity values. This early result, however, is very encouraging and suggests that the polymerization to make the diblock copolymer is feasible.

During this stage of the research, the polyCD's toxicity will be assessed against healthy human umbilical vein endothelial cells (HUVECs, from ATCC), both loaded and unloaded, to determine the concentration that represents a lethal dose of 50% of the cells (i.e., LD$_{50}$). The drug-loaded polyCD's ability to kill different cancer cell lines using different drug-loaded monomers will also be tested.

Figure 31:
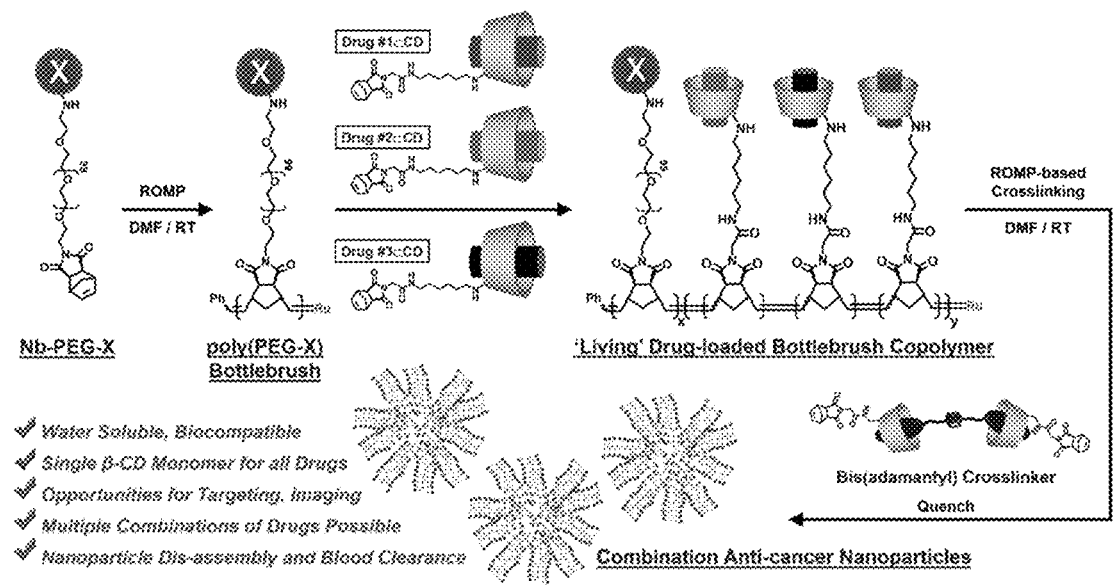
FIG. 31. Synthetic process to make the combination anti-cancer nanoparticles starting with ROMP of Nb-PEG-X, followed by the addition of several drug-loaded Nb-CD monomers (#'s 1-3) that generates the 'living' diblock copolymer, which is subsequently cross-linked with a di-functional cross linker to produce the final nanoparticle product.

(III) Synthesis of the Combination Drug-Loaded Bottlebrush Copolymer And Nanoparticle, and Assessment of Cytotoxicity and In Vitro Efficacy The focus of (III) is to bring the functional monomers together into a single platform. This will be achieved by carrying out ROMP of Nb-PEG-X initially to make the poly (PEG-X) bottlebrush polymer that still has an active or 'living' ruthenium species on one end (shown in red in FIG. 31) that can react further with additional monomers. These ROMP reactions usually take about 30-60 minutes, so the initial 'living' polymer can be generated quickly and ready for the next step. At this stage, I will add several different drug-loaded Nb-CD monomers, which will all add onto the growing polymer chain, the product of which will be a 'living' drug-loaded bottlebrush copolymer (see e.g., FIG. 31, top right). Next, crosslinking these copolymers can be performed using a double-norbornene crosslinker that consists of a bis(adamantyl) moiety (shown as a blue/black cartoon in the bottom right corner of FIG. 31). Since this crosslinker has two norbornene groups at its termini, it will react with the 'living' end of several copolymers, effectively crosslinking them into well-defined nanoparticles. These nanoparticles will not only be stable under physiological conditions as a result of the non-covalent binding interactions present throughout, but they will also be water soluble, biocompatible, and easily prepared with a multitude of drug combinations that may typically be used to treat aggressive forms of pancreatic or metastatic cancers.

Once made, the cytotoxicity of the nanoparticles (loaded and unloaded) will be assessed to determine their respective LD$_{50}$ values. Nanoparticles loaded with different combinations of anti-cancer drugs against several different cancer cell lines will also be investigated.

There may be some larger anti-cancer drugs which are too large to fit inside the cavity of β-CD. That being said, there are still entire families of anti-cancer drugs that will fit, such as camptothecin, doxorubicin, cisplatin, oxaliplatin, 5-fluorouracil, etc. Based on this, it is believed that there are several different clinical combinations of drugs (like FOL-FIRINOX) that can be pursued within this drug delivery system.

The timing of when the drugs are added to the supramolecular monomer hosts could be important. For example, this first approach will consist of polymerizing the pre-loaded monomers, however, if it is learned that a high percentage of drug cargo is released prematurely during the polymerization and dialysis steps, then loading the drugs post-polymerization (and before crosslinking to make the nanoparticles) will be investigated because the CD-based receptors will be open and available to bind a precise mixture of drugs, where the sequence is irrelevant.

These studies show the development of the disclosed combination drug delivery system, while also assessing its cytotoxicity and in vitro efficacy against a wide range of cancer cell lines. Different combinations of drugs can be investigated in terms of the overall feasibility to construct the drug-loaded nanoparticles, as well as their ability to be taken up by cells and release the different combinations of drugs once inside the cells. In vivo efficacy trials in mice can be performed that possess subcutaneous xenograft tumors comprised of pancreatic and ovarian cancer cells, but then in more complicated animal models, such as in genetically engineered mouse models of cancer originating in the pancreas.

What is claimed is:

1. A composition comprising a drug-delivery agent comprising a self-assembled nanoparticle, the nanoparticle consisting of a plurality of polymer components, wherein;

a. each polymer component comprises a hydrophobic region comprising at least two hydrophobic block polymers, and a hydrophilic region comprising at least one hydrophilic block polymer;

b. the at least two hydrophobic block polymers comprise:

i. a first hydrophobic block polymer comprising a plurality of first hydrophobic monomers, each first hydrophobic monomer comprising a first macrocyclic moiety covalently linked to norbornene and a first active compound non-covalently bound to the first macrocyclic moiety, wherein the norbornenes of the plurality of first hydrophobic monomers are polymerized to form a first portion of a backbone of each polymer component and the first macrocyclic moiety is selected from the group of macrocyclic moieties consisting of a cyclodextrin, a calixarene, a crown ether, and a cyclophane; and ii. a second hydrophobic block polymer comprising a plurality of second hydrophobic monomers, each second hydrophobic monomer comprising a second macrocyclic moiety covalently linked to norbornene and a second active compound non-covalently bound to the second macrocyclic moiety, wherein the norbornenes of the plurality of second hydrophobic monomers are polymerized to form a second portion of a backbone of each polymer component, wherein the second macrocyclic moiety is different from the first macrocyclic moiety, and the second macrocyclic moiety is selected from the group of macrocyclic moieties consisting of a cyclodextrin, a calixarene, a crown ether, and a cyclophane;

c. the at least one hydrophilic block polymer comprises a plurality of hydrophilic monomers, each hydrophilic monomer comprising a hydrophilic moiety covalently linked to norbornene, the hydrophilic moiety selected from the group of hydrophilic moieties consisting of a protonated L-arginine-glucosamine (LARGE) group, a protonated tert-butyloxycarbonyl (Boc)-protected arginine group, and a poly(ethylene glycol); wherein the norbornenes of the plurality of hydrophilic monomers are polymerized to form a third portion of the backbone of each polymer component;

d. the first, second and third backbone portions form a backbone of the polymer component; and e. the plurality of polymer components are self-assembled in a micelle arrangement comprising an inner core comprising the hydrophobic regions of the plurality of polymer components and an outer shell surrounding the inner core, the outer shell comprising the hydrophilic regions of the plurality of polymer components.

2. The composition of claim 1, wherein the first active compound and the second active compound are independently selected from:

a. an anticancer agent or an antibiotic;

b. an alkali metal cation, a transition metal cation, or a halogen anion; or c. a potassium cation or a protonated amine.

3. The composition of claim 1, wherein the hydrophilic moiety of the plurality of hydrophilic monomers consists of the poly(ethylene glycol) linked to an imaging agent, a targeting group, a binding group and any combination thereof.

4. The composition of claim 1, further comprising a non-covalent cross-linking group, an adamantane-functionalized crosslinker, or a bis(adamantyl) crosslinker capable of non-covalently binding two or more polymer components at their macrocyclic moieties.

5. The composition of claim 2, wherein the first macrocyclic moiety is the cyclodextrin, the first active compound is the antibiotic, the second macrocyclic moiety is the calixarene, and the second active compound is the alkali metal cation comprising $Ag^+$.

6. The composition of claim 2, wherein the drug-delivery agent is capable of:

targeting a bacteria cell surface;

destabilizing bacteria cell membranes;

exhibiting a controlled and sustained delivery of a silver ion $Ag^+$ and one or more antibiotics simultaneously, wherein the delivery of the $Ag^+$ induces oxidative stress in bacteria and disrupts disulfide bond formation in proteins, resulting in an increase in permeability of bacteria cellular membrane; and inducing collagen synthesis during wound healing.

7. The composition of claim 2, wherein the first and second macrocyclic moieties comprise a hydrophobic cavity capable of binding the first and second active compounds, respectively, with a $K_a$ of greater than about 100 $M^{-1}$ or capable of binding alkali metal cations or transition metal cations with a $K_a$ of greater than about $10^{-5}$ $M^{-1}$.

8. The composition of claim 2, wherein a. the cyclodextrin is a β-cyclodextrin;

b. the calixarene is independently selected from the group consisting of a thiacalix[n]arene and a tert-butyl-thiacalix[4]arene;

c. the crown ether is a [18]-crown-6 ether;

d. the anticancer agent is independently selected from the group consisting of: camptothecin; doxorubicin; cisplatin; oxaliplatin; 5-fluoruracil; chlorambucil; methotrexate; and irinotecan HCl;

e. the antibiotic is independently selected from the group consisting of: a β-lactam; amoxicillin; imipenem; an aminoglycoside; a quinolone; a fluoroquinolone; levofloxacin; chloramphenicol; a sulfonamide; sulfadiazine, sulfamethoxazole; tetracycline; linezolid; and a thiol New Delhi metallo-β-lactamase 1 (NDM-1) inhibitor; or f. the transition metal cation is selected from copper ion or a silver ion.

9. The composition of claim 2, wherein the calixarene further comprises a thioether-pyridine bridge, wherein the thioether-pyridine bridge increases binding of the transition metal cation inside the calixarene compared to a calixarene without the thioether-pyridine bridge.

10. The composition of claim 1, wherein the binding constant, $K_a$, is between about $10^2$-$10^5$ $M^{-1}$ for an antibiotic, an anticancer agent, an alkali metal cation, or a transition metal cation in the first and second macrocyclic moieties.

\* \* \* \* \*